(12) United States Patent
Gan et al.

(10) Patent No.: US 12,227,539 B2
(45) Date of Patent: Feb. 18, 2025

(54) MOGROSIDE COMPOUNDS AND USES THEREOF

(71) Applicant: Firmenich SA, Satigny (CH)

(72) Inventors: Xian-Wen Gan, Shanghai (CN); Dan-Ting Yin, Shanghai (CN); Robert Brauchli, Satigny (CH)

(73) Assignee: Firmenich SA, Satigny (CH)

( * ) Notice: Subject to any disclaimer, the term of this patent is extended or adjusted under 35 U.S.C. 154(b) by 840 days.

(21) Appl. No.: 17/413,017

(22) PCT Filed: Mar. 24, 2020

(86) PCT No.: PCT/EP2020/058158
§ 371 (c)(1),
(2) Date: Jun. 11, 2021

(87) PCT Pub. No.: WO2020/200916
PCT Pub. Date: Oct. 8, 2020

(65) Prior Publication Data
US 2022/0017563 A1   Jan. 20, 2022

(30) Foreign Application Priority Data

Apr. 4, 2019 (WO) ................ PCT/CN2019/081409

(51) Int. Cl.
| | |
|---|---|
| *A23L 2/60* | (2006.01) |
| *A23L 2/56* | (2006.01) |
| *A23L 27/30* | (2016.01) |
| *A23L 29/30* | (2016.01) |
| *C07J 17/00* | (2006.01) |

(52) U.S. Cl.
CPC ............... *C07J 17/005* (2013.01); *A23L 2/56* (2013.01); *A23L 2/60* (2013.01); *A23L 27/36* (2016.08); *A23L 29/30* (2016.08)

(58) Field of Classification Search
CPC .. C07J 17/005; A23L 2/56; A23L 2/60; A23L 27/36; A23L 29/30; A23L 33/125; A23V 2002/00; A23V 2250/24; A23V 2250/254; A23V 2250/60
See application file for complete search history.

(56) References Cited

U.S. PATENT DOCUMENTS

2017/0011903 A1   1/2017 Kozasa et al.

FOREIGN PATENT DOCUMENTS

WO   WO-2018220103 A1 * 12/2018 ........... A23C 9/1307

OTHER PUBLICATIONS

Zuliang Luo et al: "Liquid Chromatography With Tandem Mass Spectrometry Method for the Simultaneous Determination of Multiple Sweet Mogrosides in the Fruits of Siraitia Grosvenorii and Its Marketed Sweetners : Liquid Chromatography", Journal of Separation Science., vol. 39., No. 21., Oct. 5, 2016, pp. 4124-4135.
Lei Wang et al: "Cucurbitaneglycosides Derived From Mogroside IIE: Structure-Taste Relationships, Antioxidant Activity, and Acute Toxicity", Molecules, vol. 19, No. 8, Aug. 20, 2014, pp. 12676-12689.
Fu Li et al: "Cucurbitane Glycosides From the Fruit of Siraitia Grosvenori and Their Effects on Glucose Uptake in Human HEPG2 Cells in Vitro, Food Chemistry", vol. 228, Feb. 10, 2017, pp. 567-573.
Guisheng Zhou et al: "Biotransformation of Total Saponins in Siraitia Fructus By Human Intestinal Microbiota of Normal and Type 2 Diabetic Patients: Comprehensive Metabolite Identification and Metabolic Profile Elucidation Using LC-Q-TOF/MS", Journal of Agricultural and Food Chemistry, vol. 65, No. 8, Feb. 14, 2017, pp. 1518-1524.
Ochi M et al: "Sweet and Bitter Constituents of Wilbrandia Species", Food Chemistry, Elsevier Ltd, NL, vol. 115, No. 1, Jul. 1, 2009, pp. 61-65.
International Search Report and Written Opinion for corresponding International Application No. PCT/EP2020/058158 dated Aug. 14, 2020 (12 pages).

* cited by examiner

*Primary Examiner* — Yih-Horng Shiao
*Assistant Examiner* — Hoi Yan Lee
(74) *Attorney, Agent, or Firm* — Robert S. Dailey

(57) ABSTRACT

The various aspects presented herein relate to processes for preparing food ingredients, flavors and sweeteners from extracts of plants that contain mogrosides such as *Siraitia grosvenorii*. Further provided herein are formulations and uses of compositions made from the processes.

14 Claims, 46 Drawing Sheets

Mogroside V (Reference)
Main sweet component in
Monk fruit extract

MOGROSIDE COMPOUNDS AND USES THEREOF

CROSS-REFERENCE TO RELATED APPLICATIONS

The present application is the United States national stage application of PCT Application No. PCT/EP2020/058158, filed Mar. 24, 2020, which claims benefit of priority PCT Application No. PCT/CN2019/081409, filed Apr. 4, 2019, which is hereby incorporated by reference as though set forth herein in its entirety.

FIELD OF THE INVENTION

The present disclosure generally provides certain mogroside compounds, and their use to impart or modify taste of a comestible composition. In some aspects, the disclosure provides comestible compositions, such as flavored food or beverage products, that contain one or more of the mogroside compounds disclosed herein.

BACKGROUND

Natural sources of sweet compounds continue to be sought after, as negative health effects generated by the ingestion of sugar by large populations continue to concern health officials and mankind in general. The search for sweet plant extracts that have close to zero calorie contribution to a human's diet continues in order to find sweet and flavorful compounds that might replace sugars in order to reduce the instances of obesity, diabetes and cardiovascular diseases.

To date, various products have been proposed for addressing these problems. For instance, artificial high intensity sweeteners have been developed, which deliver a sweet taste at very low doses. Among the high intensity sweeteners already present in the market, sucralose, aspartame, acesulfame potassium, cyclamate, and saccharine are well-known alternatives of caloric sweeteners. However, there is a strong desire by an ever-increasing number of consumers for natural or naturally derived products in preference to their artificial counterparts. But many natural, low-calorie sweeteners impart a lingering off-taste to the food products to which they are added.

*Siraitia grosvenori* (also known as luo han guo or monk fruit), is a member of the Cucurbitaceae family. The plant is native to certain regions of southern and eastern Asia, particularly southern China. The sweet taste of the luo han guo fruit mainly comes from triterpene glycosides, which are present in the fruit at reasonably high quantities. These triterpene glycosides are generally known as mogrol glycosides or mogrosides. There are a number of mogrosides identified in luo han guo. A notable examples is Mogroside V (shown in FIG. 1), which has the highest concentration in the fruit compared to other mogroside compounds present. Mogrosides all have the same core structure, for example, a mogrol or oxo-mogrol core, and tend to differ from each other by number and type of glycosidic residues bonded to mogrol or oxo-mogrol core. Examples of a series of mogroside compounds are illustrated in U.S. Patent Application Publication No. 2012/0059071. Certain mogroside compounds have a relatively sweet taste, often 100 times sweeter than sucrose. Examples of such sweet mogrosides include Mogroside V, and its isomer Isomogroside V. Isomogroside V is disclosed in U.S. Patent Application Publication No. 2011/0027413. Even so, such readily available mogrosides tend to impart a bitter aftertaste, which limits their broader adoption relative to rebaudiosides and other steviol glycosides.

U.S. Patent Application Publication No. 2010/310751 discloses sweetening compositions that can be used to replace sugar, which comprise the extract of the fruit of one or more plants from the Cucurbitaceae family, such as Mogroside V, and mono-ammonium glycyrrhizin. PCT Publication No. WO 2015/082012 and PCT Publication No. WO 2018/089469 disclose triterpene glycoside compounds and sweetening compositions comprising various triterpene-glycoside compounds. PCT Publication No. WO 2017/075257 discloses compounds that are useful as sweet tasting agents or sweetness enhancers.

Despite these prior efforts, there remains a need to develop new sweeteners or sweetness modifying compounds. The present invention now addresses these needs and provides important improvements in this area.

SUMMARY

In a first aspect, the disclosure provides compounds of formula (I):

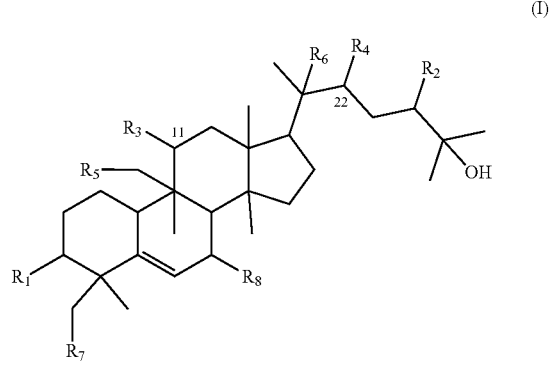

or salts thereof, in the form of any one of their stereoisomers or mixtures thereof; wherein $R_1$ and $R_2$ are independently —OH or a sugar moiety, wherein the sugar moiety is a monosaccharide or an oligosaccharide; and wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose and glucuronic acid; and wherein the oligosaccharide consists of 2 to 5 monosaccharide units; and wherein $R_3$ is an —OH group, or $R_3$ combines with the hydrogen atom attached to the 11-position to form an oxo (=O) group; and wherein $R_4$, $R_5$, and $R_8$ are independently a hydrogen atom, an —OH group, or, combine with the hydrogen atom attached to the same carbon to form an oxo (=O) group; and wherein $R_6$ is a hydrogen atom or an —OH group; and wherein $R_7$ is a hydrogen atom, an —OH group or a sugar moiety, wherein the sugar moiety is selected from the group consisting of a monosaccharide or an oligosaccharide, wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose and glucuronic acid; and wherein the oligosaccharide consists of 2 to 5 monosaccharide units.

In some embodiments of the foregoing aspect, four groups among $R_4$, $R_5$, $R_6$, $R_7$ and $R_8$ groups are a hydrogen atom, and the other group is not a hydrogen atom. In some further embodiments, the compound of formula (I) is not 22-hydroxybryodulcosigenin, 7-oxomogroside IIe, 7-oxomogroside IIIe, 7-oxomogroside III, 7-oxomogroside IV, 7-oxomogroside V, compound 25 described in PCT Publication No. WO 2017075257, or 20-hydroxy-11-oxomogroside I a1.

In a second aspect, the disclosure provides compounds of formula (II):

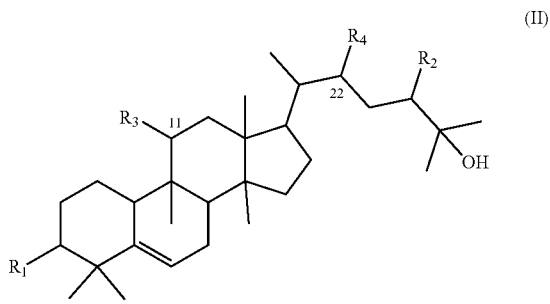

Or salts thereof, in the form of any of its stereoisomers or mixtures thereof; wherein $R_1$ and $R_2$ are independently —OH or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; wherein the oligosaccharide consists of 2 to 5 monosaccharide units; wherein $R_3$ and $R_4$ are independently —OH, or combine with the hydrogen atom attached to the same carbon atom to form an oxo (=O) group. In some embodiments thereof, the compound of formula (II) is not 22-hydroxybryodulcosigenin.

In a third aspect, the disclosure provides a compound of formula (III):

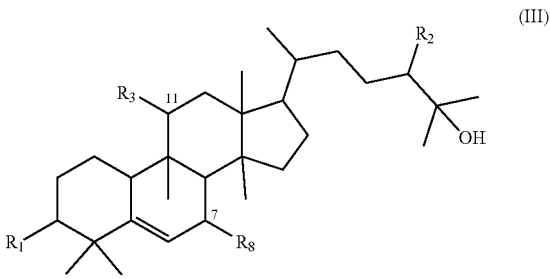

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; and wherein the monosaccharide or the monosaccharide units of the oligosaccharide are selected from the group consisting of glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; wherein $R_3$ and $R_8$ are independently an —OH group, or combine with the hydrogen atom attached to the same carbon atom to form an oxo (=O) group. In some embodiments thereof, the compound of formula (III) is not 7-oxomogroside IIe, 7-oxomogroside IIIe, 7-oxomogroside III, 7-oxomogroside IV, 7-oxomogroside V, or compound 25 described in PCT Publication No. WO 2017/075257.

In a fourth aspect, the disclosure provides a compound of formula (IV):

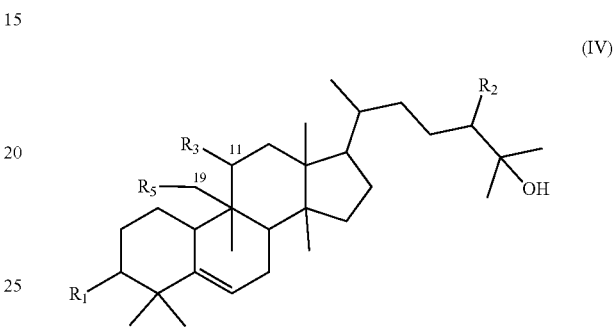

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; and wherein $R_3$ and $R_5$ independently are an —OH group, or combine with the hydrogen atom attached to the same carbon to form an oxo (=O) group.

In a fifth aspect, the disclosure provides a compound of formula (V):

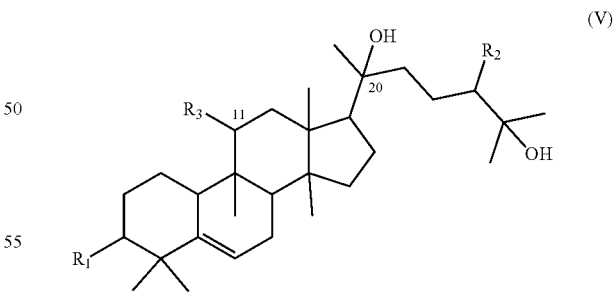

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; and wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxyribose, hamamelose, and glucuronic acid; and wherein the oligosaccharide consists of 2 to 5 monosaccharide units; and wherein R₃ is an —OH group, or combines with the hydrogen atom attached to the same carbon atom to form an oxo (═O) group. In some embodiments thereof, the compound of formula (V) is not 20-hydroxy-11-oxomogroside I a1.

In a sixth aspect, the disclosure provides a compound of formula (VI):

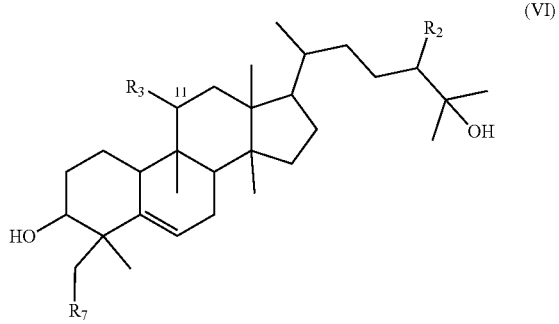

(VI)

or a salt thereof, in the form of any of its stereoisomers or mixtures thereof; wherein $R_7$ and $R_2$ are independently an —OH group or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; and wherein $R_3$ is an —OH group or combines with the hydrogen atom attached to the same carbon atom to form an oxo (═O) group.

In some further embodiments of any of the foregoing aspects, the monosaccharide or the monosaccharide units of the oligosaccharide are selected from the group consisting of: glucose, rhamnose, and galactose. In some further such embodiments, the monosaccharide or the monosaccharide units of the oligosaccharide are selected from the group consisting of: glucose and rhamnose.

In some further embodiments of the foregoing aspects, the oligosaccharide is selected from the group consisting of: glucosyl-(1→2)-glucose, glucosyl-(1→3)-glucose, glucosyl-(1→4)-glucose, glucosyl-(1→6)-glucose, glucosyl-(1→3)-[glucosyl-(1→2)]-glucose, glucosyl-(1→4)-[glucosyl-(1→2)]-glucose, glucosyl-(1→6)-[glucosyl-(1→2)]-glucose, glucosyl-(1→2)-glucosyl-(1→2)-glucose, glucosyl-(1→3)-glucosyl-(1→2)-glucose, glucosyl-(1→4)-glucosyl-(1→2)-glucose, glucosyl-(1→6)-glucosyl-(1→2)-glucose, glucosyl-(1→2)-glucosyl-(1→4)-glucose, glucosyl-(1→3)-glucosyl-(1→4)-glucose, glucosyl-(1→4)-glucosyl-(1→4)-glucose, glucosyl-(1→6)-glucosyl-(1→4)-glucose, glucosyl-(1→2)-glucosyl-(1→6)-glucose, glucosyl-(1→3)-glucosyl-(1→6)-glucose, glucosyl-(1→4)-glucosyl-(1→6)-glucose, glucosyl-(1→6)-glucosyl-(1→6)-glucose, glucosyl-(1→2)-glucosyl-(1→6)-[glucosyl-(1→2)]-glucose, glucosyl-(1→3)-glucosyl-(1→6)-[glucosyl-(1→2)]-glucose, glucosyl-(1→4)-glucosyl-(1→6)-[glucosyl-(1→2)]-glucose, glucosyl-(1→6)-glucosyl-(1→6)-[glucosyl-(1→2)]-glucose, glucosyl-(1→6)-[glucosyl-(1→2)-glucosyl-(1→2)]-glucose, glucosyl-(1→6)-[glucosyl-(1→3)-glucosyl-(1→2)]-glucose, glucosyl-(1→6)-[glucosyl-(1→4)-glucosyl-(1→2)]-glucose, and glucosyl-(1→6)-[glucosyl-(1→6)-glucosyl-(1→2)]-glucose. In some further such embodiments, the oligosaccharide is selected from the group consisting of: glucosyl-(1→2)-glucose, glucosyl-(1→4)-glucose, glucosyl-(1→6)-glucose and glucosyl-(1→6)-[glucosyl-(1→2)]-glucose.

In some further embodiments of the first aspect, the compound of formula (I) is selected from the group consisting of: 1-[(6-O-hexopyranosylhexopyranosyl)oxy]-11,22,25-trihydroxy-9,10,14-trimethyl-4,9-cyclo-9,10-secocholest-5-en-24-yl 6-O-hexopyranosylhexopyranoside (Compound 1), 1-(hexopyranosyloxy)-11,22,25-trihydroxy-9,10,14-trimethyl-4,9-cyclo-9,10-secocholest-5-en-24-yl 6-O-hexopyranosylhexopyranoside (Compound 2), 24-[(6-O-hexopyranosylhexopyranosyl)-oxy]-11,22,25-trihydroxy-9,10,14-trimethyl-4,9-cyclo-9,10-secocholest-5-en-1-yl 4-O-hexopyranosylhexopyranoside (Compound 3), 1-[(6-O-hexopyranosylhexopyranosyl)-oxy]-7,11,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 4), 1-[(6-O-hexopyranosylhexopyranosyl)oxy]-25-hydroxy-9-(hydroxymethyl)-10,14-dimethyl-11-oxo-4,9-cyclo-9,10-secocholest-5-en-24-yl hexopyranosyl-(1→2)-[hexopyranosyl-(1→6)]hexopyranoside (Compound 5), 9-formyl-1-[(6-O-hexopyranosylhexopyranosyl)oxy]-25-hydroxy-10,14-dimethyl-11-oxo-4,9-cyclo-9,10-secocholest-5-en-24-yl hexopyranosyl-(1→2)-[hexopyranosyl-(1→6)]hexopyranoside (Compound 6), 1-[(6-O-hexopyranosyl-hexopyranosyl)oxy]-11,20,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 7), 1-(hexopyranosyloxy)-20,25-dihydroxy-9,10,14-trimethyl-11-oxo-4,9-cyclo-9,10-secocholest-5-en-24-yl 6-O-hexopyranosylhexopyranoside (Compound 8), 24-[(6-O-hexopyranosylhexopyranosyl)oxy]-20,25-dihydroxy-9,10,14-trimethyl-11-oxo-4,9-cyclo-9,10-secocholest-5-en-1-yl hexopyranosyl-(1→2)-[hexopyranosyl-(1→6)]hexo-pyranoside (Compound 9), and (24-{[hexopyranosyl-(1→6)hexopyranosyl-(1→6)hexopyranosyl]oxy}-1,25-dihydroxy-9,14-dimethyl-11-oxo-4,9-cyclo-9,10-secocholest-5-en-10-yl)methyl hexopyranosyl-(1→6)-[hexopyranosyl-(1→4)hexopyranosyl-(1→2)] hexopyranoside (Compound 10).

In some other embodiments of the first aspect, the compound of formula (I) is selected from the group consisting of: (1S,4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a), (1S,4R,9beta,11alpha,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a), (1S,4R,9beta,11beta,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b), (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a), (1S,4R,9beta,11alpha,24R)-1-{[6-O-(beta-D-glucopyranosyl)-beta-D-glucopyranosyl]oxy}-7,11,25- trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a), (1S,4R,9beta, 24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a), (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a), (1S,4R,9beta, 11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a), (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a), (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a), and [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).

In a seventh aspect, the disclosure provides a compound, wherein the compound is a compound selected from the group consisting of: 1-[(6-O-hexopyranosyl-hexopyranosyl)oxy]-11,25-dihydroxy-9,10,14-trimethyl-4,9-cyclo-9,10-secocholest-5-en-24-yl hexopyranosyl-(1→6)-[hexopyranosyl-(1→4)hexopyranosyl-(1→2)]hexopyranoside (Compound 12), 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→2)-[hexopyranosyl-(1→6)hexopyranosyl-(1→6)]hexopyranoside (Compound 13), 1-{[hexopyranosyl-(1→2)-[hexopyranosyl-(1→6)]hexopyranosyl]oxy}-11,25-dihydroxy-9,10,14-trimethyl-4,9-cyclo-9,10-secocholest-5-en-24-yl hexopyranosyl-(1→2)-[hexopyranosyl-(1→6)]hexopyranoside (Compound 14), 1-[(6-O-hexopyranosylhexopyranosyl)oxy]-25-hydroxy-9,10,14-trimethyl-4,9-cyclo-9,10-secocholest-5-en-24-yl 2-O-hexopyranosylhexopyranoside (Compound 15), and any salts thereof, in the form of any of their stereoisomers or mixtures thereof.

In an eighth aspect, the disclosure provides a compound, wherein the compound is a compound selected from the group consisting of: (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a), (1S,4R,9beta, 11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a), (1S,4R,9beta,11beta,24R)-1-{[beta-D-glucopyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a), (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a), and any salts thereof.

In a ninth aspect, the disclosure provides a method of enhancing a sweet taste of a flavored article, the method comprising: providing a flavored article, and introducing a compound of the first through eighth aspects to the flavored article, such as a flavored food or beverage product. In some such embodiments, the compound is introduced in an amount effective to enhance the sweet taste of the flavored article.

In a tenth aspect, the disclosure provides the use of a compound of any of the first through eighth aspects to enhance a sweet taste of a flavored article, such as a flavored food or beverage product.

In an eleventh aspect, the disclosure provides a comestible composition comprising a compound of any of the first through eighth aspects. In some embodiments thereof, the comestible composition comprises a carrier, such as a bulking agent (such as erythritol, allulose, a cellulosic material, or any combination thereof) or water.

In a twelfth aspect, the disclosure provides a flavored article, which comprises a comestible composition of the eleventh aspect. In some embodiments thereof, the flavored article is a flavored food or beverage product.

DETAILED DESCRIPTION

Figure 1:
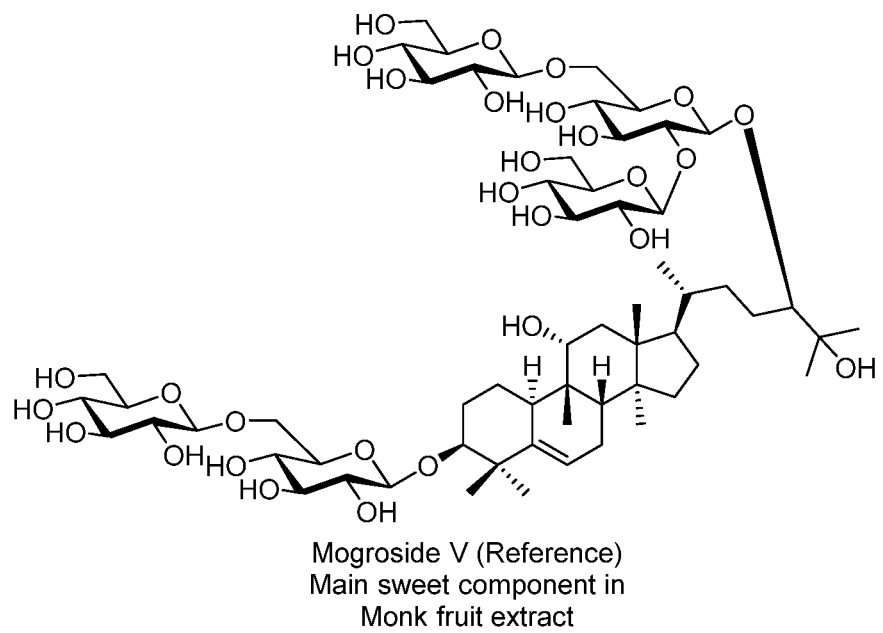
FIG. 1 shows the chemical structure of mogroside V.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The present disclosure provides high intensity sweeteners, sweetness modifiers, and sweetness enhancers comprising a mogroside compound disclosed herein. In some embodiments, the mogroside compound disclosed herein are obtained from the extract of Siraitia grosvenori fruits. In other embodiments, the mogroside compounds disclosed herein are synthesized by enzymatic processes. In some embodiments, these mogroside compounds are used as ingredients for producing, enhancing, improving and modifying the sweet taste of flavored articles and edible products or as taste modifiers.

The present disclosure also provides sweetening compositions and flavored articles containing the sweetening compositions, where the compositions include a mogroside compound disclosed herein. In some embodiments, the mogroside compounds are present in an amount that produces, enhances, or improves the sweetening effect. In some embodiments, the flavored article comprises a food matrix, a food substance, or an edible product.

Mogroside Compounds

In a first aspect, the disclosure provides a compound, wherein the compound is a compound of formula (I):

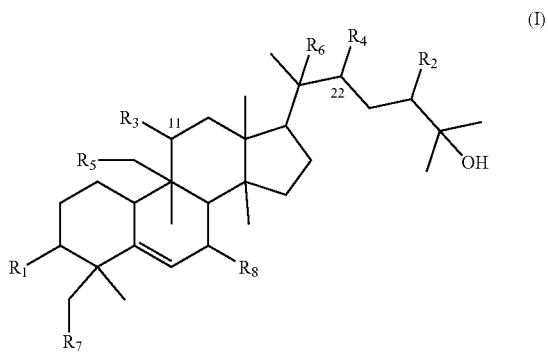

(I)

or a salt thereof, in the form of any of its stereoisomers or a mixture thereof; wherein $R_1$ and $R_2$ are independently an —OH group or a sugar moiety, wherein the sugar moiety is a monosaccharide or an oligosaccharide; and wherein the monosaccharide and the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, glucuronic acid, and any combinations thereof; and wherein the oligosaccharide consists of from 2 to 5 monosaccharide units; and wherein $R_3$ is an —OH group or combines with the hydrogen atom attached to the same carbon atom to form an oxo group (=O); and wherein $R_4$, $R_5$, and $R_8$ are independently a hydrogen atom, an —OH group, or combine with the hydrogen atom attached to the same carbon atom to form an oxo group; and wherein $R_6$ is a hydrogen atom or an —OH group; and wherein $R_7$ is a hydrogen atom, an —OH group or a sugar moiety, wherein the sugar moiety is a monosaccharide or an oligosaccharide; and wherein the monosaccharide and the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, glucuronic acid, and any combinations thereof; and wherein the oligosaccharide consists of from 2 to 5 monosaccharide units.

In some embodiments thereof, four groups among $R_4$, $R_5$, $R_6$, $R_7$, and $R_8$ are a hydrogen atom and the other is not a hydrogen atom. In some other embodiments thereof, the compound of formula (I) is not 22-hydroxybryodulcosigenin, 7-oxomogroside IIe, 7-oxomogroside IIIe, 7-oxomogroside III, 7-oxomogroside IV, 7-oxomogroside V, compound 25 described in PCT Publication No. WO 2017/075257, 20-hydroxy-11-oxomogroside I a1.

Note that various nomenclature may be used to describe mogroside compounds. For example, "7-oxomogroside IIe" refers to the same compound as "7-oxomogroside II E" or "7-oxomogroside II$_E$" and the like. Thus, lower-case letters may be used in circumstances where it may be more common to have a space followed by a capital letter of a capital letter in a subscript form.

In a second aspect, the disclosure provides a compound, wherein the compound is a compound of formula (II):

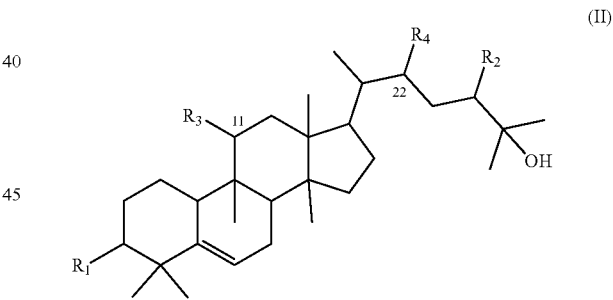

(II)

or salts thereof, in the form of any of its stereoisomers or mixtures thereof; wherein $R_1$ and $R_2$ are independently —OH or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; wherein the oligosaccharide consists of 2 to 5 monosaccharide units; wherein $R_3$ and $R_4$ are independently —OH, or combine with the hydrogen atom attached to the same carbon atom to form an oxo (=O) group. In some embodiments thereof, the compound of formula (II) is not 22-hydroxybryodulcosigenin.

In a third aspect, the disclosure provides a compound, wherein the compound is a compound of formula (III):

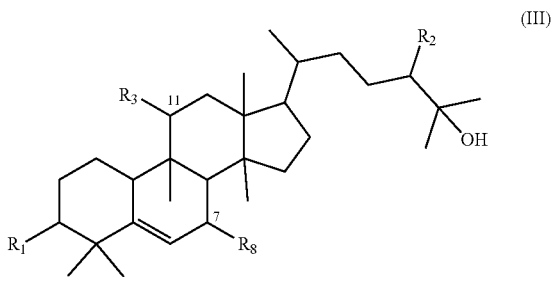

(III)

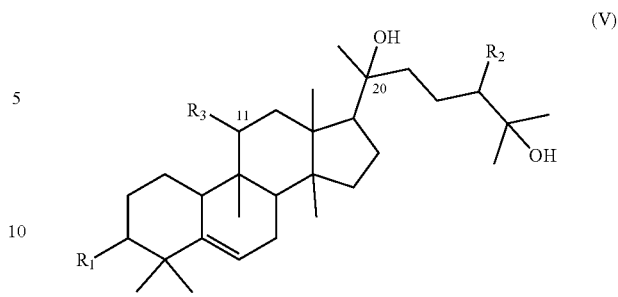

(V)

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; and wherein the monosaccharide or the monosaccharide units of the oligosaccharide are selected from the group consisting of glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; wherein $R_3$ and $R_8$ are independently an —OH group, or combine with the hydrogen atom attached to the same carbon atom to form an oxo (=O) group. In some embodiments thereof, the compound of formula (III) is not 7-oxomogroside IIe, 7-oxomogroside IIIe, 7-oxomogroside III, 7-oxomogroside IV, 7-oxomogroside V, or compound 25 described in PCT Publication No. WO 2017/075257.

In a fourth aspect, the disclosure provides a compound, wherein the compound is a compound of formula (IV):

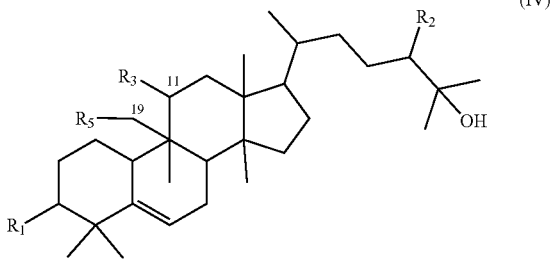

(IV)

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; and wherein $R_3$ and $R_5$ independently are an —OH group, or combine with the hydrogen atom attached to the same carbon to form an oxo (=O) group.

In a fifth aspect, the disclosure provides a compound, wherein the compound is a compound of formula (V):

or a salt thereof, in the form of any of its stereoisomers or mixtures thereof; wherein $R_1$ and $R_2$ are independently an —OH group or a sugar moiety, wherein the sugar moiety is a monosaccharide or an oligosaccharide; and wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; and wherein $R_3$ is an —OH group, or combines with the hydrogen atom attached to the same carbon atom to form an oxo (=O) group. In some embodiments thereof, the compound of formula (V) is not 20-hydroxy-11-oxomogroside I a1.

In a sixth aspect, the disclosure provides a compound, wherein the compound is a compound of formula (VI):

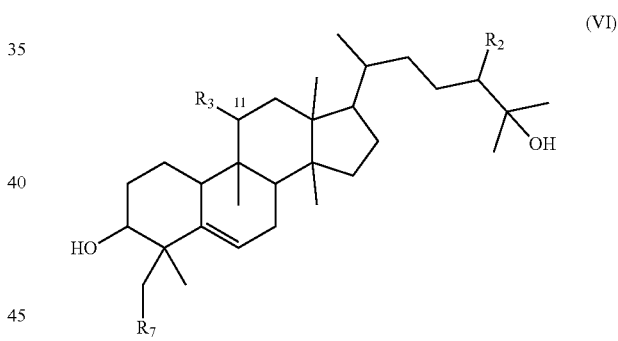

(VI)

or a salt thereof, in the form of any of its stereoisomers or mixtures thereof; wherein $R_7$ and $R_2$ are independently an —OH group or a sugar moiety, wherein the sugar moiety is a monosaccharide or an oligosaccharide; wherein the monosaccharide or the monosaccharide units of the oligosaccharide are selected from the group consisting of: glucose, rhamnose, galactose, xylose, fructose, mannose, tagatose, sorbose, ribose, arabinose, xylulose, ribulose, 6-deoxy-glucose, 6-deoxy-galactose, 6-deoxy-mannose, 2-deoxy-ribose, hamamelose, and glucuronic acid; and wherein the oligosaccharide consists of 2 to 5 monosaccharide units; and wherein $R_3$ is an —OH group or combines with the hydrogen atom attached to the same carbon atom to form an oxo (=O) group.

Any compounds of the preceding six aspects, including any embodiments thereof, may also be referred to herein as "mogroside compounds."

In some embodiments of any of the foregoing aspects, the monosaccharide or the monosaccharide units of the oligosaccharide are selected from the group consisting of: glucose, rhamnose, galactose, and any combinations thereof. In some further embodiments, the monosaccharide or the monosaccharide units of the oligosaccharide are selected from the group consisting of: glucose, rhamnose, and any combinations thereof.

In some embodiments of any of the foregoing aspects, the oligosaccharide is selected from the group consisting of: glucosyl-(1→2)-glucose, glucosyl-(1→3)-glucose, glucosyl-(1→4)-glucose, glucosyl-(1→6)-glucose, glucosyl-(1→3)-[glucosyl-(1→2)]-glucose, glucosyl-(1→4)-[glucosyl-(1→2)]-glucose, glucosyl-(1→6)-[glucosyl-(1→2)]-glucose, glucosyl-(1→2)-glucosyl-(1→2)-glucose, glucosyl-(1→3)-glucosyl-(1→2)-glucose, glucosyl-(1→4)-glucosyl-(1→2)-glucose, glucosyl-(1→6)-glucosyl-(1→2)-glucose, glucosyl-(1→2)-glucosyl-(1→4)-glucose, glucosyl-(1→3)-glucosyl-(1→4)-glucose, glucosyl-(1→4)-glucosyl-(1→4)-glucose, glucosyl-(1→6)-glucosyl-(1→4)-glucose, glucosyl-(1→2)-glucosyl-(1→6)-glucose, glucosyl-(1→3)-glucosyl-(1→6)-glucose, glucosyl-(1→4)-glucosyl-(1→6)-glucose, glucosyl-(1→6)-glucosyl-(1→6)-glucose, glucosyl-(1→2)-glucosyl-(1→6)-[glucosyl-(1→2)]-glucose, glucosyl-(1→3)-glucosyl-(1→6)-[glucosyl-(1→2)]-glucose, glucosyl-(1→4)-glucosyl-(1→6)-[glucosyl-(1→2)]-glucose, glucosyl-(1→6)-glucosyl-(1→6)-[glucosyl-(1→2)]-glucose, glucosyl-(1→6)-[glucosyl-(1→2)-glucosyl-(1→2)]-glucose, glucosyl-(1→6)-[glucosyl-(1→3)-glucosyl-(1→2)]-glucose, glucosyl-(1→6)-[glucosyl-(1→4)-glucosyl-(1→2)]-glucose, and glucosyl-(1→6)-[glucosyl-(1→6)-glucosyl-(1→2)]-glucose.

In some embodiments of any of the foregoing aspects, the oligosaccharide is selected from the group consisting of: glucosyl-(1→2)-glucose, glucosyl-(1→4)-glucose, glucosyl-(1→6)-glucose, and glucosyl-(1→6)-[glucosyl-(1→2)]-glucose.

In some embodiments of the first aspect, the compound of formula (I) is selected from the group consisting of: 1-[(6-O-hexopyranosylhexopyranosyl)oxy]-11,22,25-trihydroxy-9,10,14-trimethyl-4,9-cyclo-9,10-secocholest-5-en-24-yl 6-O-hexopyranosylhexopyranoside (Compound 1), 1-(hexopyranosyloxy)-11,22,25-trihydroxy-9,10,14-trimethyl-4,9-cyclo-9,10-secocholest-5-en-24-yl 6-O-hexopyranosylhexopyranoside (Compound 2), 24-[(6-O-hexopyranosylhexopyranosyl)oxy]-11,22,25-trihydroxy-9,10,14-trimethyl-4,9-cyclo-9,10-secocholest-5-en-1-yl 4-O-hexopyranosylhexopyranoside (Compound 3), 1-[(6-O-hexopyranosylhexopyranosyl)oxy]-7,11,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 4), 1-[(6-O-hexopyranosylhexopyranosyl)oxy]-25-hydroxy-9-(hydroxymethyl)-10,14-dimethyl-11-oxo-4,9-cyclo-9,10-secocholest-5-en-24-yl hexopyranosyl-(1→2)-[hexopyranosyl-(1→6)]hexopyranoside (Compound 5), 9-formyl-1-[(6-O-hexopyranosyl-hexopyranosyl)oxy]-25-hydroxy-10,14-dimethyl-11-oxo-4,9-cyclo-9,10-secocholest-5-en-24-yl hexopyranosyl-(1→2)-[hexopyranosyl-(1→6)]hexopyranoside (Compound 6), 1-[(6-O-hexopyranosylhexopyranosyl)oxy]-11,20,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 7), 1-(hexopyranosyloxy)-20,25-dihydroxy-9,10,14-trimethyl-11-oxo-4,9-cyclo-9,10-secocholest-5-en-24-yl 6-O-hexopyranosylhexopyranoside (Compound 8), 24-[(6-O-hexopyranosylhexopyranosyl)oxy]-20,25-dihydroxy-9,10,14-trimethyl-11-oxo-4,9-cyclo-9,10-secocholest-5-en-1-yl hexopyranosyl-(1→2)-[hexopyranosyl-(1→6)]hexopyranoside (Compound 9), and (24-{[hexopyranosyl-(1→6)hexopyranosyl-(1→6)hexopyranosyl]oxy}-1,25-dihydroxy-9,14-dimethyl-11-oxo-4,9-cyclo-9,10-secocholest-5-en-10-yl)methyl hexopyranosyl-(1→6)-[hexopyranosyl-(1→4)hexopyranosyl-(1→2)]hexopyranoside (Compound 10), in the form of any one of their stereoisomers or a mixture thereof.

In some embodiments of the first aspect, the compound of formula (I) is selected from the group consisting of: (1S,4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a), (1S,4R,9beta,11alpha,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a), (1S,4R,9beta,11beta,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b), (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a), (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a), (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a), (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a), (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a), (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a), (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a), and [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).

In some embodiments of any of the foregoing aspects, the mogroside compound is selected from the group consisting of: 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→6)-[hexopyranosyl-(1→4)hexopyranosyl-(1→2)]hexopyranoside (Compound 12), 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→2)-[hexopyranosyl-(1→6)hexopyranosyl-(1→6)]hexopyranoside (Compound 13), 1-{[hexopyranosyl-(1→2)-[hexopyranosyl-(1→6)]hexopyranosyl]oxy}-11,25-dihydroxy-9,10,14-trimethyl-4,9-cyclo-9,10-secocholest-5-en-24-yl hexopyranosyl-(1→2)-[hexopyranosyl-(1→6)]hexopyranoside (Compound 14), and 1-[(6-O-hexopyranosylhexopyranosyl)oxy]-25-hydroxy-9,10,14-trimethyl-4,9-cyclo-9,10-secocholest-5-en-24-yl 2-O-hexopyranosylhexopyranoside (Compound 15), in the form of any one of their stereoisomers or a mixture thereof.

In some embodiments of any of the foregoing aspects, the mogroside compound is selected from the group consisting of: (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a), (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a), (1S,4R,9beta,11beta,24R)-1-{[beta-D-glucopyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a), and (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).

In embodiments of the second aspect, the mogroside compound is a compound of the formula:

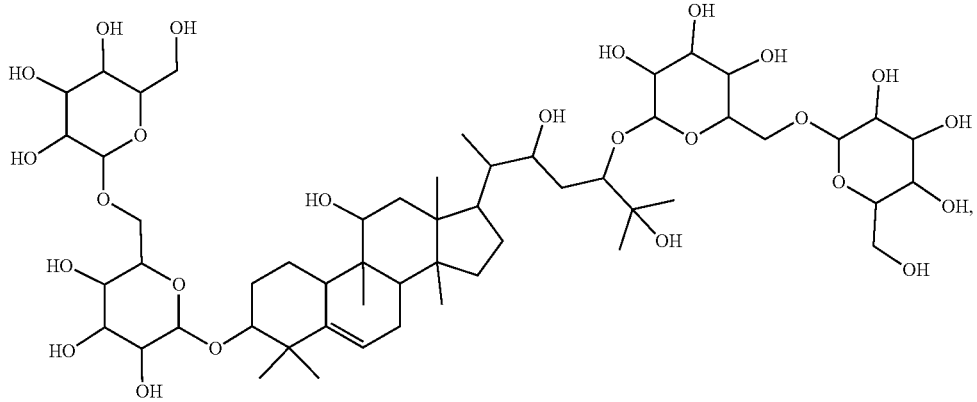

also referred to herein as 1-[(6-O-hexopyranosylhexopyranosyl)oxy]-11,22,25-trihydroxy-9,10,14-trimethyl-4,9-cyclo-9,10-secocholest-5-en-24-yl 6-O-hexopyranosylhexopyranoside (Compound 1).

In a further embodiment, the mogroside compound is a compound of the formula:

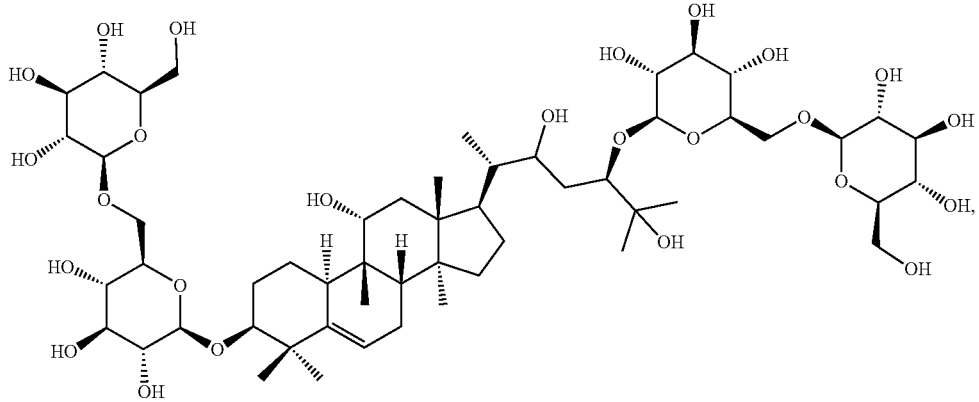

also referred to herein as (1S,4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-seco-cholest-5-en-24-yl 6-O-beta-D-glucopyranosyl-beta-D-glucopyranoside (22-hydroxy-mogroside IVa, Compound 1a).

In another embodiment, the mogroside compound is a compound of the formula:

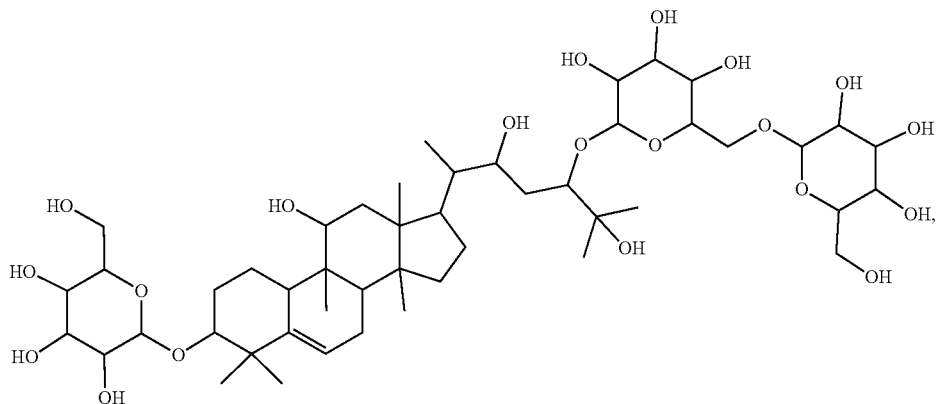

also referred to herein as 1-(hexopyranosyloxy)-11,22,25-trihydroxy-9,10,14-trimethyl-4,9-cyclo-9,10-secocholest-5-en-24-yl 6-O-hexopyranosylhexopyranoside (Compound 2).

In a further embodiments, the mogroside compound is a compound of the formula:

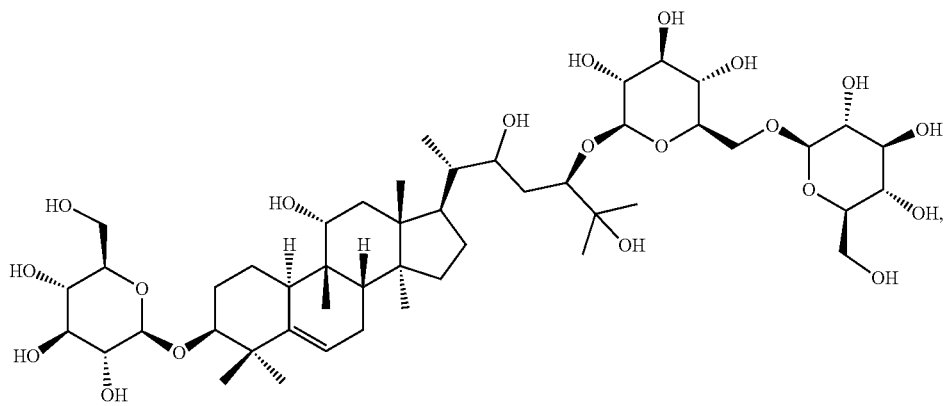

also referred to herein as (1S,4R,9beta,11alpha,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a).

In a further embodiment, the mogroside compound is a compound of the formula:

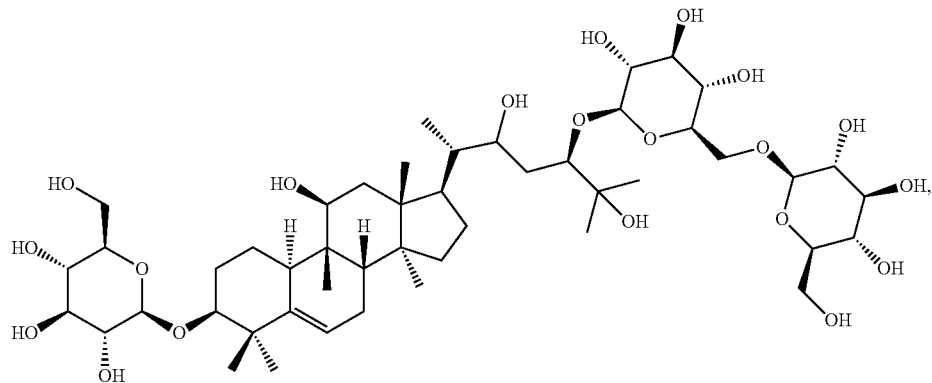

also referred to herein as (1S,4R,9beta,11beta,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b).

In some embodiments, the mogroside compound is a compound of the formula:

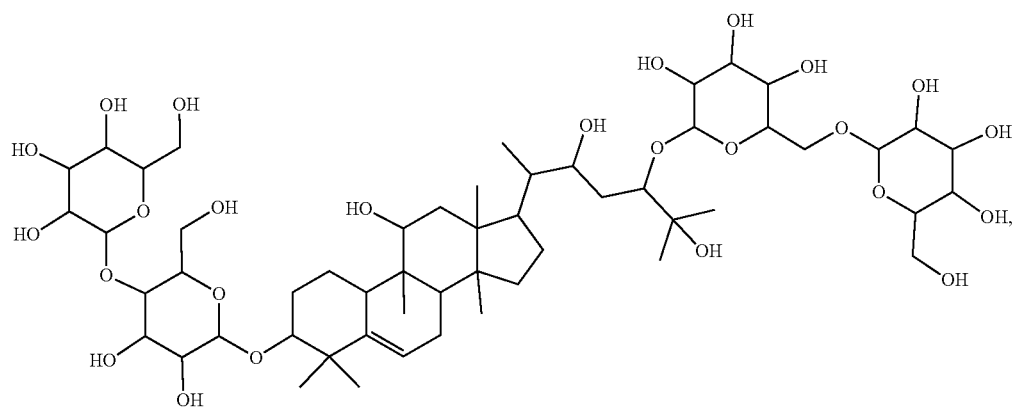

also referred to herein as 24-[(6-O-hexopyranosylhexopyranosyl)oxy]-11,22,25-trihydroxy-9,10,14-trimethyl-4,9-cyclo-9,10-secocholest-5-en-1-yl 4-O-hexopyranosylhexopyranoside (Compound 3).

In a further embodiment, the mogroside compound is a compound of the formula:

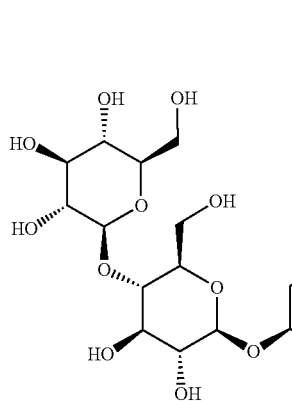
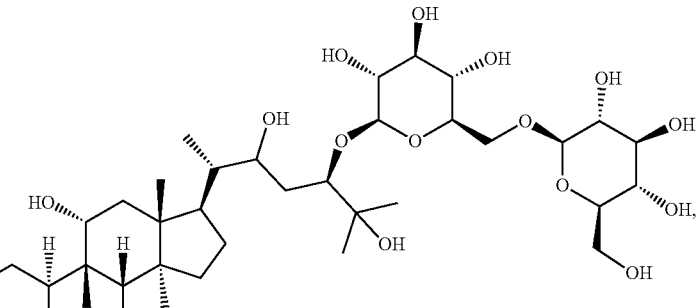

referred to herein as (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-seco-cholest-5-en-1-yl 4-O-beta-D-glucopyranosyl-beta-D-glucopyranoside (22-hydroxy-isomogroside IVa, Compound 3a).

In some embodiments, the mogroside compound is a compound of the formula:

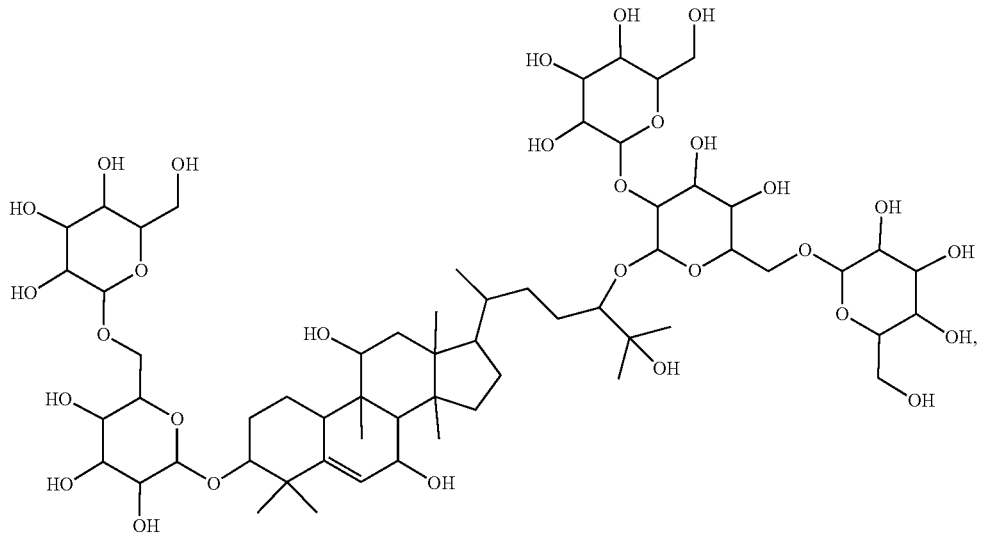

also referred to herein as 1-[(6-O-hexopyranosylhexopyranosyl)oxy]-7,11,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 4).

In a further embodiment, the mogroside compound is a compound of the formula:

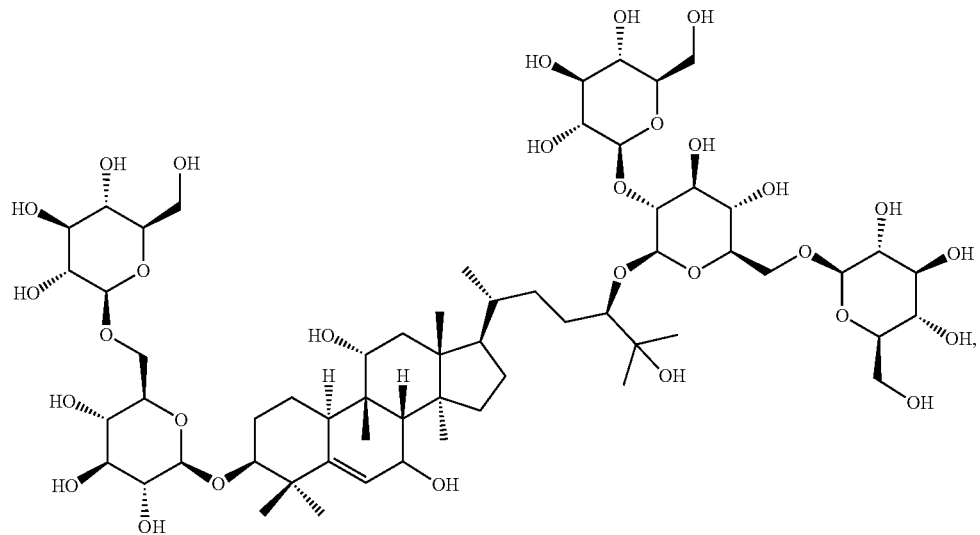

also referred to herein as (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-seco-cholest-5-en-24-yl beta-D-glucopyranosyl-(1→2)-[beta-D-glucopyranosyl-(1→6)]-beta-D-glucopyranoside (7-hydroxy-mogroside V, Compound 4a).

In some embodiments, the mogroside compound is a compound of the formula:

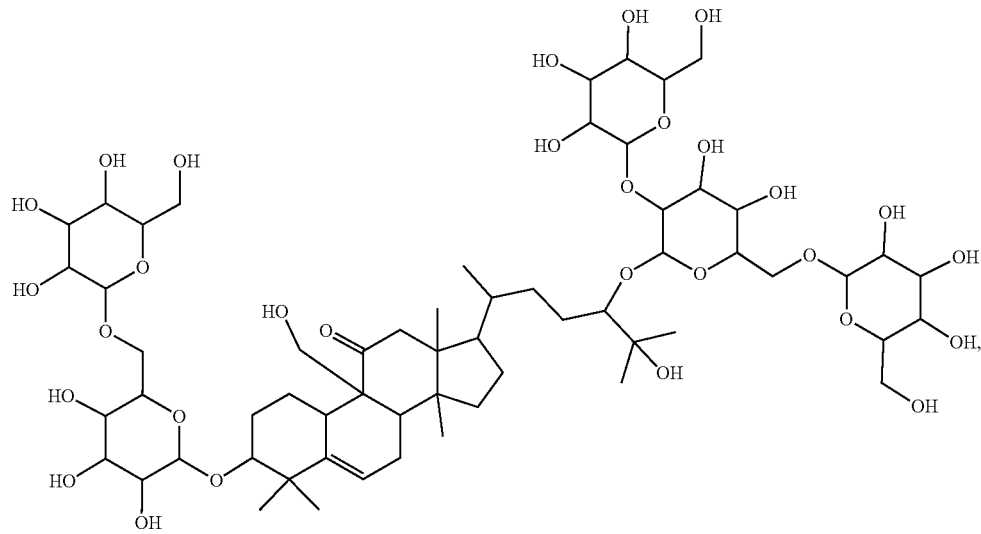 [SMILES: CC(CCC(OC1OC(COC2OC(CO)C(O)C(O)C2O)C(O)C(O)C1OC1OC(CO)C(O)C(O)C1O)C(C)(C)O)C1CCC2(C)C3CC=C4C(CCC(OC5OC(COC6OC(CO)C(O)C(O)C6O)C(O)C(O)C5O)C4(C)C)C3(CO)C(=O)CC12C]

also referred to herein as 1-[(6-O-hexopyranosylhexopyranosyl)oxy]-25-hydroxy-9-(hydroxymethyl)-10,14-dimethyl-11-oxo-4,9-cyclo-9,10-secocholest-5-en-24-yl hexopyranosyl-(1→2)-[hexopyranosyl-(1→6)]hexopyranoside (Compound 5).

In a further embodiment, the mogroside compound is a compound of the formula:

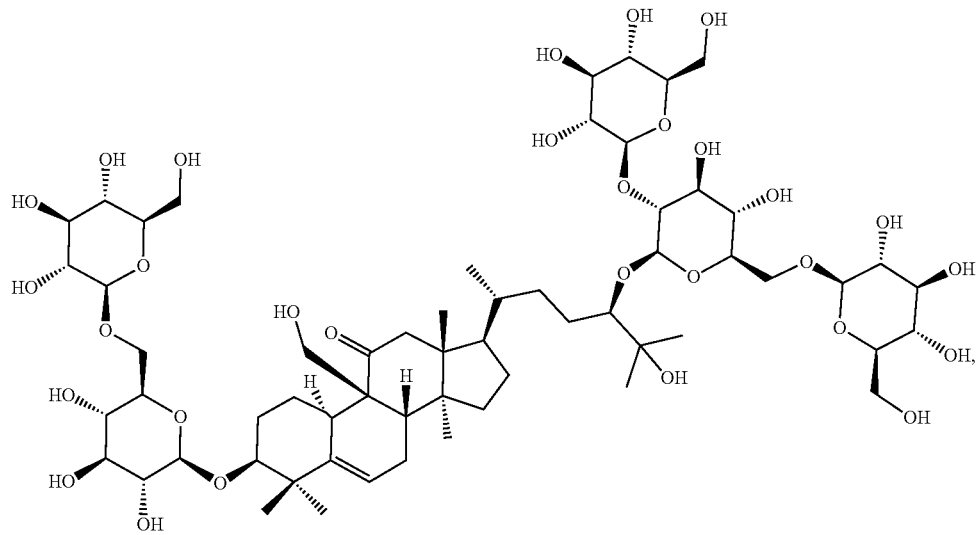

also referred to herein as (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a).

In some embodiments, the mogroside compound is a compound of the formula:

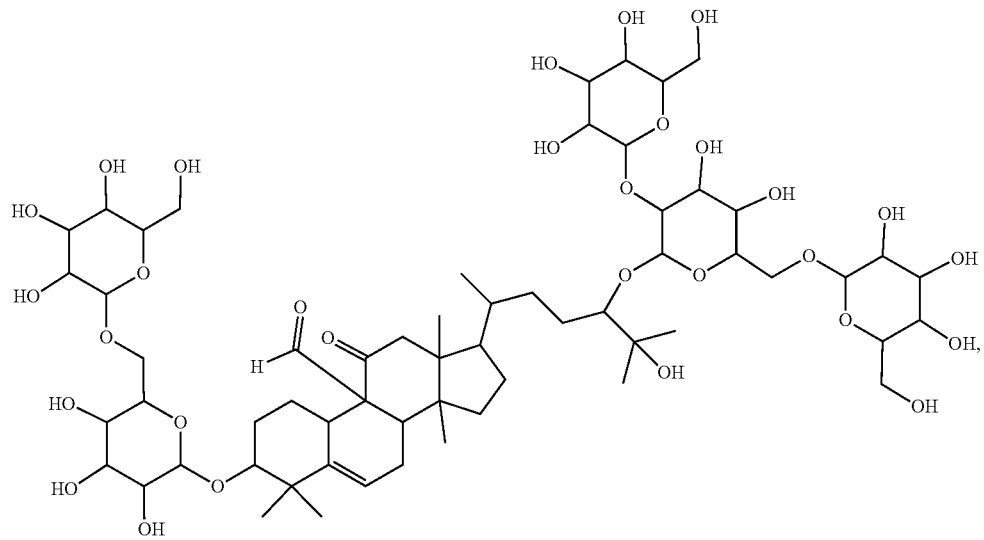 [SMILES: CC(CCC(OC1OC(COC2OC(CO)C(O)C(O)C2O)C(O)C(O)C1OC1OC(CO)C(O)C(O)C1O)C(C)(C)O)C1CCC2(C)C3CC=C4C(CCC(OC5OC(COC6OC(CO)C(O)C(O)C6O)C(O)C(O)C5O)C4(C)C)C3(C=O)C(=O)CC12C]

also referred to herein as 9-formyl-1-[(6-O-hexopyranosyl-hexopyranosyl)oxy]-25-hydroxy-10,14-dimethyl-11-oxo-4,9-cyclo-9,10-secocholest-5-en-24-yl hexopyranosyl-(1→2)-[hexopyranosyl-(1→6)]hexopyranoside (Compound 6).

In a further embodiment, the mogroside compound is a compound of the formula:

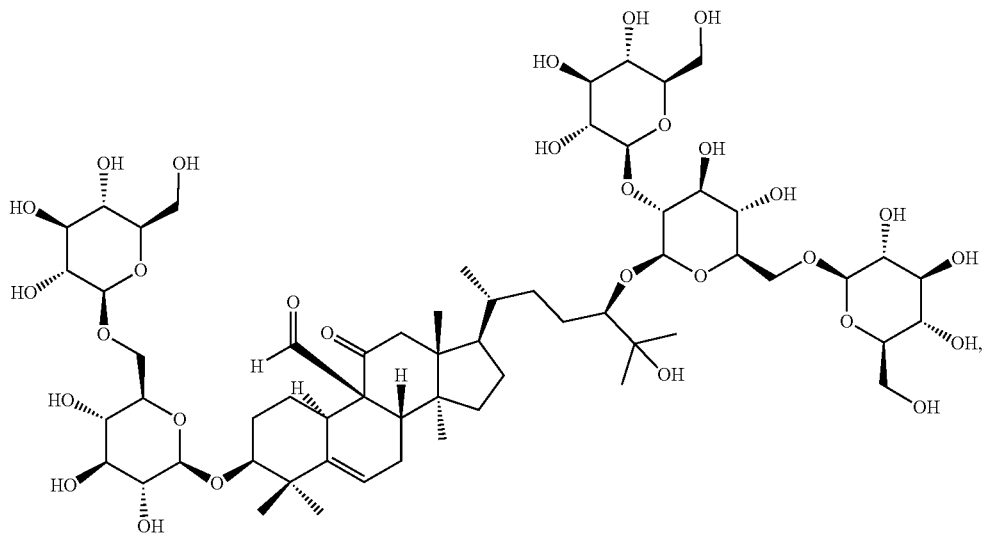

also referred to herein as (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a).

In some embodiments, the mogroside compound is a compound of the formula:

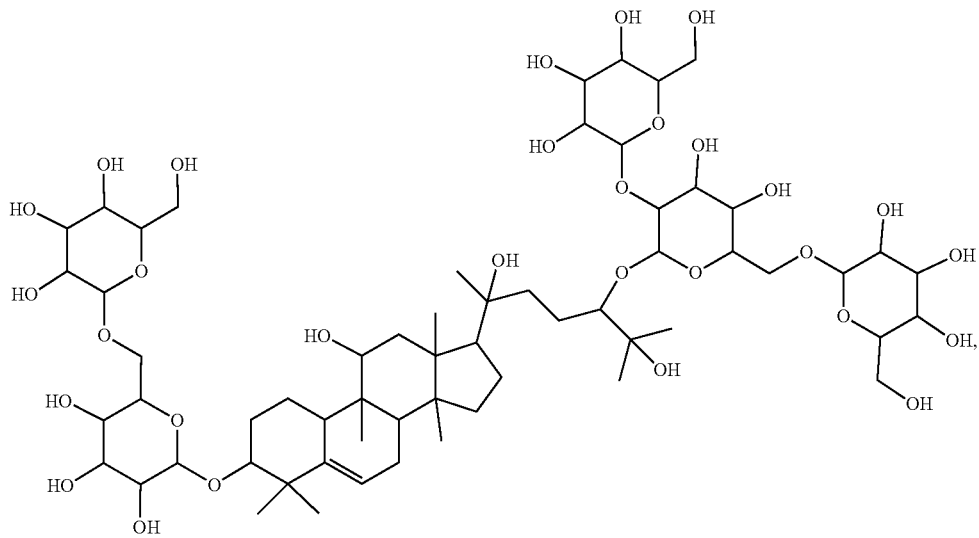

also referred to herein as 1-[(6-O-hexopyranosylhexopyranosyl)oxy]-11,20,25-trihydroxy-9,10,14-trimethyl-4,9-cyclo-9,10-secocholest-5-en-24-yl hexopyranosyl-(1→2)-[hexopyranosyl-(1→6)]hexopyranoside (Compound 7).

In a further embodiment, the mogroside compound is a compound of the formula:

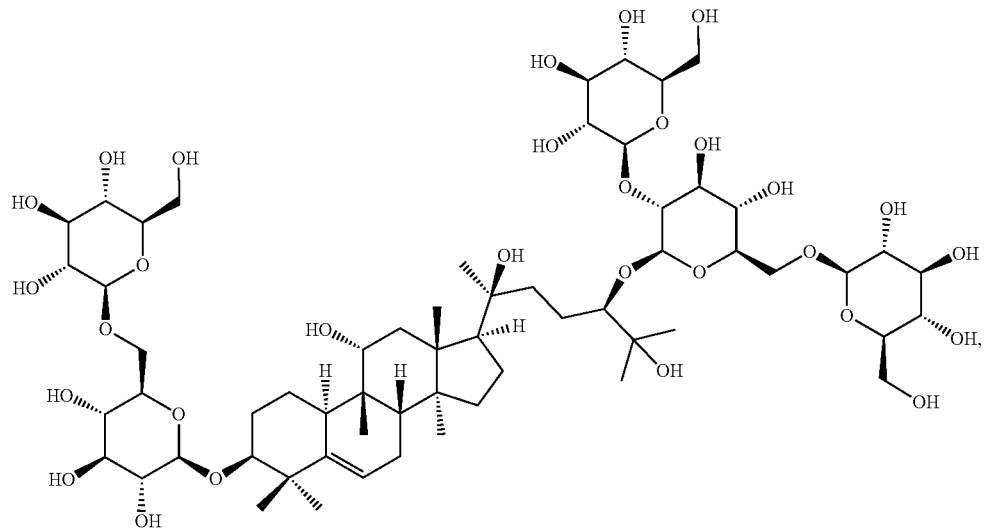

also referred to herein as (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-seco-cholest-5-en-24-yl beta-D-glucopyranosyl-(1→2)-[beta-D-glucopyranosyl-(1→6)]-beta-D-glucopyranoside (20-hydroxy-mogroside V, Compound 7a).

In some embodiments, the mogroside compound is a compound of the formula:

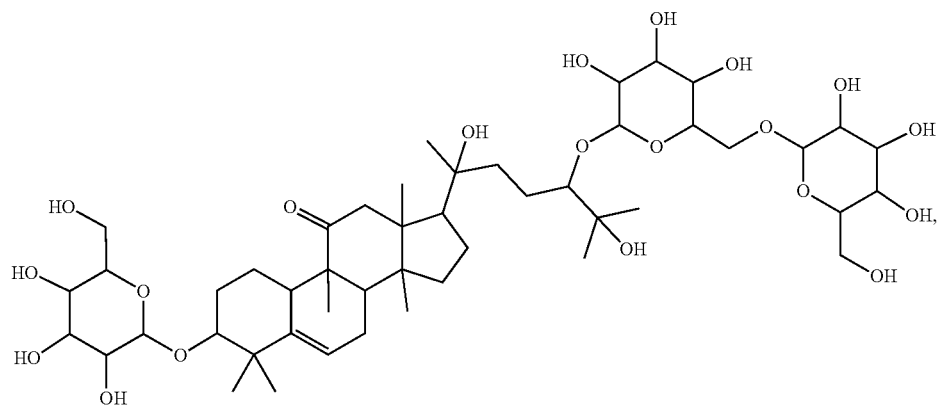

also referred to herein as 1-(hexopyranosyloxy)-20,25-dihydroxy-9,10,14-trimethyl-11-oxo-4,9-cyclo-9,10-seco-cholest-5-en-24-yl 6-O-hexopyranosylhexopyranoside (Compound 8).

In a further embodiment, the mogroside compound is a compound of the formula:

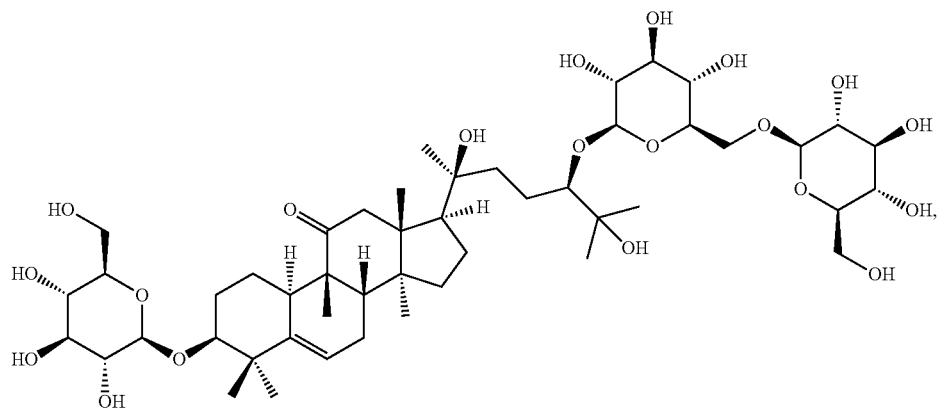

also referred to herein as (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a).

In some embodiments. the mogroside compound is a compound of the formula:

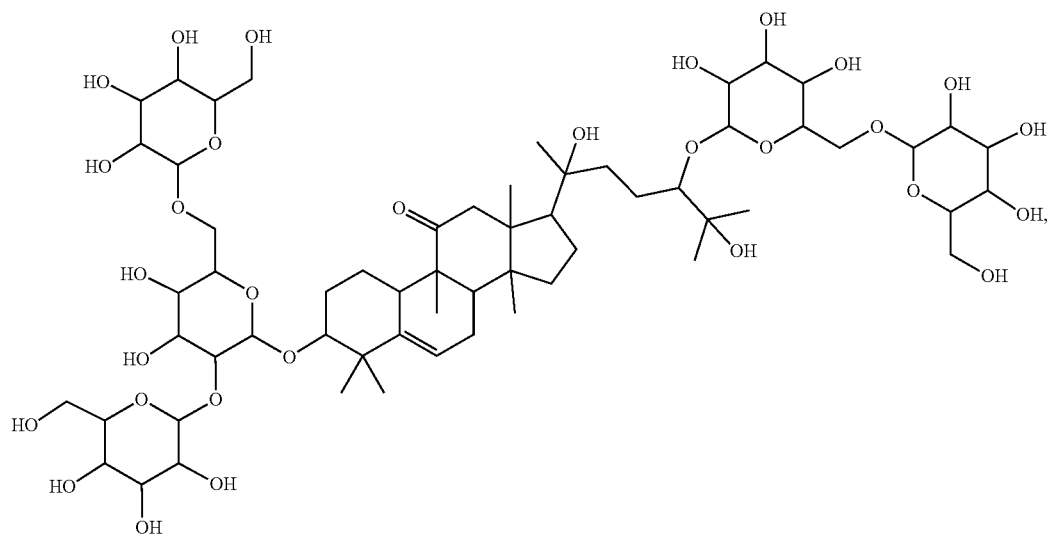

also referred to herein as 24-[(6-O-hexopyranosylhexopyranosyl)oxy]-20,25-dihydroxy-9,10,14-trimethyl-11-oxo-4,9-cyclo-9,10-secocholest-5-en-1-yl hexopyranosyl-(1→2)-[hexopyranosyl-(1→6)]hexopyranoside (Compound 9).

In a further embodiment, the mogroside compound is a compound of the formula:

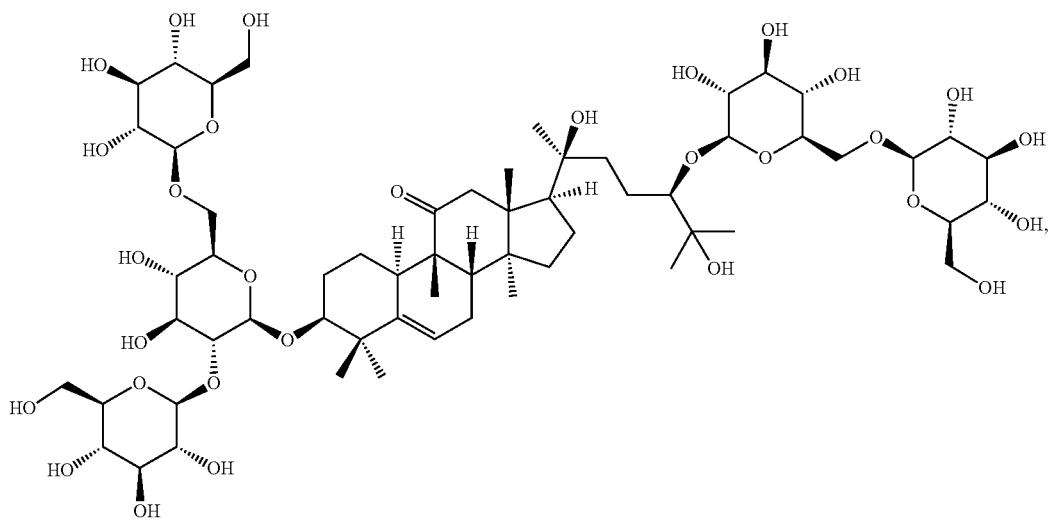

also referred to herein as (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a).

In some embodiments, the mogroside compound is a compound of the formula:

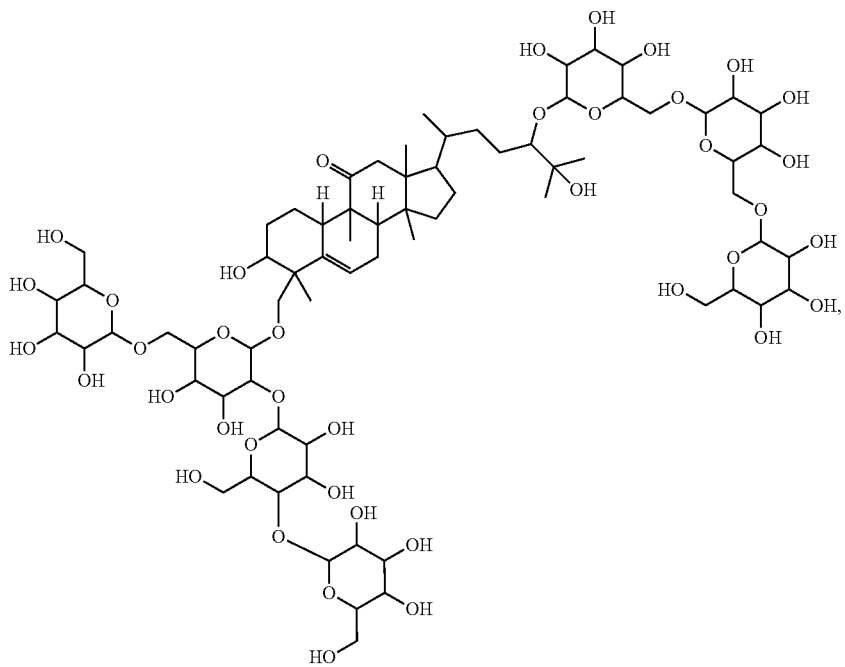

also referred to herein as (24-{[hexopyranosyl-(1→6)hexopyranosyl-(1→6)hexopyranosyl]-oxy}-1,25-dihydroxy-9,14-dimethyl-11-oxo-4,9-cyclo-9,10-secocholest-5-en-10-yl)methyl hexopyranosyl-(1→6)-[hexopyranosyl-(1→4)hexopyranosyl-(1→2)]hexopyranoside (Compound 10).

In a further embodiment, the mogroside compound is a compound of the formula:

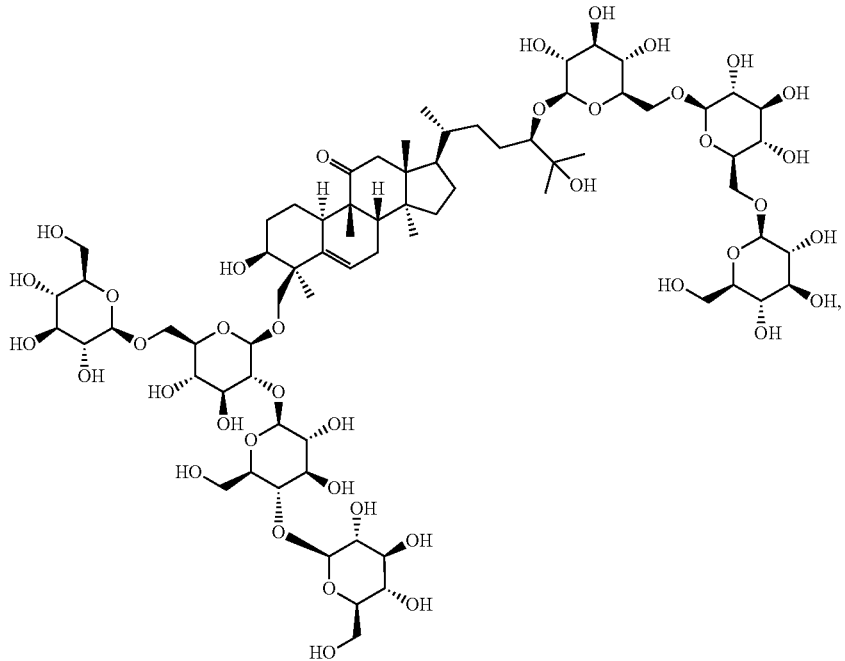

also referred to herein as [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl] methyl beta-D-glucopyranosyl-(1→6)-[beta-D-glucopyranosyl-(1→4)-beta-D-glucopyranosyl-(1→2)]-beta-D-glucopyranoside (Compound 10a).

In one embodiments, the mogroside compound is: 1-[(6-O-hexopyranosyl-hexopyranosyl)oxy]-11,25-dihydroxy-9,10,14-trimethyl-4,9-cyclo-9,10-secocholest-5-en-24-yl hexopyranosyl-(1→6)-[hexopyranosyl-(1→4)hexopyranosyl-(1→2)]hexopyranoside (Compound 12), 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→2)-[hexopyranosyl-(1→6)hexopyranosyl-(1→6)]hexopyranoside (Compound 13), 1-{[hexopyranosyl-(1→2)-[hexopyranosyl-(1→6)]hexopyranosyl]oxy}-11,25-dihydroxy-9,10,14-trimethyl-4,9-cyclo-9,10-secocholest-5-en-24-yl hexopyranosyl-(1→2)-[hexopyranosyl-(1→6)]hexopyranoside (Compound 14), and 1-[(6-O-hexopyranosylhexopyranosyl)oxy]-25-hydroxy-9,10,14-trimethyl-4,9-cyclo-9,10-secocholest-5-en-24-yl 2-O-hexopyranosylhexopyranoside (Compound 15), in the form of any one of their stereoisomers or a mixture thereof. In some further such embodiments, the mogroside compound is not compound 30 of PCT Publication No. WO 2017/075257, mogroside VI, the compound of CAS No. 2096516-62-8, or the compound of CAS No. 2096516-27-5.

In some embodiments, the mogroside compound is a compound of the formula:

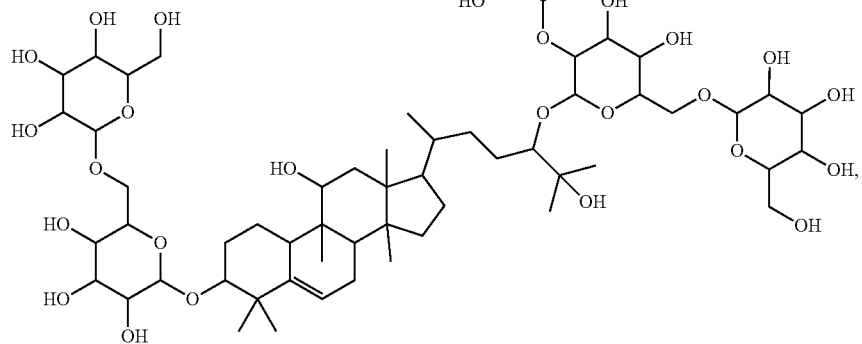

also referred to herein as 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→6)-[hexopyranosyl-(1→4)hexopyranosyl-(1→2)]hexopyranoside (Compound 12).

In a further embodiment, the mogroside compound is a compound of the formula:

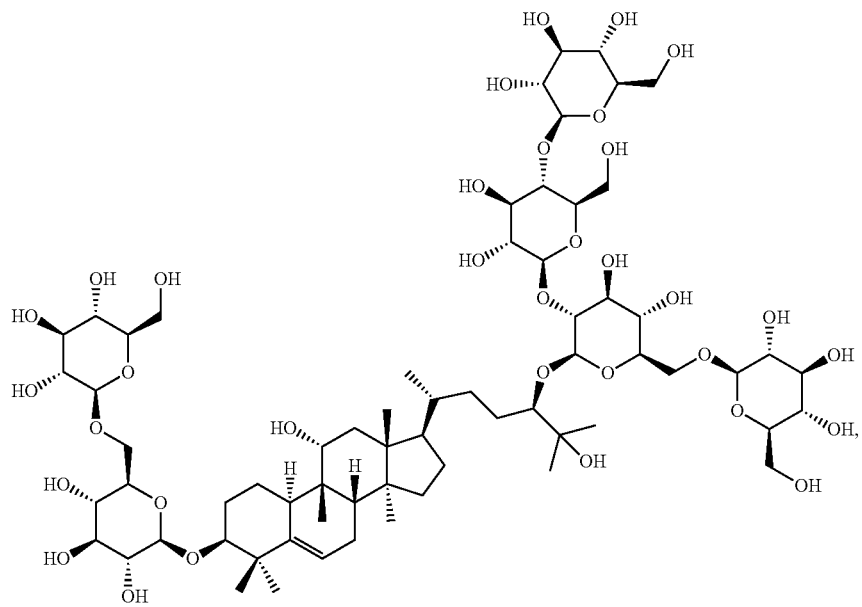

also referred to herein as (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a).

In some embodiments, the mogroside compound is a compound of the formula:

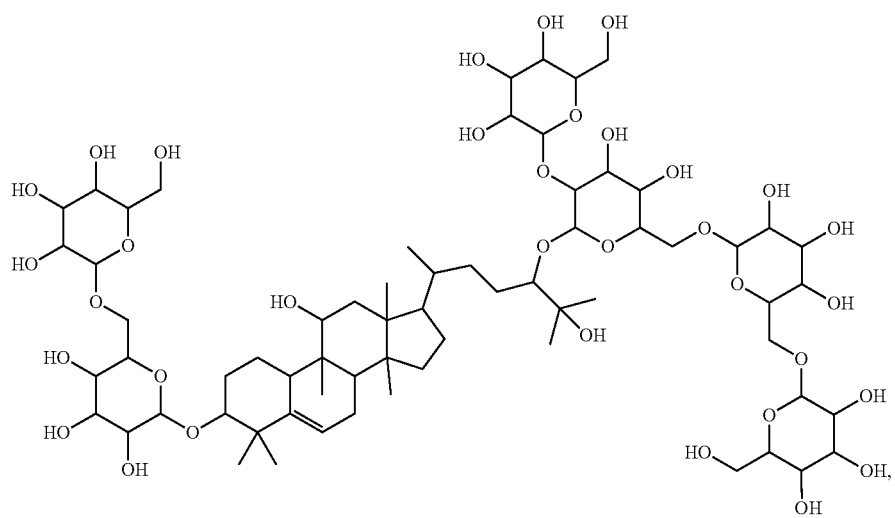

also referred to herein as 1-[(6-O-hexopyranosylhexopyranosyl)oxy]-11,25-dihydroxy-9,10,14-trimethyl-4,9-cyclo-9,10-secocholest-5-en-24-yl hexopyranosyl-(1→2)-[hexopyranosyl-(1→6)hexopyranosyl-(1→6)]hexopyranoside (Compound 13).

In a further embodiment, the mogroside compound is a compound of the formula:

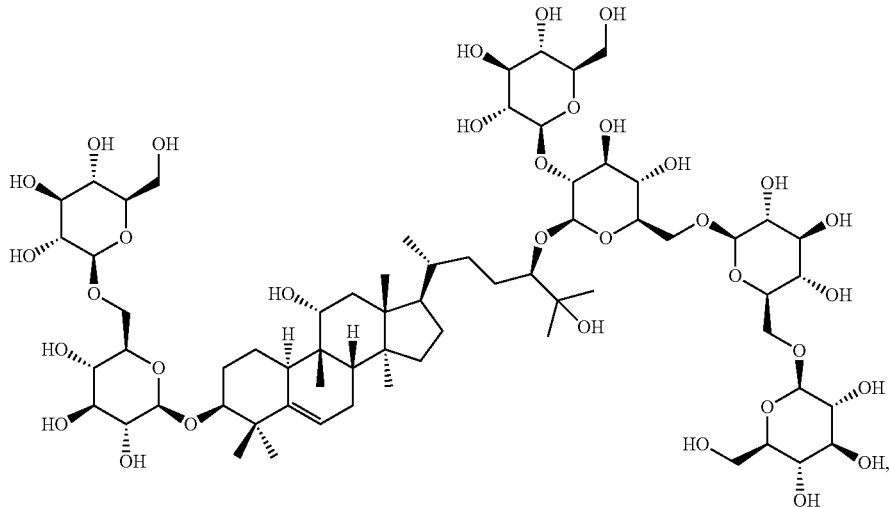

also referred to herein as (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-seco-cholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a).

In some embodiments, the mogroside compound is a compound of the formula:

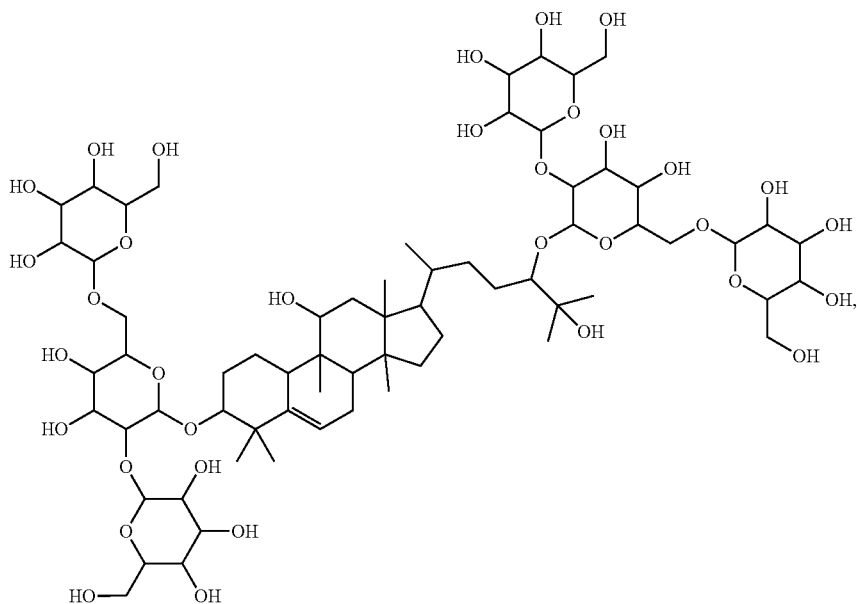

also referred to herein as 1-{[hexopyranosyl-(1→2)-[hexopyranosyl-(1→6)]hexopyranosyl]-oxy}-11,25-dihydroxy-9,10,14-trimethyl-4,9-cyclo-9,10-secocholest-5-en-24-yl hexopyranosyl-(1→2)-[hexopyranosyl-(1→6)] hexopyranoside (Compound 14).

In a further embodiment, the mogroside compound is a compound of the formula:

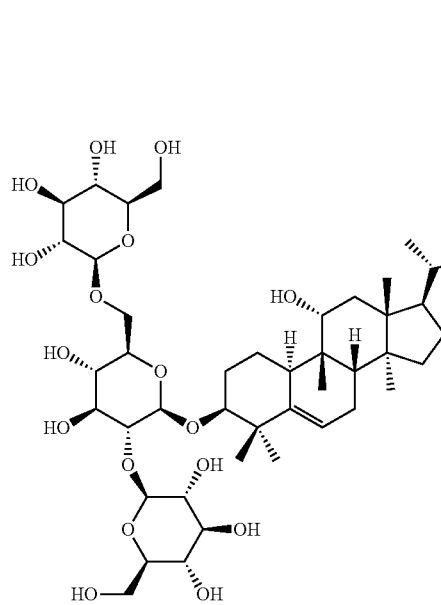
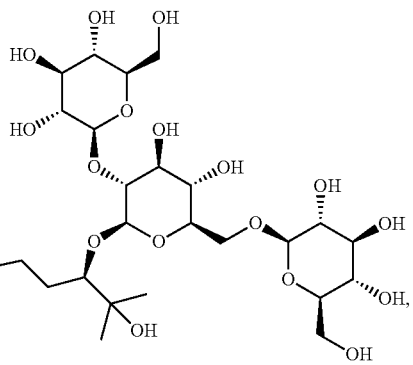

also referred to herein as (1S,4R,9beta,11beta,24R)-1-{[beta-D-glucopyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a).

In some embodiments, the mogroside compound is a compound of the formula:

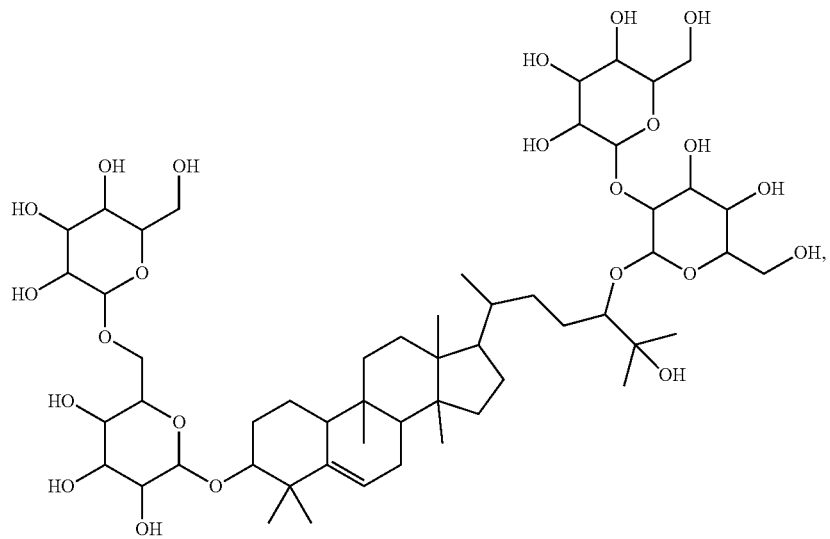

also referred to herein as 1-[(6-O-hexopyranosylhexopyranosyl)oxy]-25-hydroxy-9,10,14-trimethyl-4,9-cyclo-9,10-secocholest-5-en-24-yl 2-O-hexopyranosylhexopyranoside (Compound 15).

In a further embodiment, the mogroside compound is a compound of the formula:

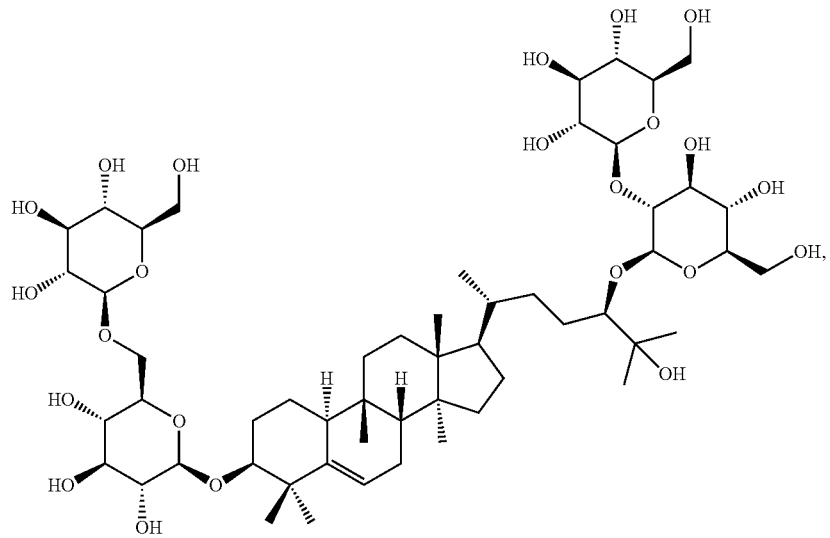

also referred to herein as (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).

Extraction of the at Least One Compound According to Some Aspects Presented Herein from Monk Fruit (*Siraitia grosvenori*)

Referring to Examples 1 to 15, the at least one compound according to an aspect presented herein may be obtained from an extract of *Siraitia grosvenori*. In some embodiments, the extract of *Siraitia grosvenori* may be first dissolved in a solvent, such as, for example, water, and the resulting solution applied to an adsorption resin.

In some embodiments, the solvent is water. In one embodiment, 60 kg of an extract of *Siraitia grosvenori* is dissolved in 150 l de-ionized water. While any extract of *Siraitia grosvenori* is suitable for use in the extraction methods disclosed herein, in one embodiment, the extract of *Siraitia grosvenori* is obtained from Gui Lin Layn Natural Ingredients Corp. In some aspects, the extract of *Siraitia grosvenori* comprises 3.5% w/w of mogroside V.

In some embodiments, the adsorption resin is an XDA macroporous resin.

In some embodiments, after the solution is applied to the adsorption resin, the resin is then eluted with a first wash of water, followed by a wash with a 5% ethanol solution, followed by a wash with a 95% ethanol solution. In some embodiments, the final elution with the 95% ethanol solution is collected and comprises the at least one compound according to an aspect presented herein.

In some embodiments, the collected elution is applied to an HPLC column. In some embodiments, the HPLC column is a C18 flash chromatography column. In some embodiments, the C18 flash chromatography column is a Daiso ODS, 40-70 μm, 100*490 mm column. In some embodiments, after application of the collected elution, the C18 flash chromatography column is eluted with water, followed by 10%, 20%, 25%, 30%, 40%, 50% ACN in water and 100% of ACN at a flow rate of 70 mL/min.

In some embodiments, where the Daiso ODS, 40-70 μm, 100*490 mm column was utilized, 16 fractions may be collected (fractions 35-50).

In one embodiment, the fraction containing the at least one compound according to an aspect presented herein is further purified, by first applying the fraction to a C18 flash chromatography column, then eluting the column with ACN. In some embodiments, the C18 flash chromatography column is a C18 flash chromatography column (e.g. Daiso ODS, 40-70 μm, 100*490 mm). In some embodiments, the column is eluted with 26% ACN in water, at a flow rate of 70 mL/min. Next, in some embodiments, the eluate is applied to a Sephadex LH-20 column (e.g. 55*1500 mm), and eluted with ACN. In some embodiments, the column is eluted with 18% ACN in water, with a flow rate of 0.3 to 1.5 mL/min. In some embodiments, the eluate from the Sephadex LH-20 column is applied to a preparative HPLC column (e.g. YMC ODS, 5 μm, 10*250 mm), and eluted with ACN, to purify the at least one compound according to an aspect presented herein. In some embodiments, the column is eluted with 14-21% ACN in water, with a flow rate of 4.5 mL/min.

Figure 2:
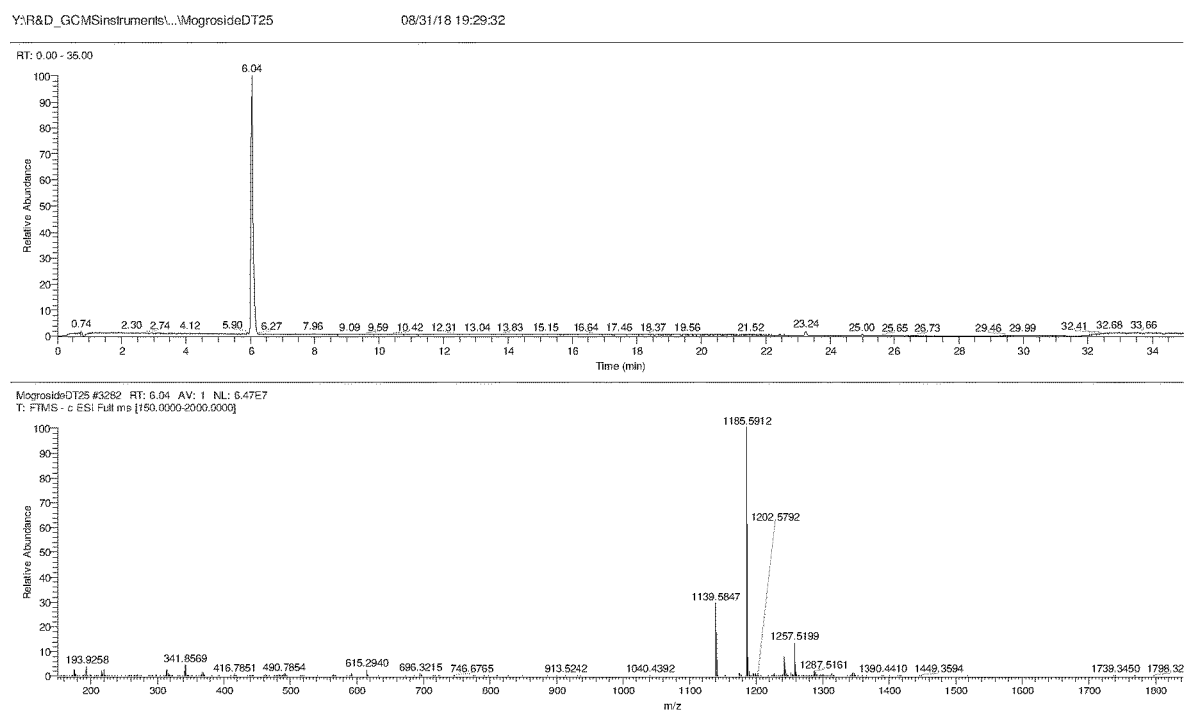
FIG. 2 shows a typical LC-HR-MS spectrograph of (1S, 4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a).
Figure 3:
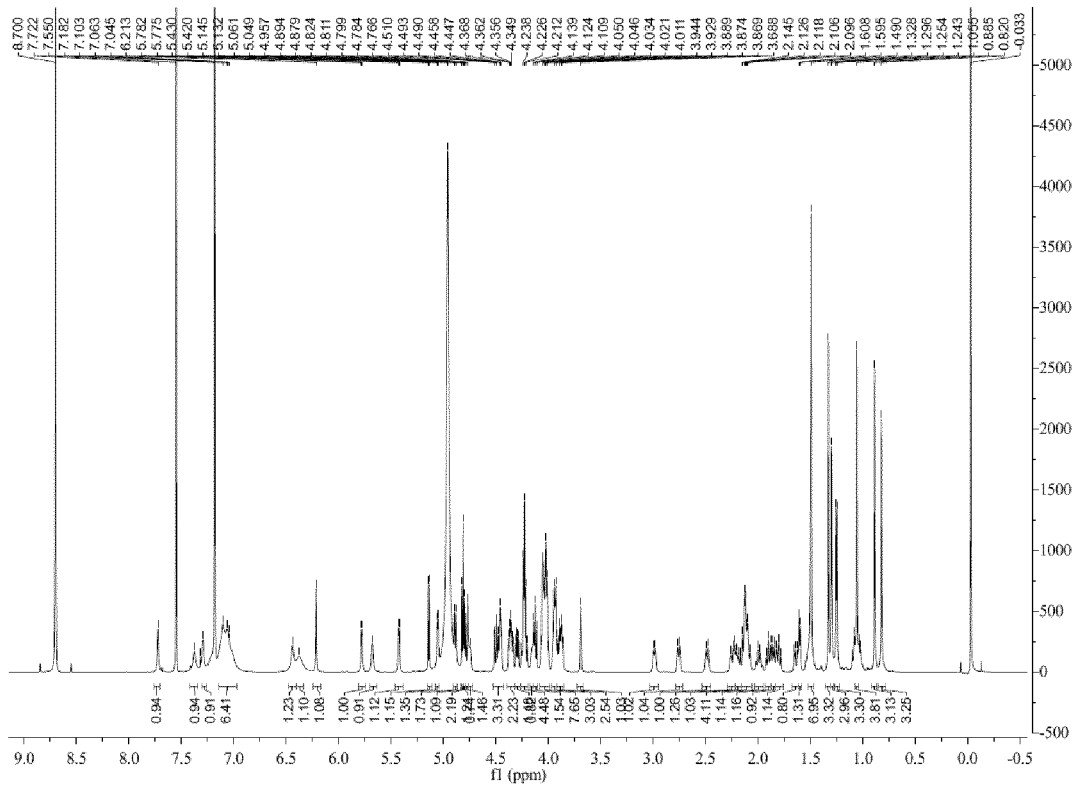
FIG. 3 shows a typical $^1$H NMR spectrograph of (1S,4R, 9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a).
Figure 4:
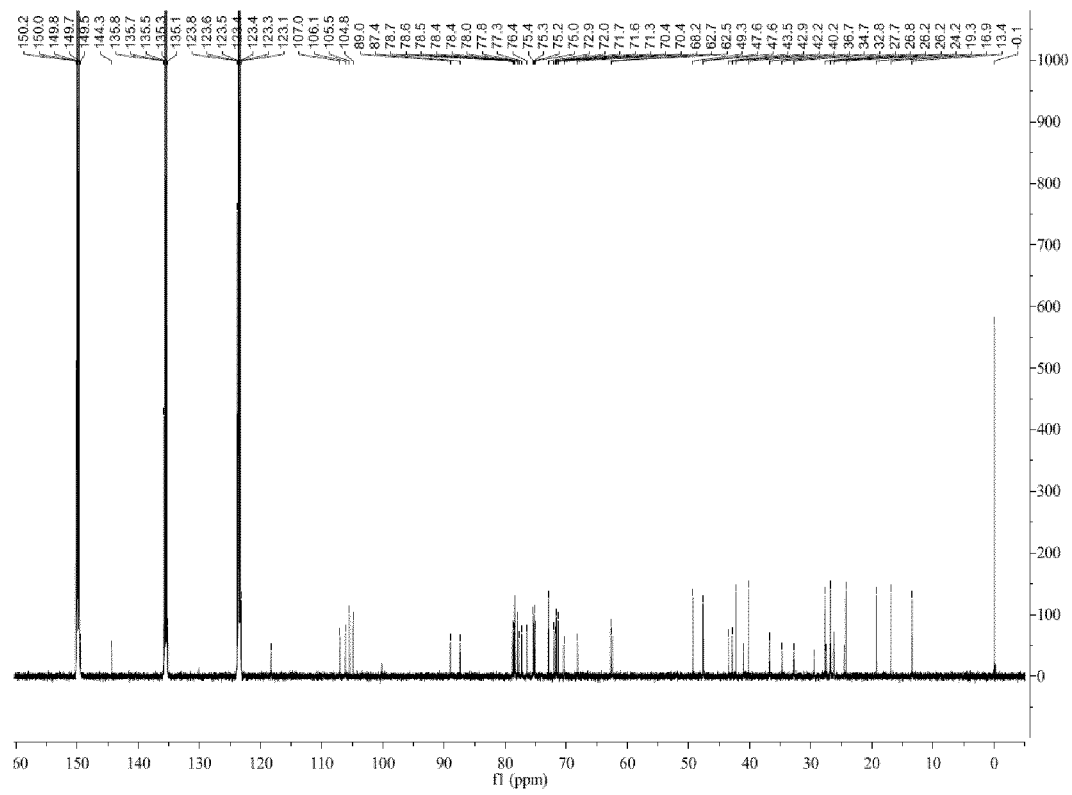
FIG. 4 shows a typical $^{13}$C NMR spectrograph of (1S, 4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a).

Referring to FIGS. 2 to 4, in some embodiments, the at least one compound according to an aspect presented herein is (1S,4R,9beta,11alpha,24R)-1-{[6-O-(beta-D-gluco-pyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a).

Figure 5:
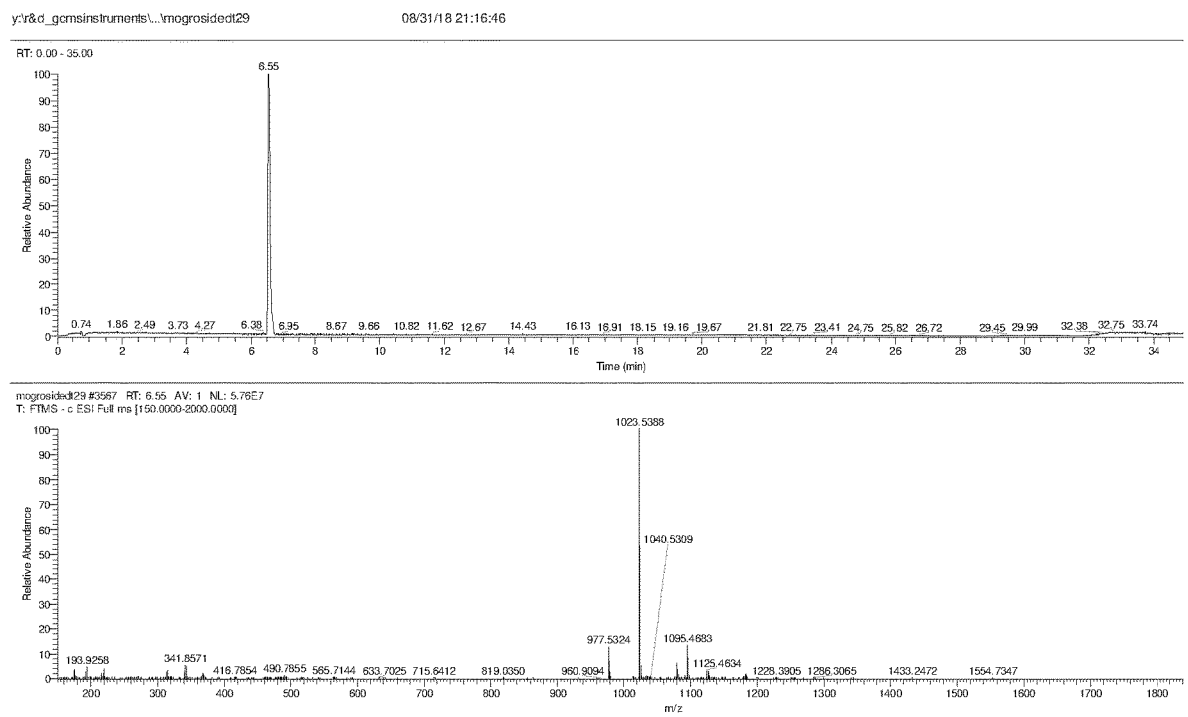
FIG. 5 shows a typical LC-HR-MS spectrograph of (1S, 4R,9beta,11alpha,24R)-1-(beta-D-glucopyranosyloxy)-11, 22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a).
Figure 6:
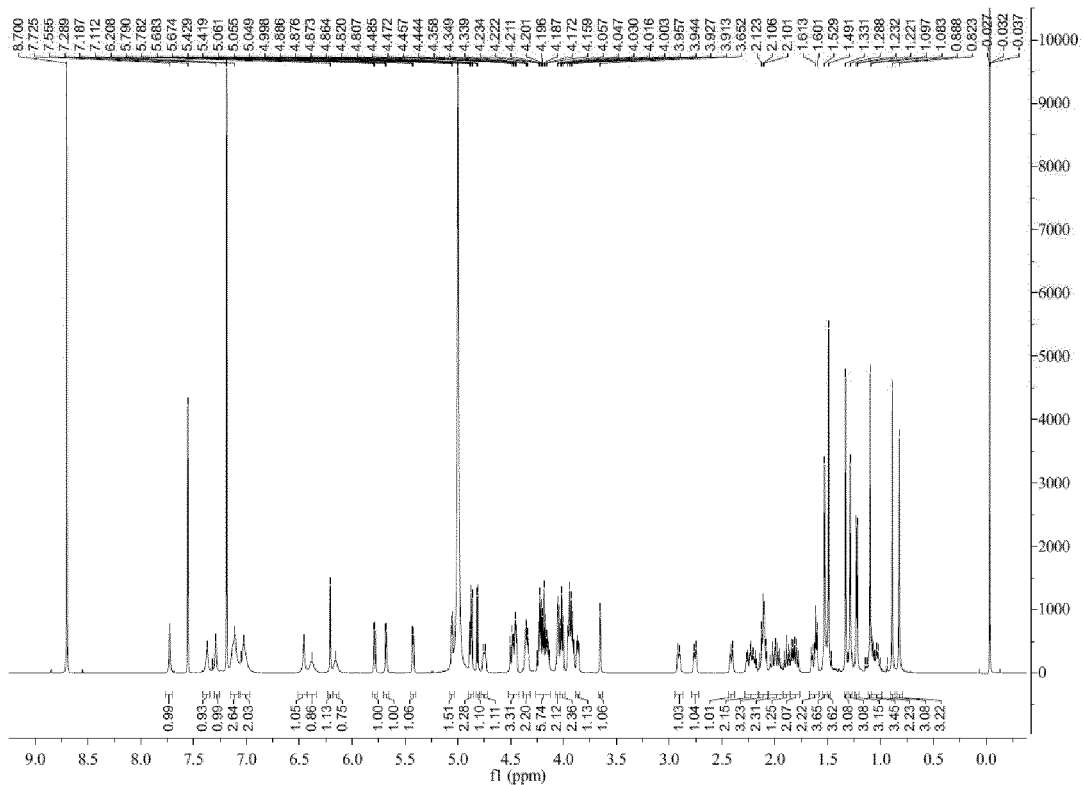
FIG. 6 shows a typical $^1$H NMR spectrograph of (1S,4R, 9beta,11alpha,24R)-1-(beta-D-glucopyranosyloxy)-11,22, 25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a).
Figure 7:
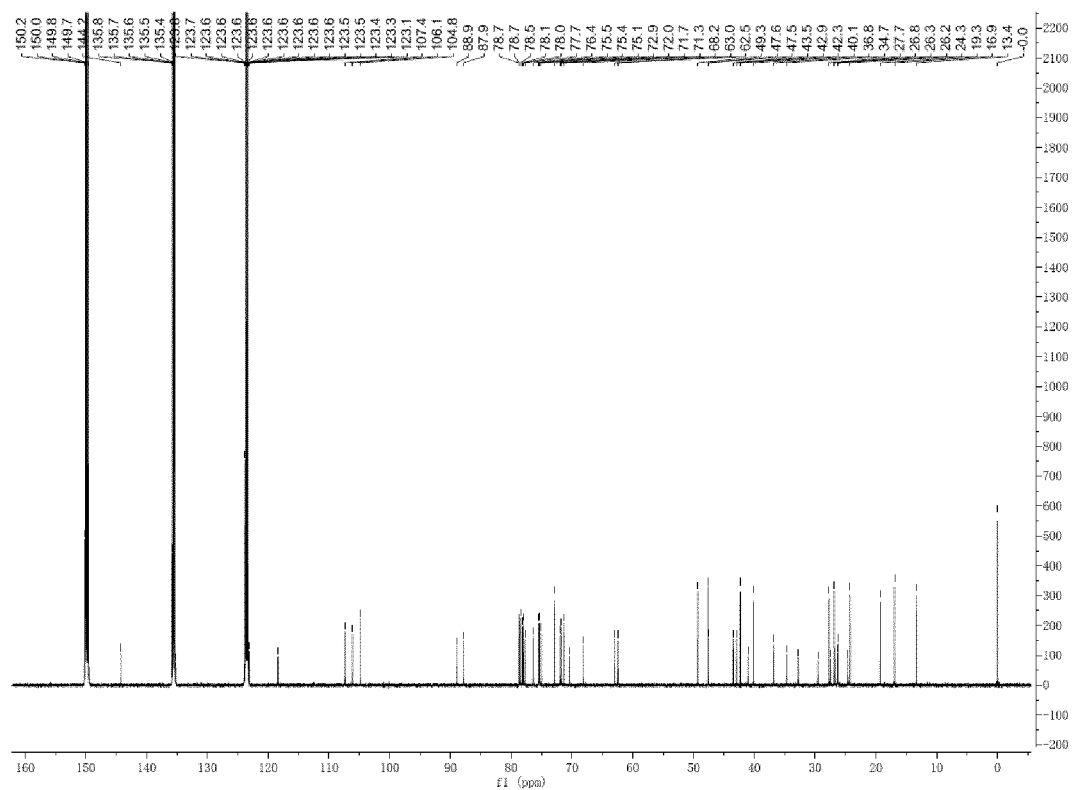
FIG. 7 shows a typical $^{13}$C NMR spectrograph of (1S,4R,9beta,11alpha,24R)-1-(beta-D-glucopyranosyloxy)-11,22,25-trihydroxy-9,10,14-trimethyl-4,9-cyclo-9,10-seco-cholest-5-en-24-yl 6-O-beta-D-glucopyranosyl-beta-D-glucopyranoside (22-hydroxy-mogroside III, Compound 2a).

Referring to FIGS. 5 to 7, in some embodiments, the at least one compound according to an aspect presented herein is (1S,4R,9beta,11alpha,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a).

Figure 8:
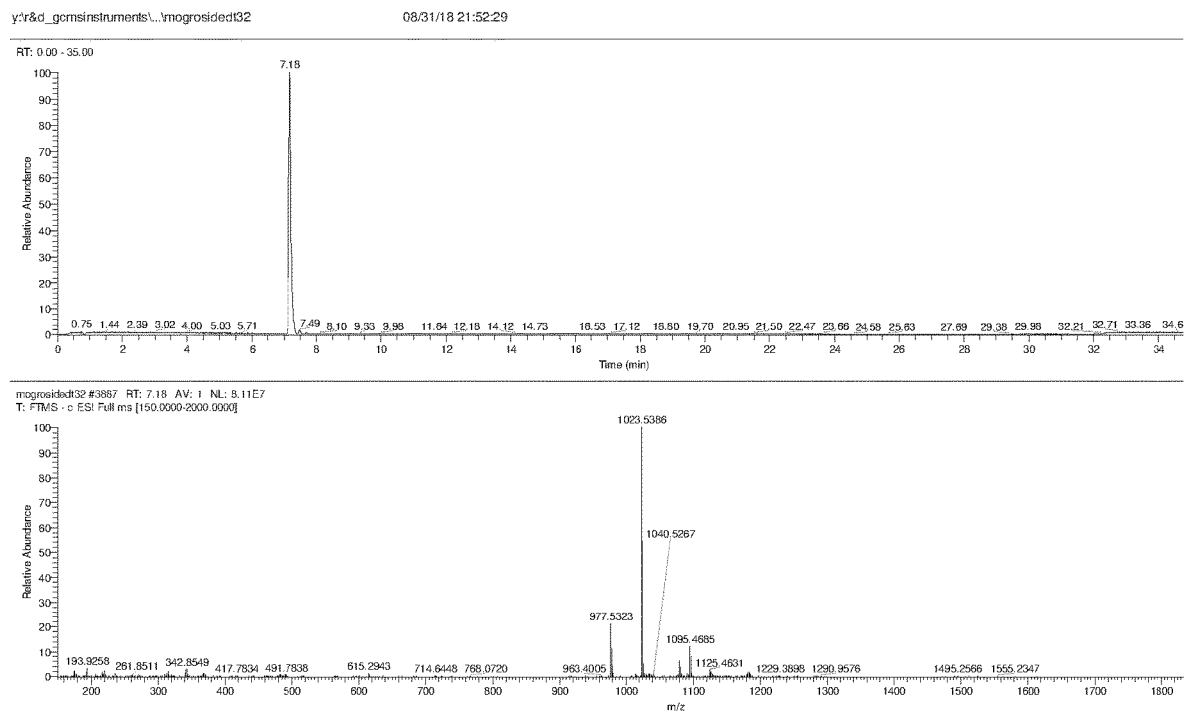
FIG. 8 shows a typical LC-HR-MS spectrograph of (1S,4R,9beta,11beta,24R)-1-(beta-D-glucopyranosyloxy)-11,22,25-trihydroxy-9,10,14-trimethyl-4,9-cyclo-9,10-seco-cholest-5-en-24-yl 6-O-beta-D-glucopyranosyl-beta-D-glucopyranoside (22-hydroxy-11-epi-mogroside III, Compound 2b).
Figure 9:
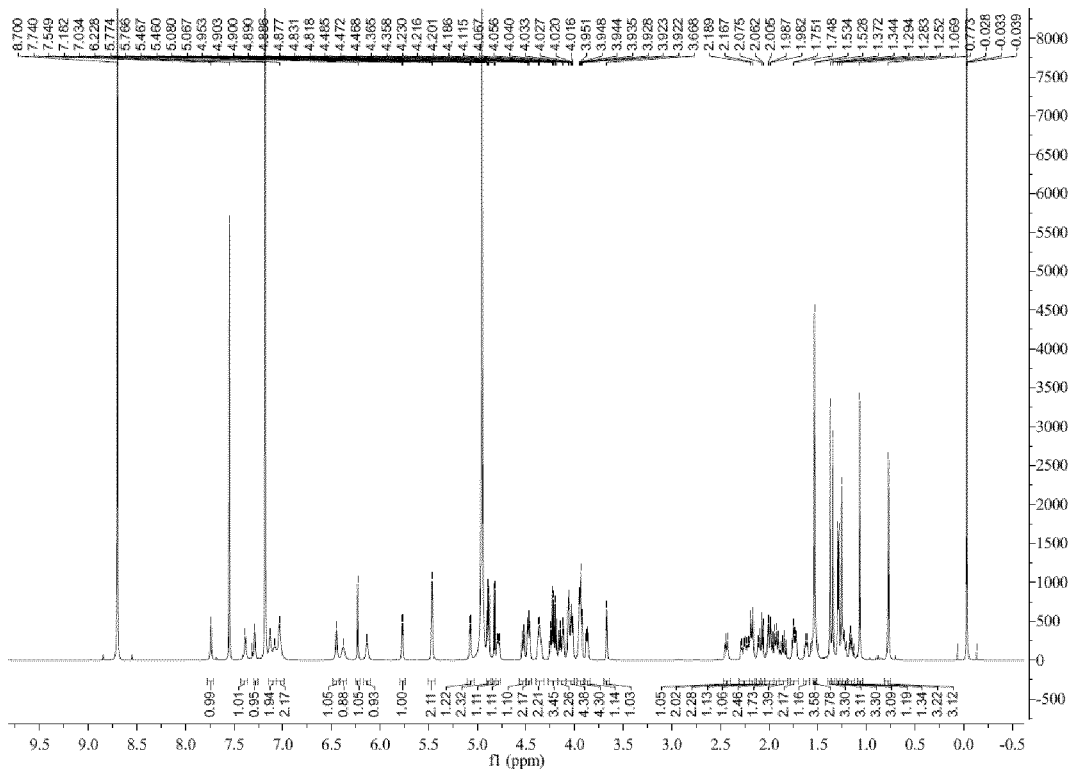
FIG. 9 shows a typical $^1$H NMR spectrograph of (1S,4R,9beta,11beta,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b).
Figure 10:
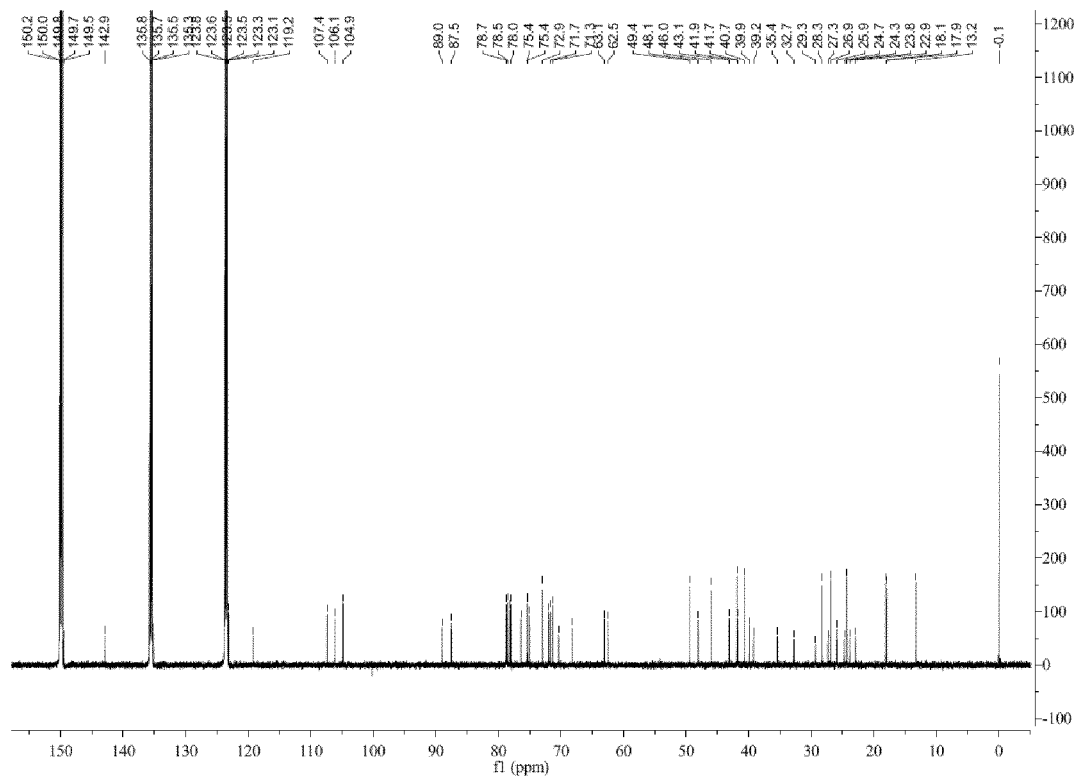
FIG. 10 shows a typical $^{13}$C NMR spectrograph of (1S,4R,9beta,11beta,24R)-1-(beta-D-glucopyranosyloxy)-11,22,25-trihydroxy-9,10,14-trimethyl-4,9-cyclo-9,10-seco-cholest-5-en-24-yl 6-O-beta-D-glucopyranosyl-beta-D-glucopyranoside (22-hydroxy-11-epi-mogroside III, Compound 2b).

Referring to FIGS. 8 to 10, in some embodiments, the at least one compound according to an aspect presented herein is (1S,4R,9beta,11beta,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b).

Figure 11:
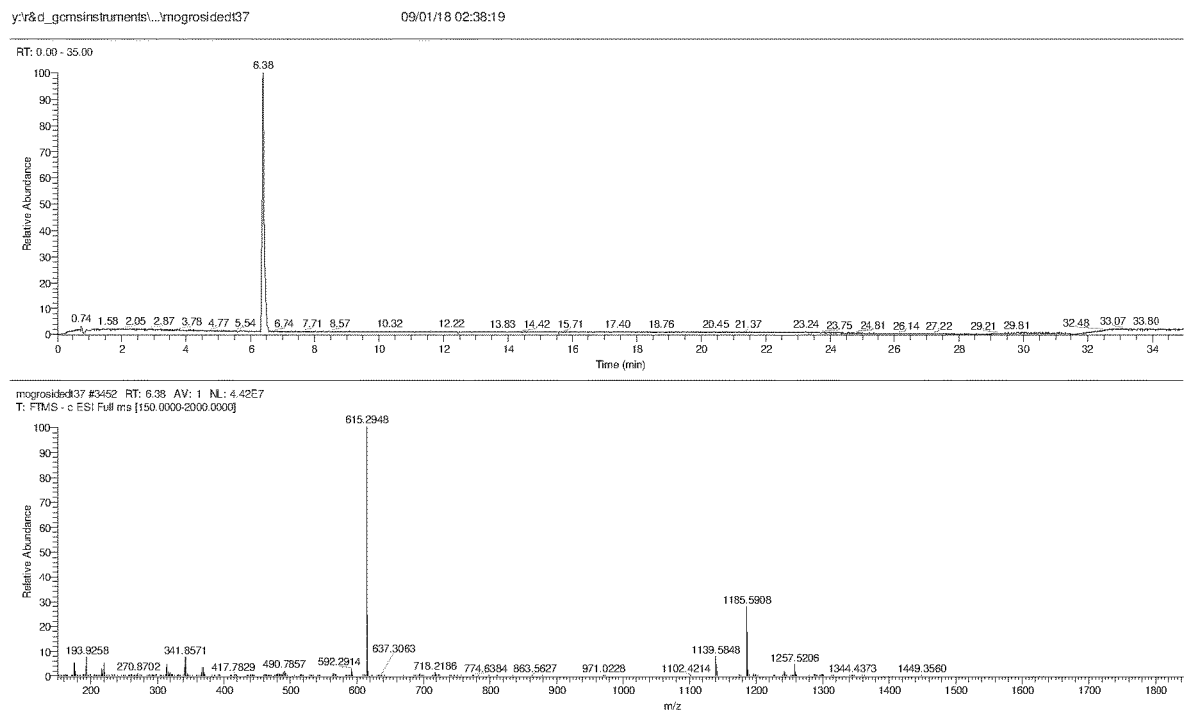
FIG. 11 shows a typical LC-HR-MS spectrograph of (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a).
Figure 12:
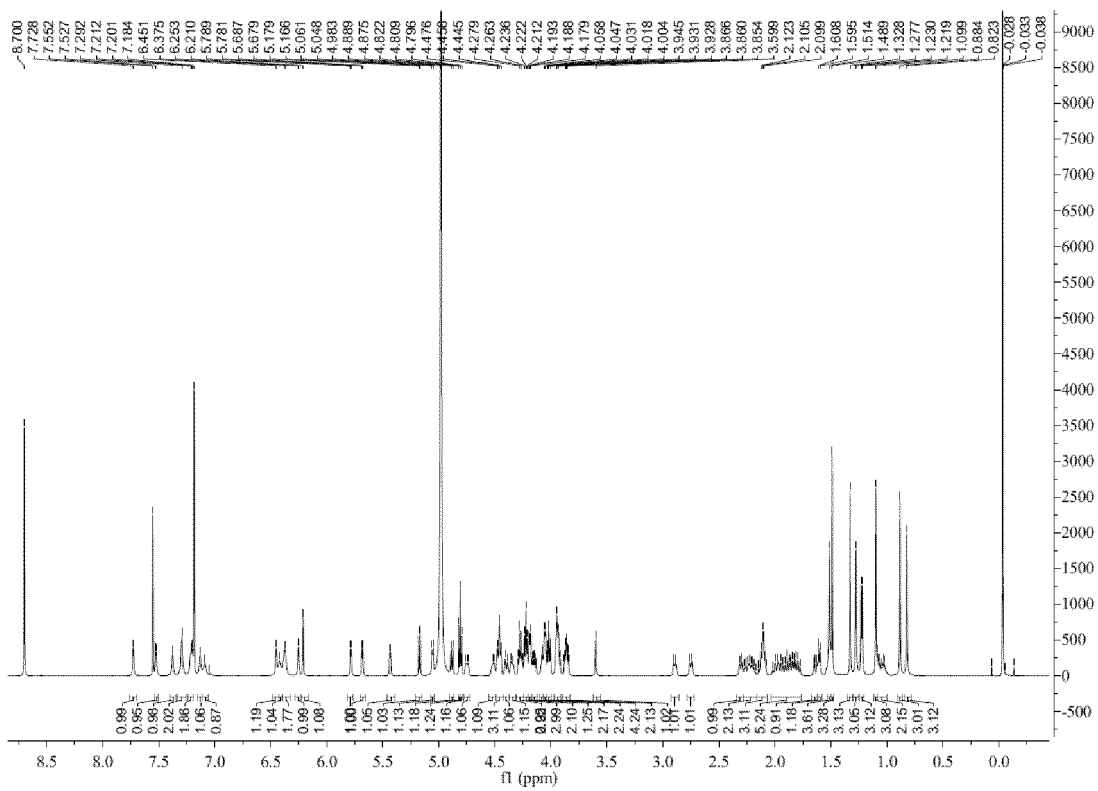
FIG. 12 shows a typical $^1$H NMR spectrograph of (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a).
Figure 13:
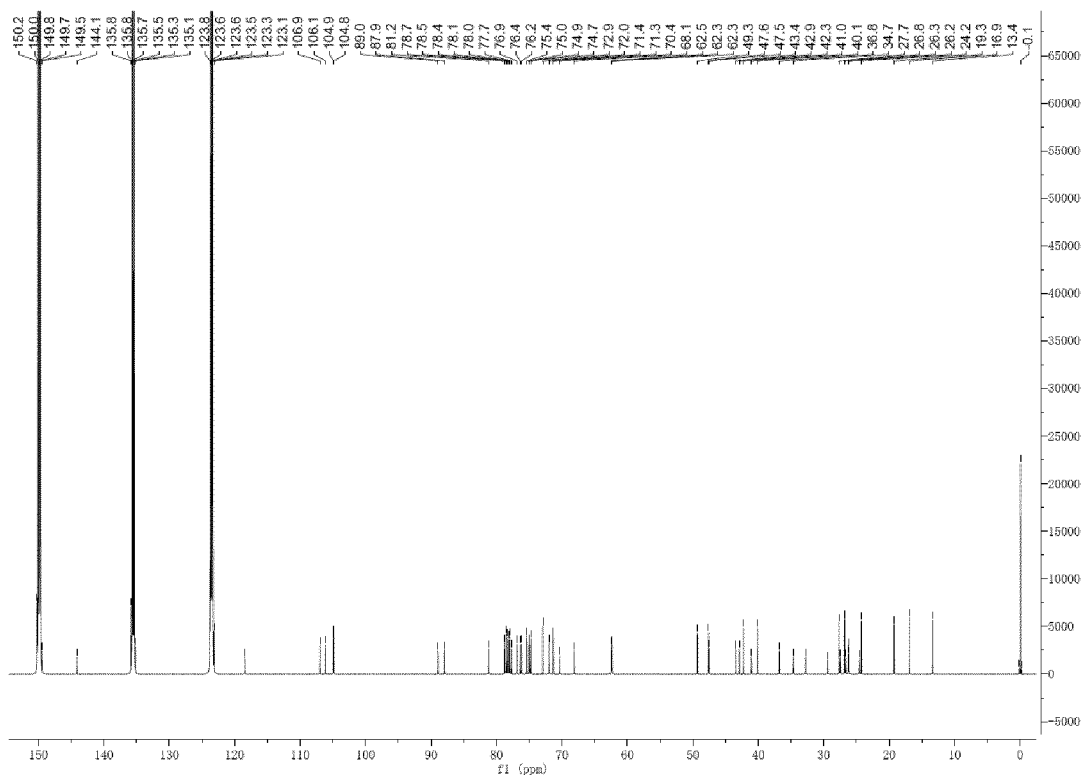
FIG. 13 shows a typical $^{13}$C NMR spectrograph of (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a).

Referring to FIGS. 11 to 13, in some embodiments, the at least one compound according to an aspect presented herein is (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a).

Figure 14:
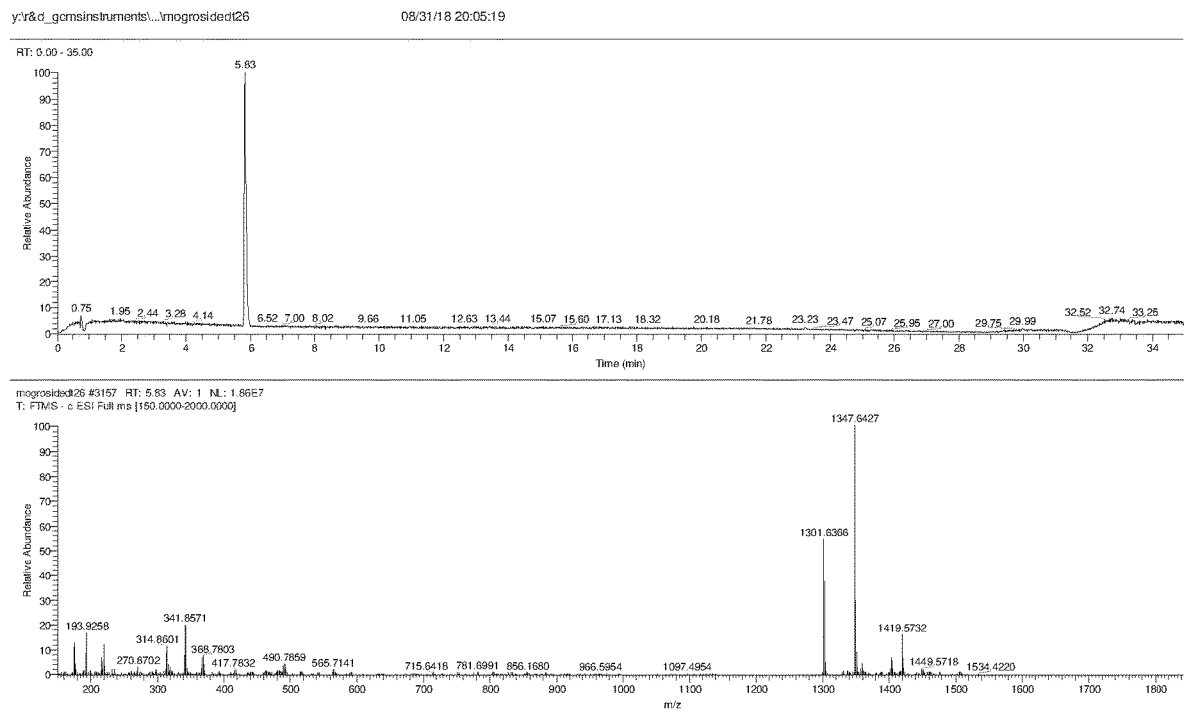
FIG. 14 shows a typical LC-HR-MS spectrograph of (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a).
Figure 15:
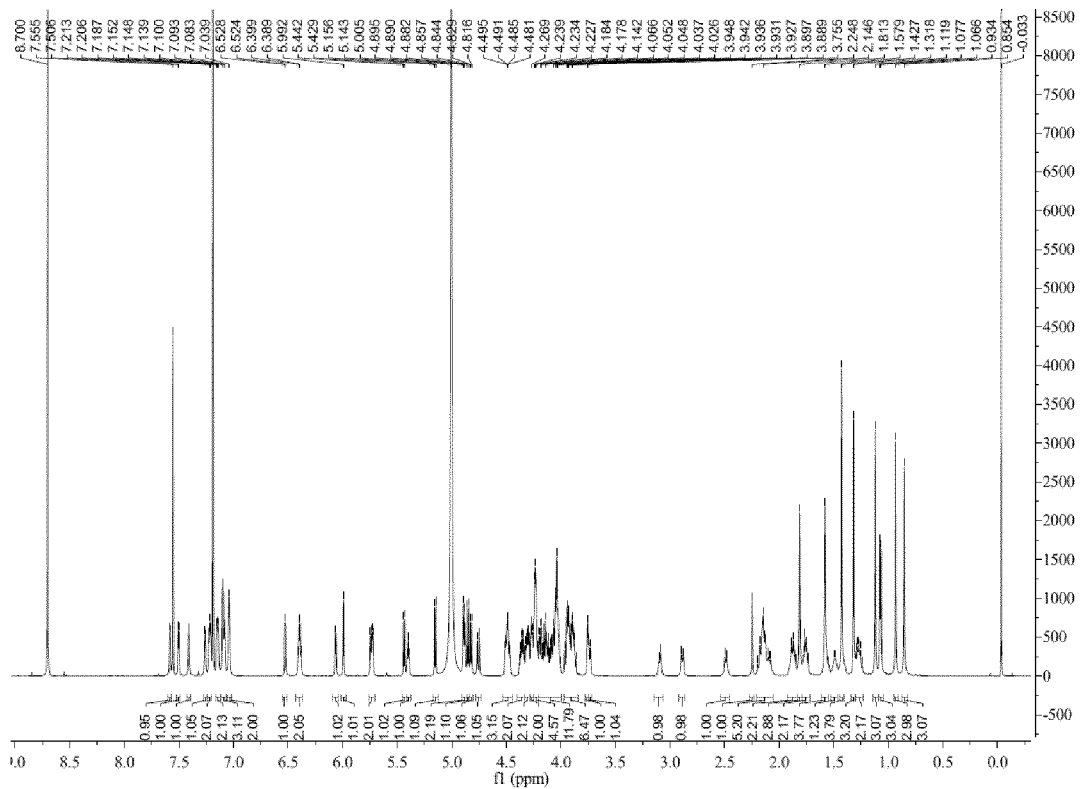
FIG. 15 shows a typical $^1$H NMR spectrograph of (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a).
Figure 16:
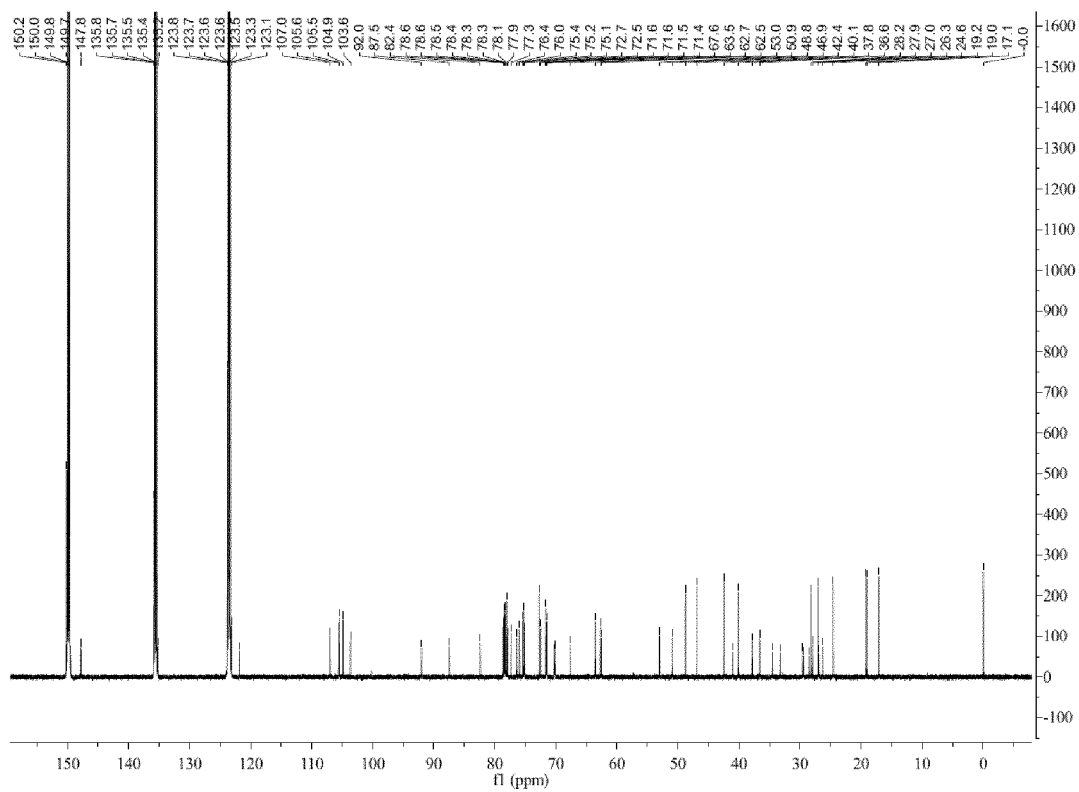
FIG. 16 shows a typical $^{13}$C NMR spectrograph of (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a).

Referring to FIGS. 14 to 16, in some embodiments, the at least one compound according to an aspect presented herein is (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1-6)]-beta-D-glucopyranoside (7-hydroxy-mogroside V, Compound 4a).

Figure 17:
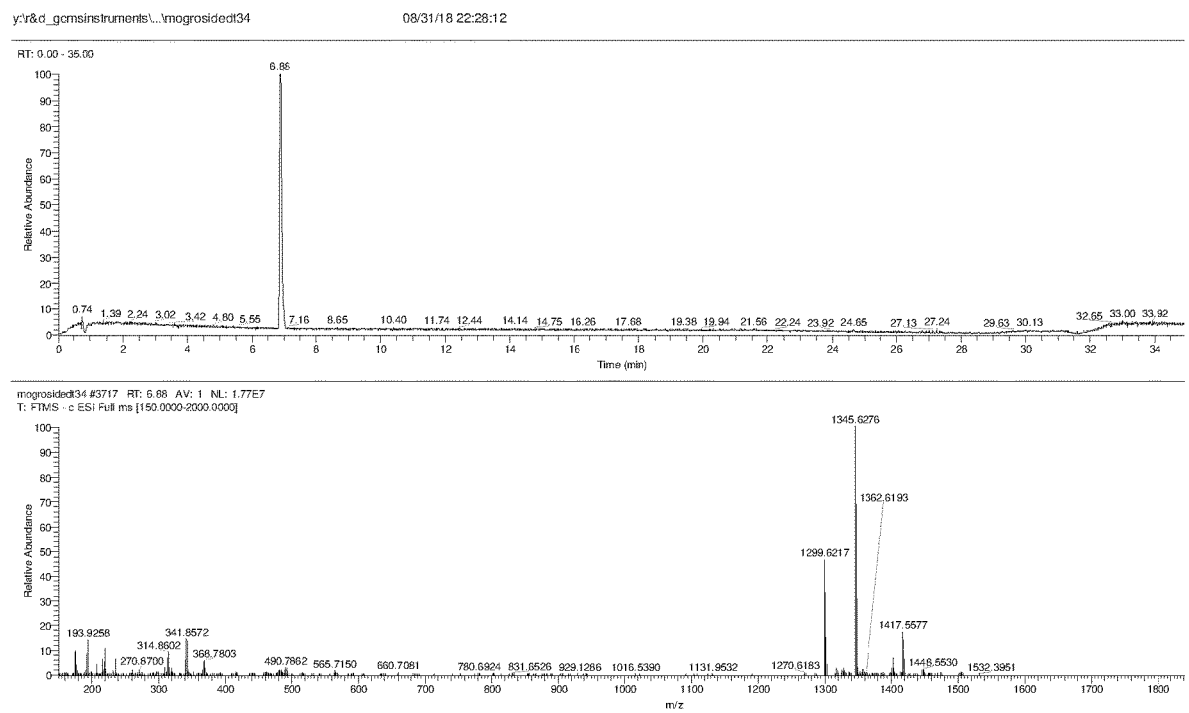
FIG. 17 shows a typical LC-HR-MS spectrograph of (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a).
Figure 18:
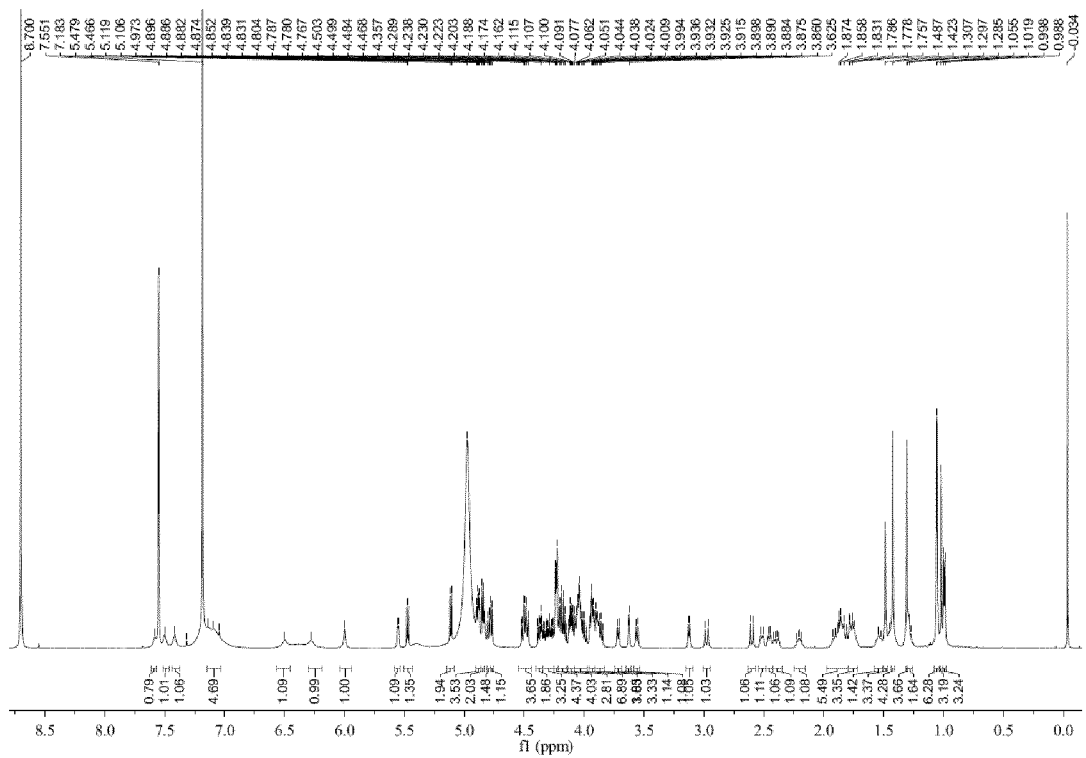
FIG. 18 shows a typical $^1$H NMR spectrograph of (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a).
Figure 19:
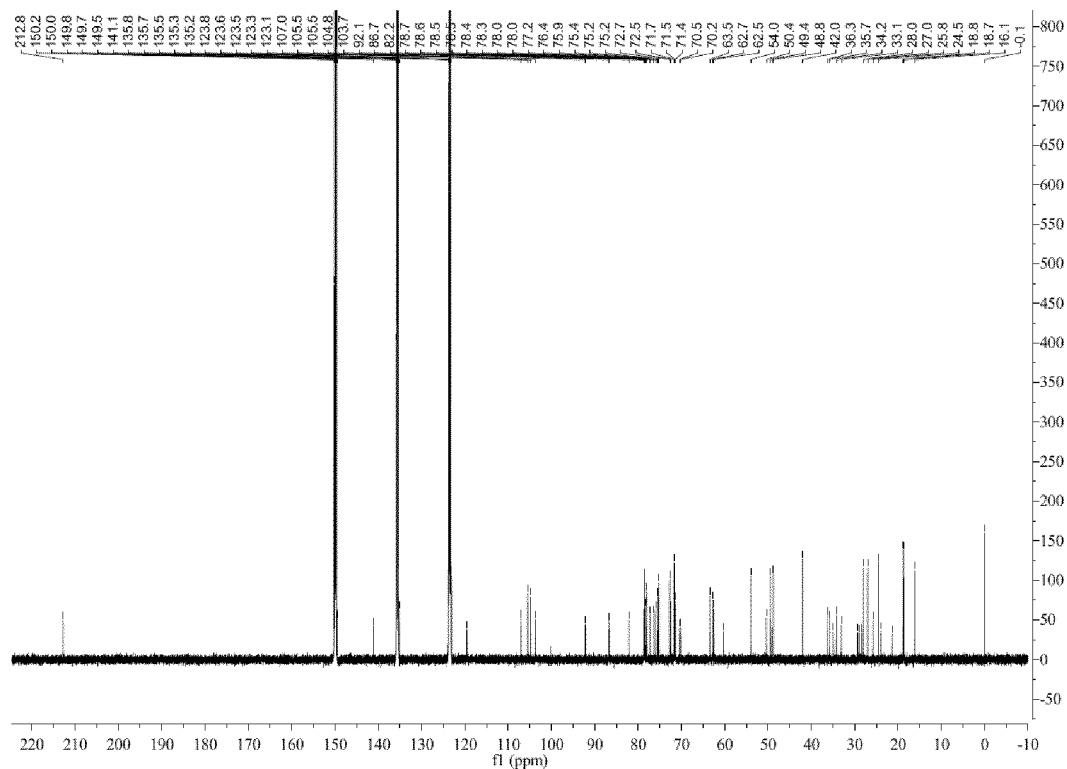
FIG. 19 shows a typical $^{13}$C NMR spectrograph of (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a).

Referring to FIGS. 17 to 19, in some embodiments, the at least one compound according to an aspect presented herein is (1S,4R,9beta,24R)-1-{[6-O-(beta-D-gluco-pyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a).

Figure 20:
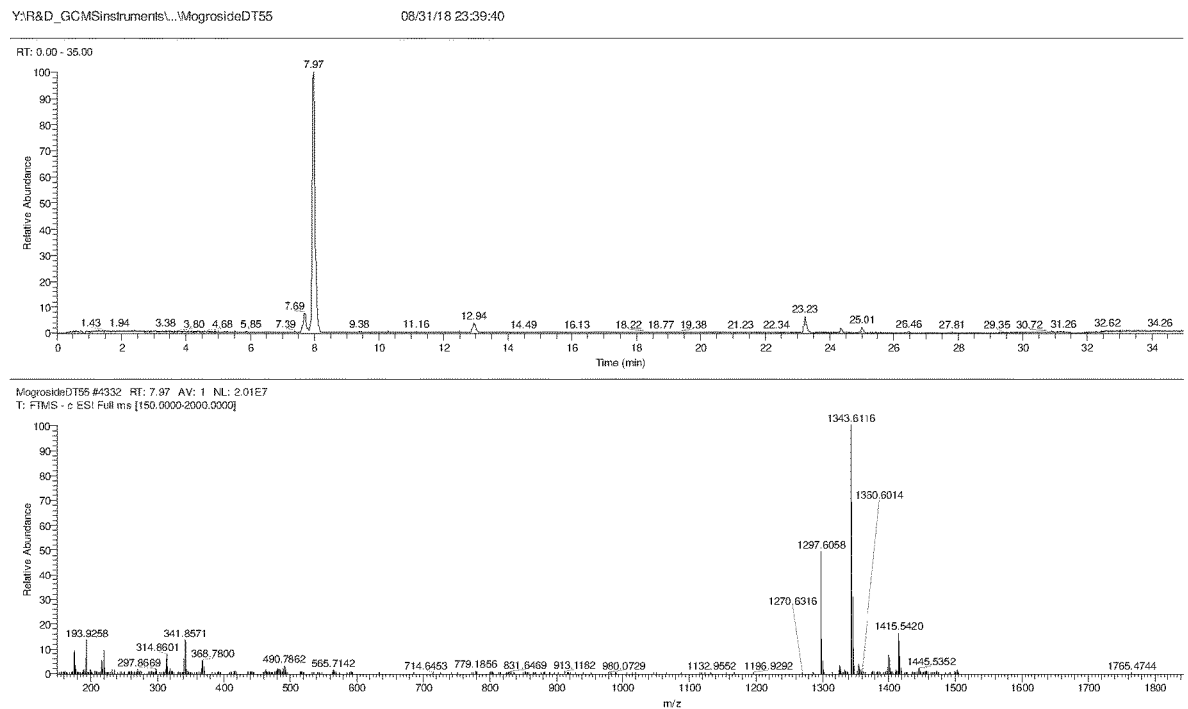
FIG. 20 shows a typical LC-HR-MS spectrograph of (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a).
Figure 21:
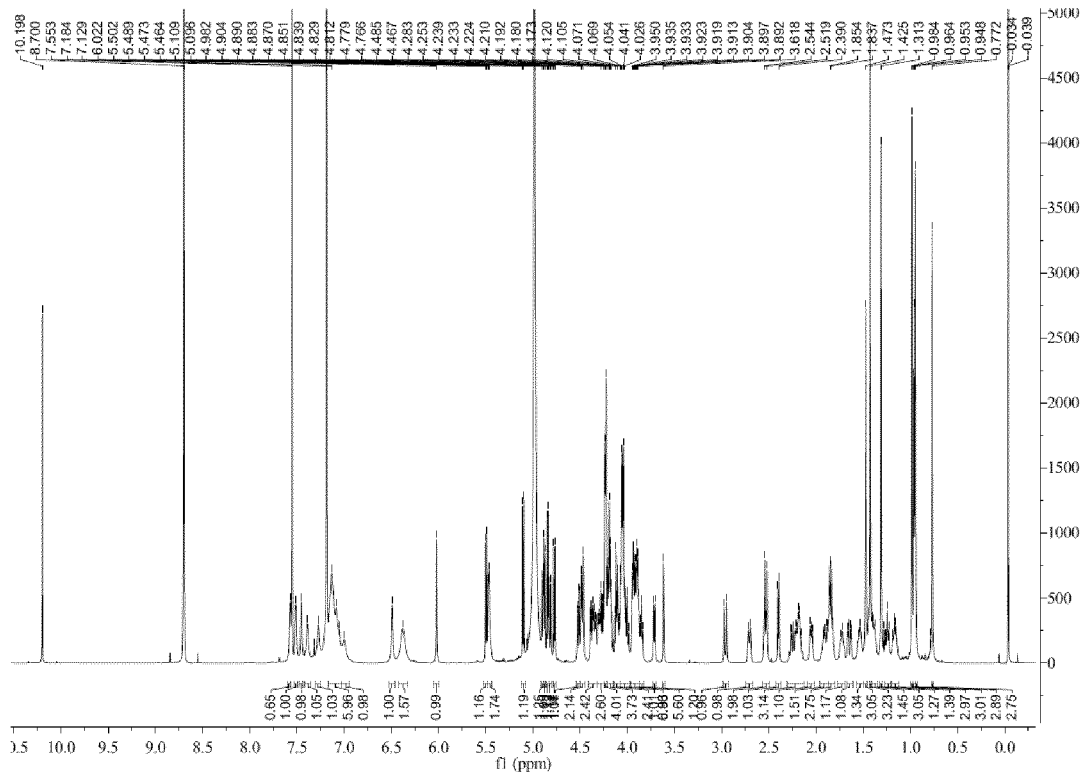
FIG. 21 shows a typical $^1$H NMR spectrograph of (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a).
Figure 22:
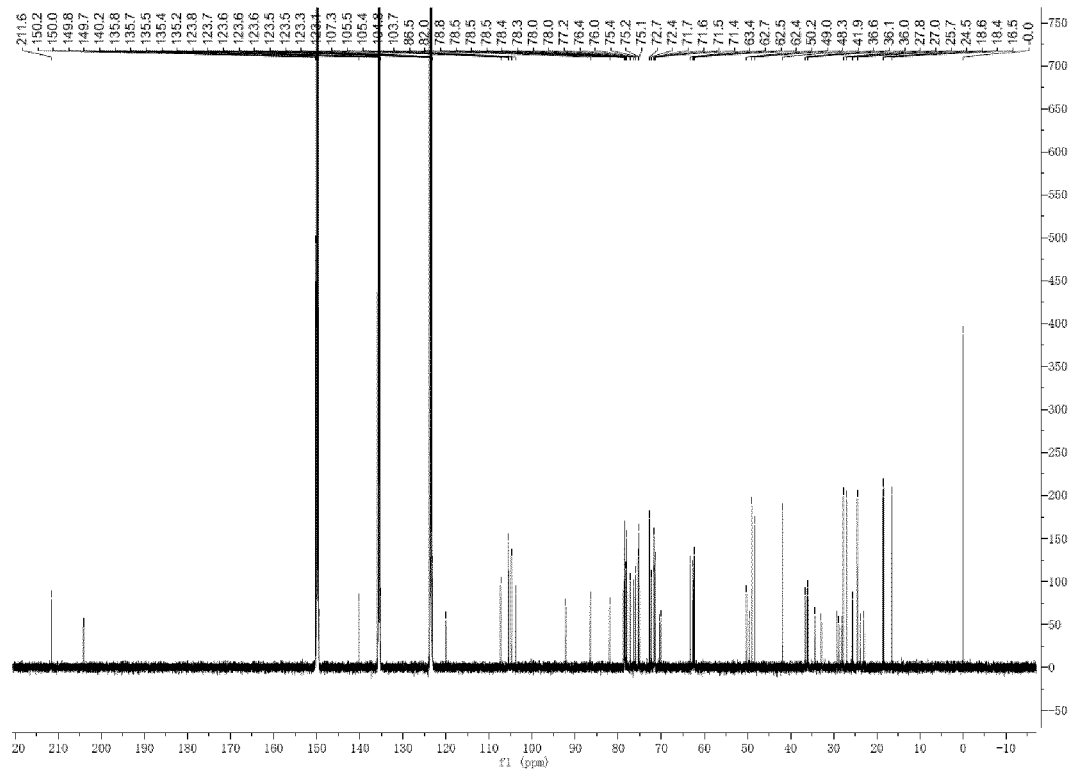
FIG. 22 shows a typical $^{13}$C NMR spectrograph of (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a).

Referring to FIGS. 20 to 22, in some embodiments, the at least one compound according to an aspect presented herein is (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a).

Figure 23:
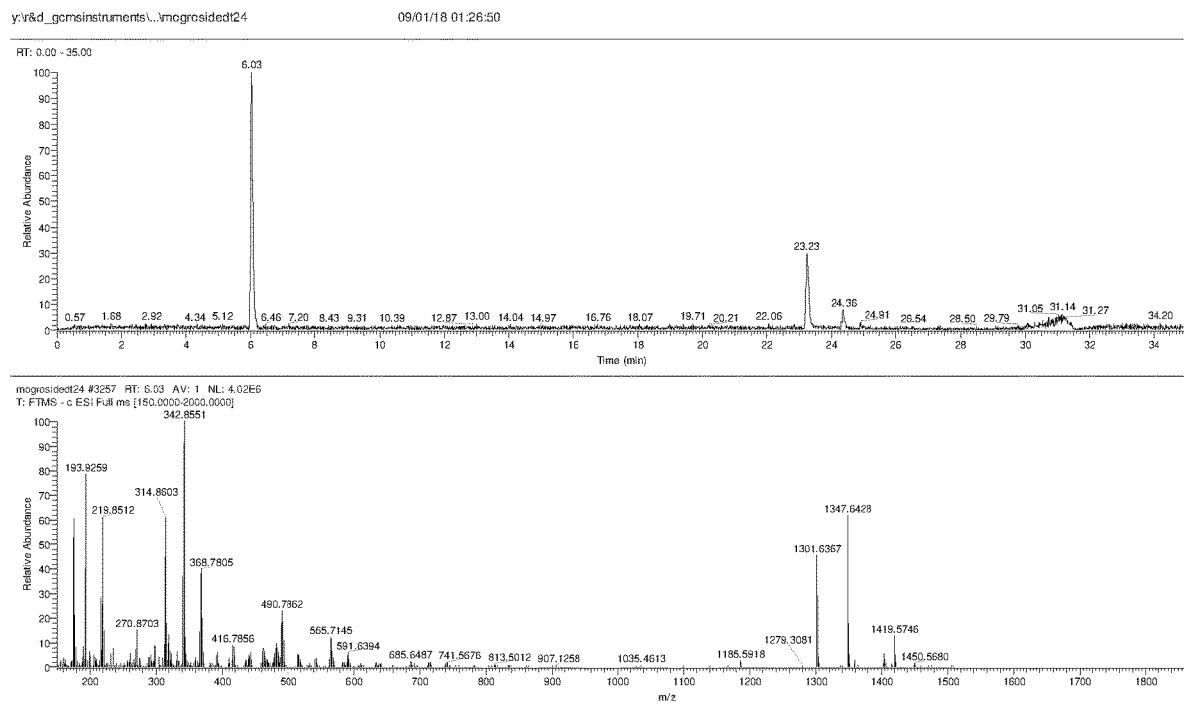
FIG. 23 shows a typical LC-HR-MS spectrograph of (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a).
Figure 24:
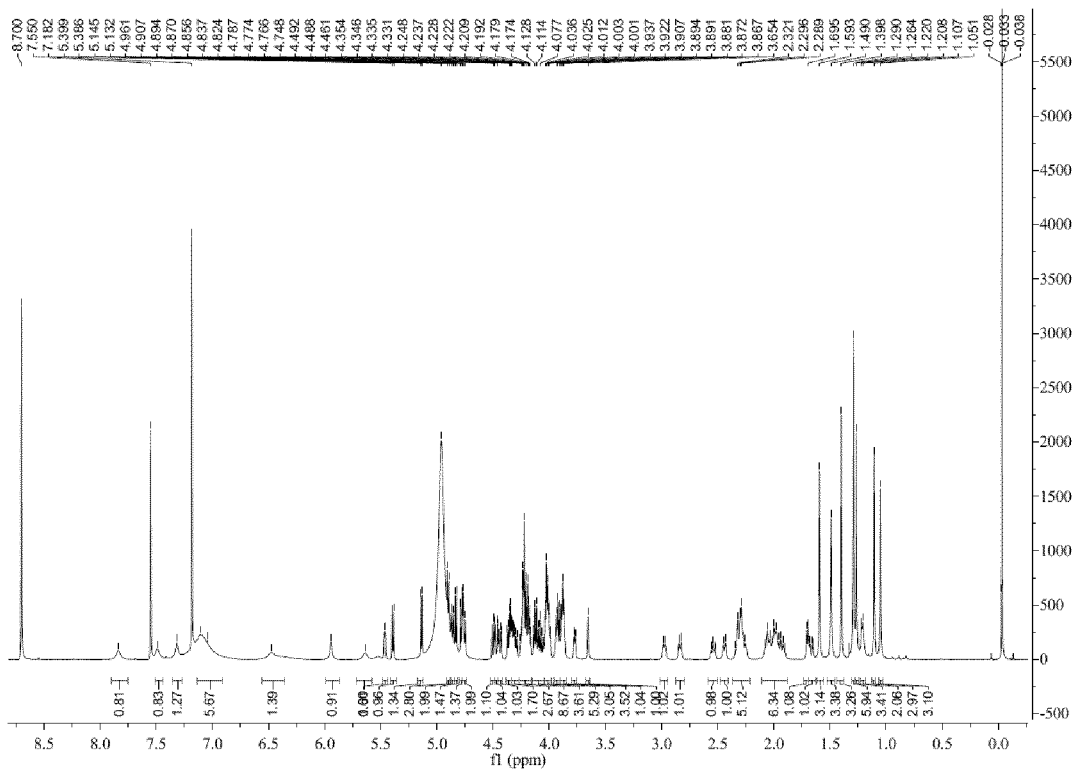
FIG. 24 shows a typical $^1$H NMR spectrograph of (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a).
Figure 25:
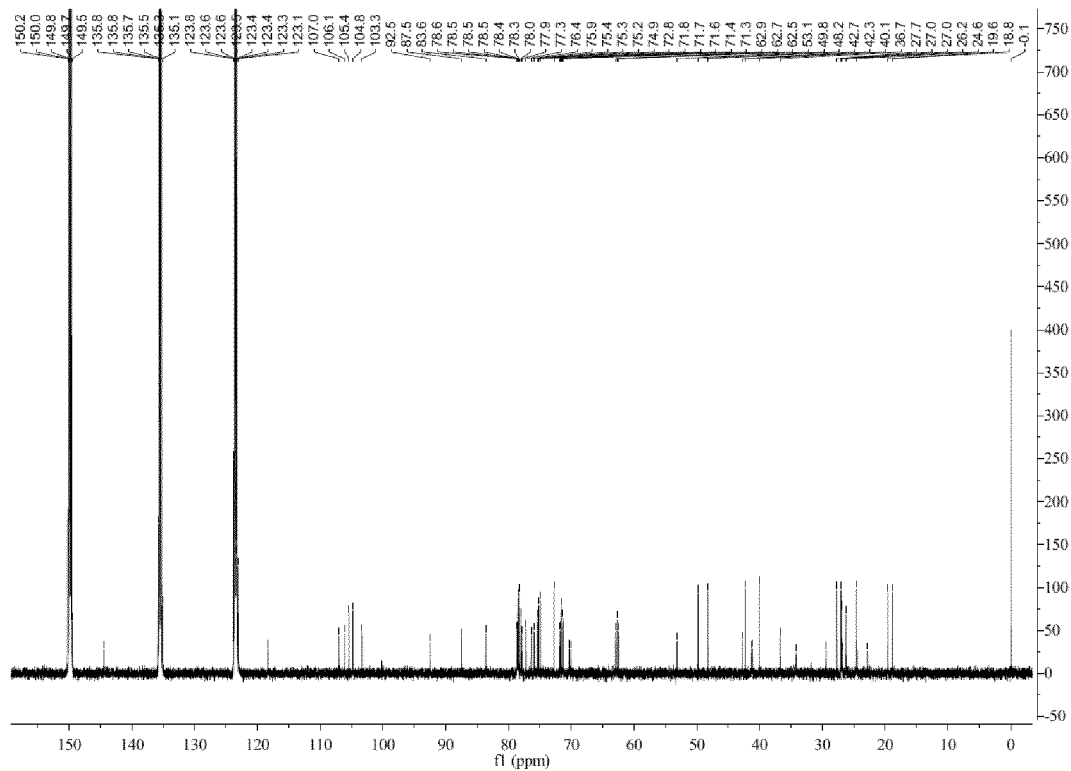
FIG. 25 shows a typical $^{13}$C NMR spectrograph of (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a).

Referring to FIGS. 23 to 25, in some embodiments, the at least one compound according to an aspect presented herein is (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a).

Figure 26:
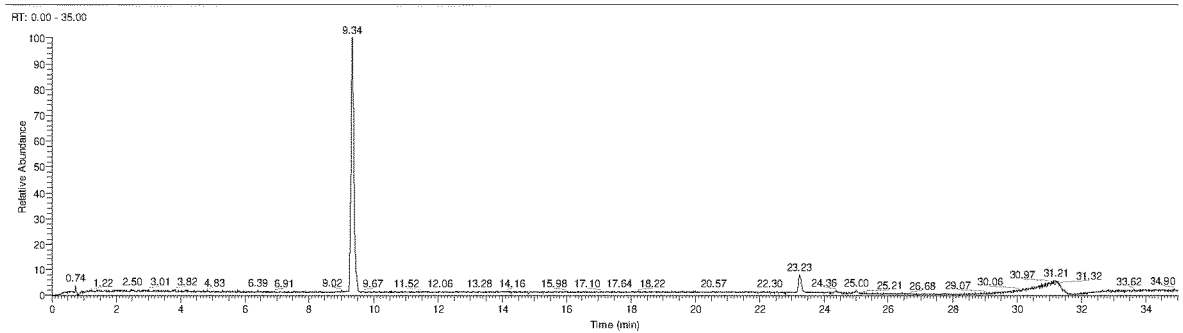
FIG. 26 shows a typical LC-HR-MS spectrograph of (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a).
Figure 26:
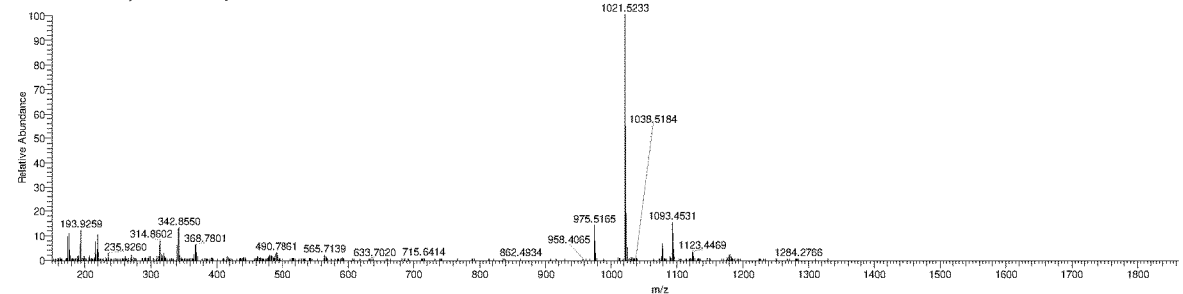
Figure 27:
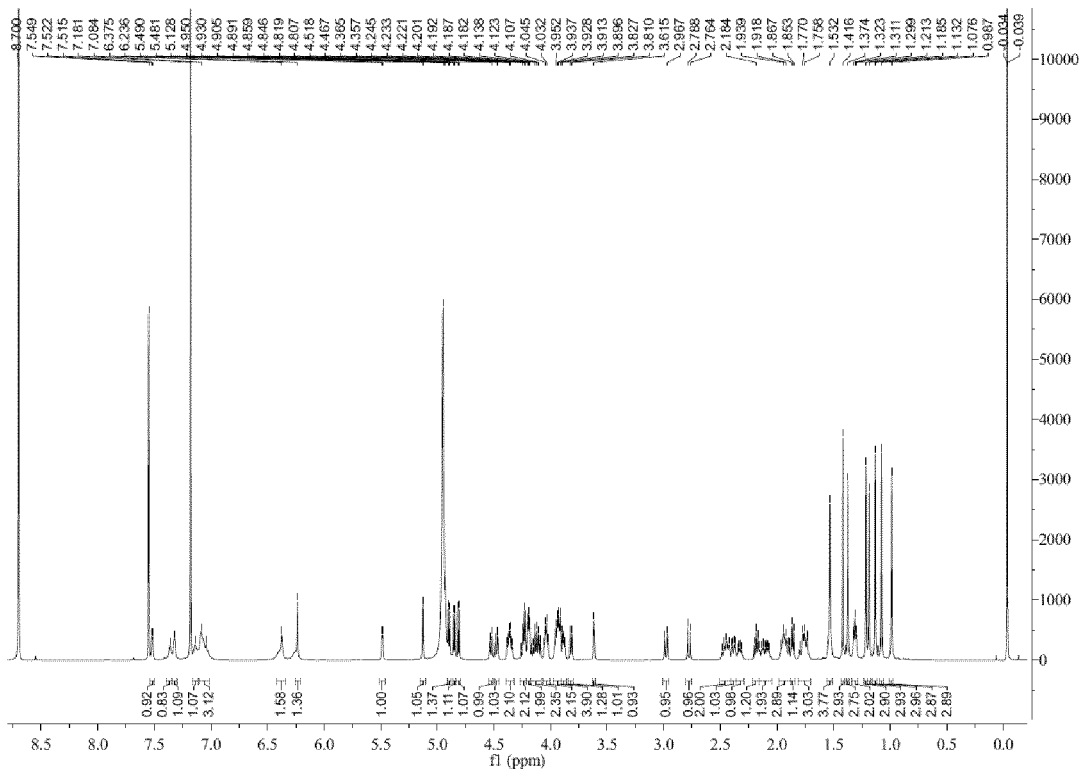
FIG. 27 shows a typical $^1$H NMR spectrograph of (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a).
Figure 28:
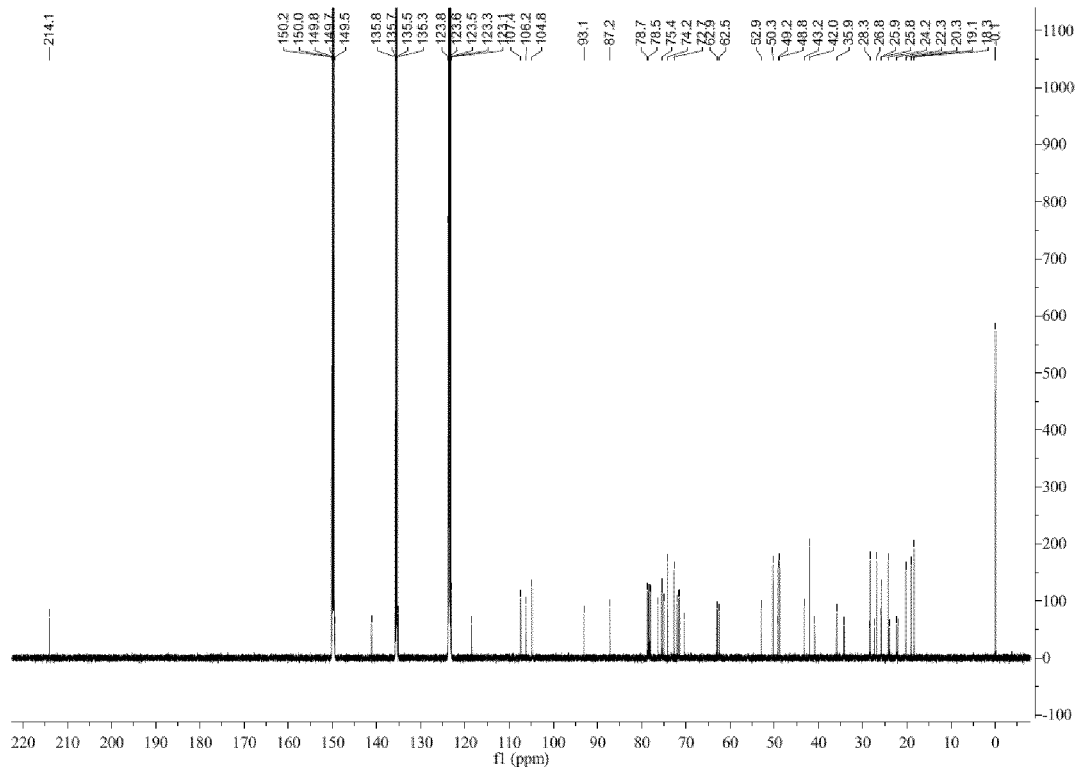
FIG. 28 shows a typical $^{13}$C NMR spectrograph of (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a).

Referring to FIGS. 26 to 28, in some embodiments, the at least one compound according to an aspect presented herein is (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a).

Figure 29:
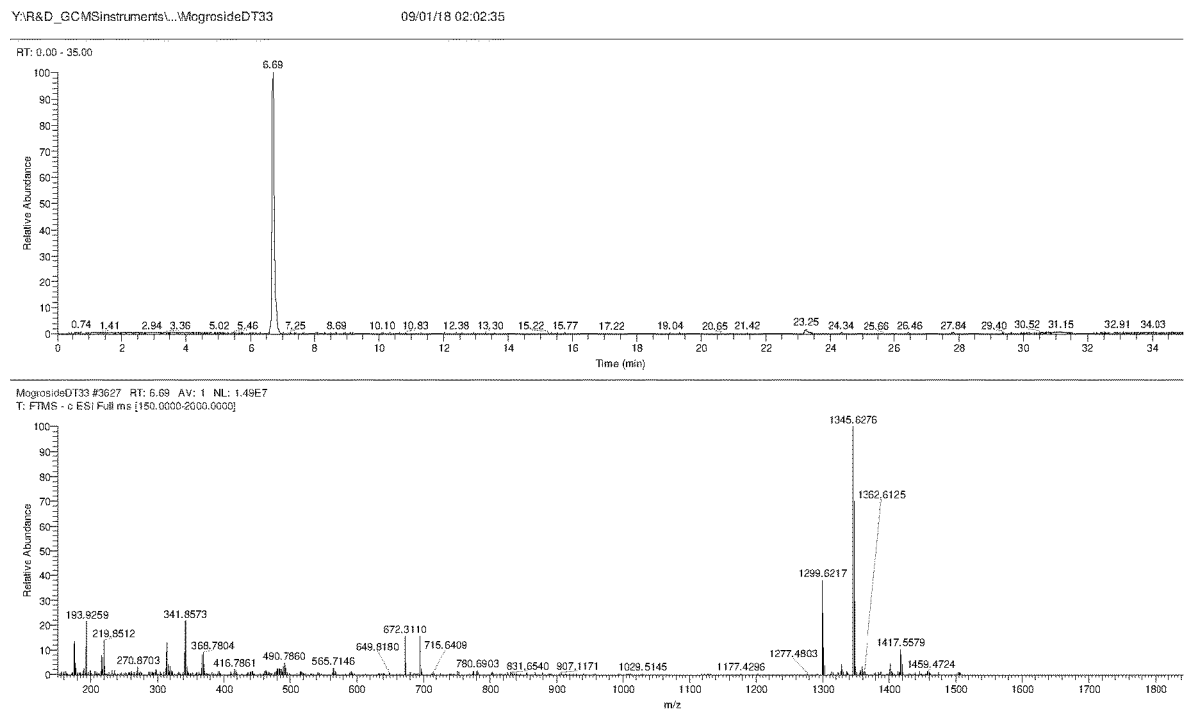
FIG. 29 shows a typical LC-HR-MS spectrograph of (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a).
Figure 30:
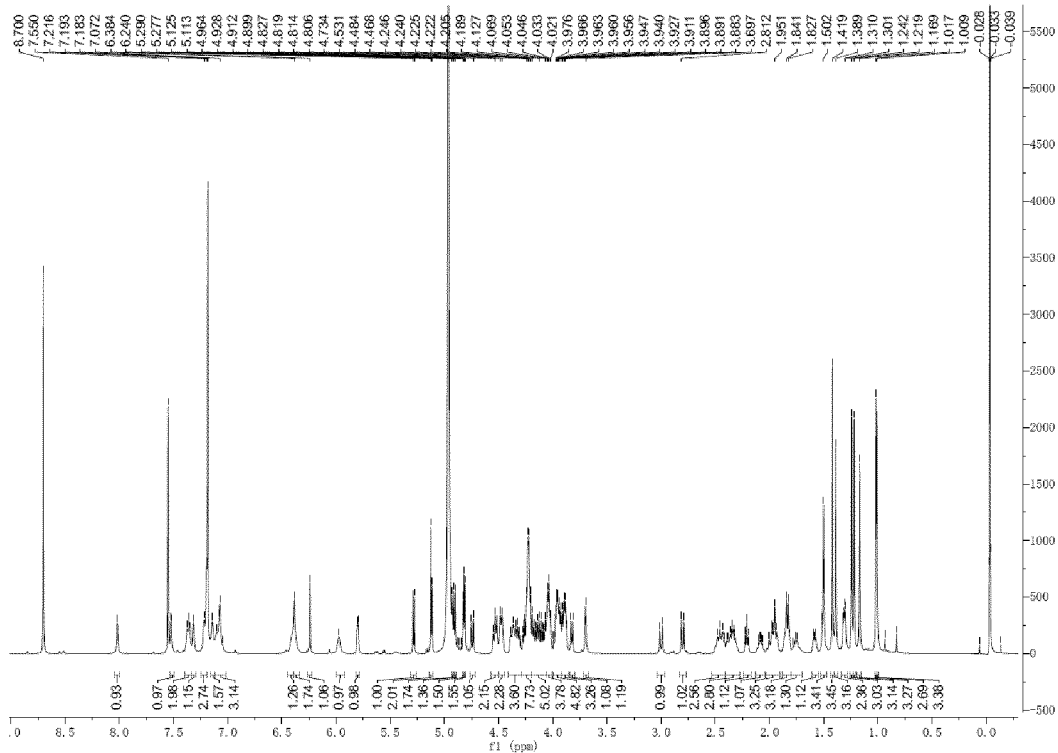
FIG. 30 shows a typical $^1$H NMR spectrograph of (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a).
Figure 31:
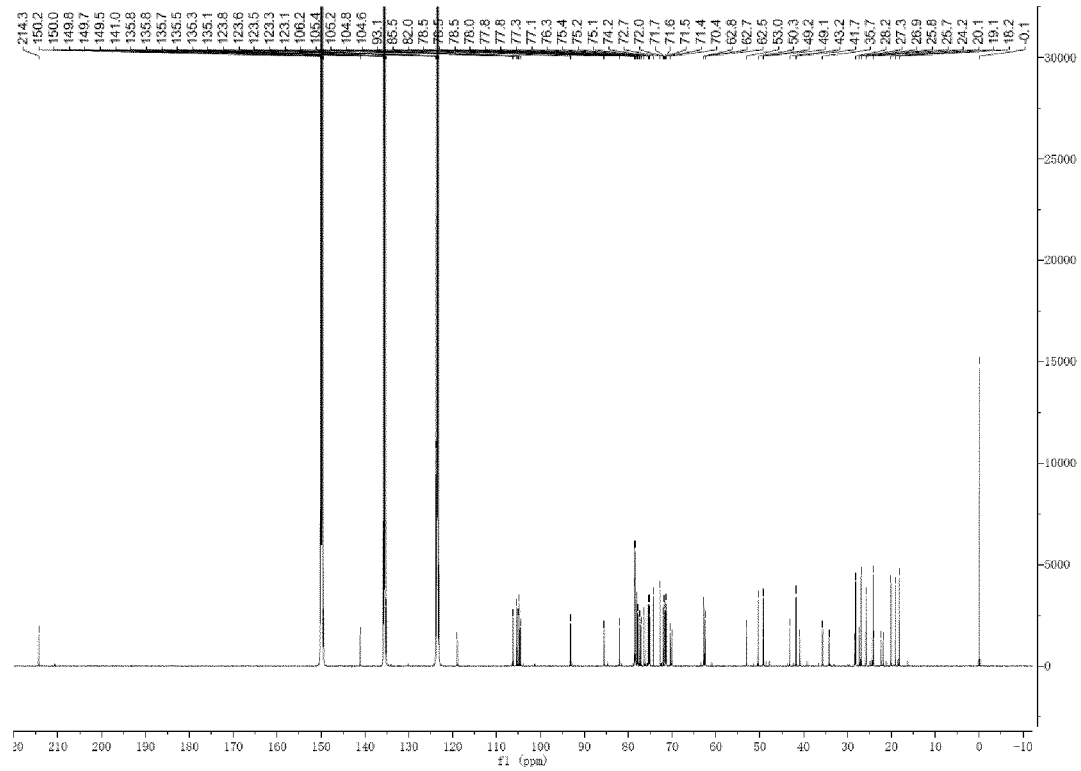
FIG. 31 shows a typical $^{13}$C NMR spectrograph of (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a).

Referring to FIGS. 29 to 31, in some embodiments, the at least one compound according to an aspect presented herein is (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a).

Figure 32:
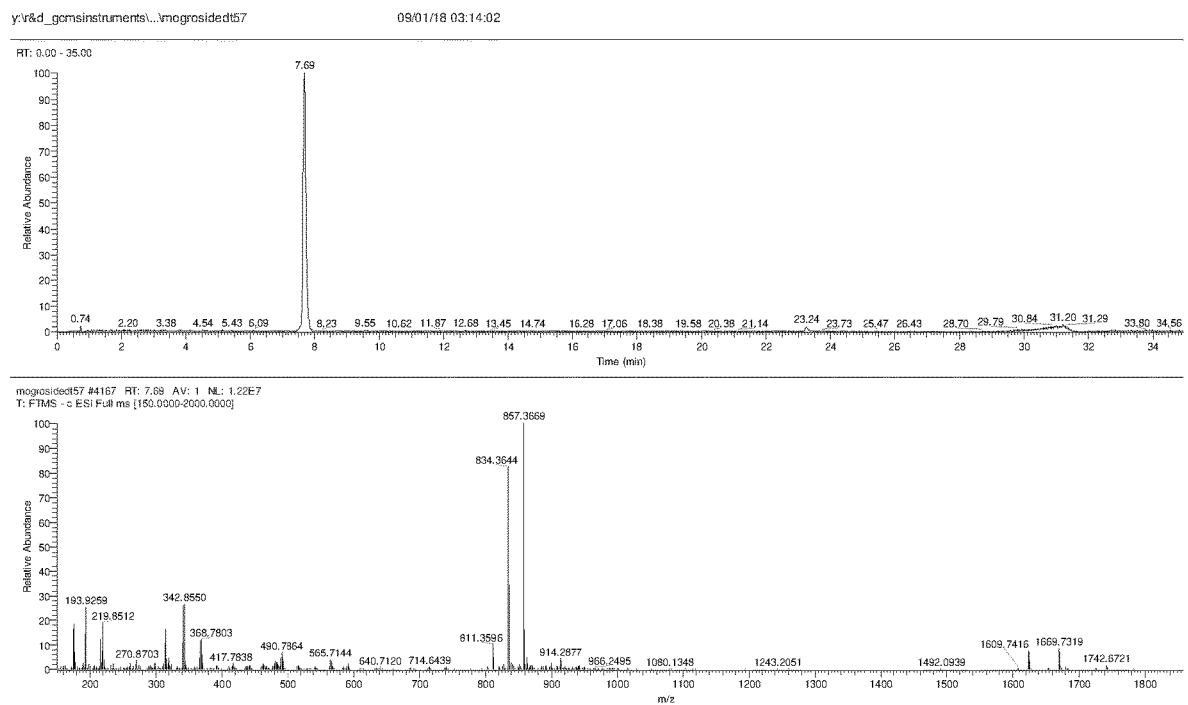
FIG. 32 shows a typical LC-HR-MS spectrograph of [(1S,4R,9beta,10R,24R)-24-{[beta-D-glucopyranosyl-(1→6)-beta-D-glucopyranosyl-(1→6)-beta-D-glucopyranosyl]-oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).
Figure 33:
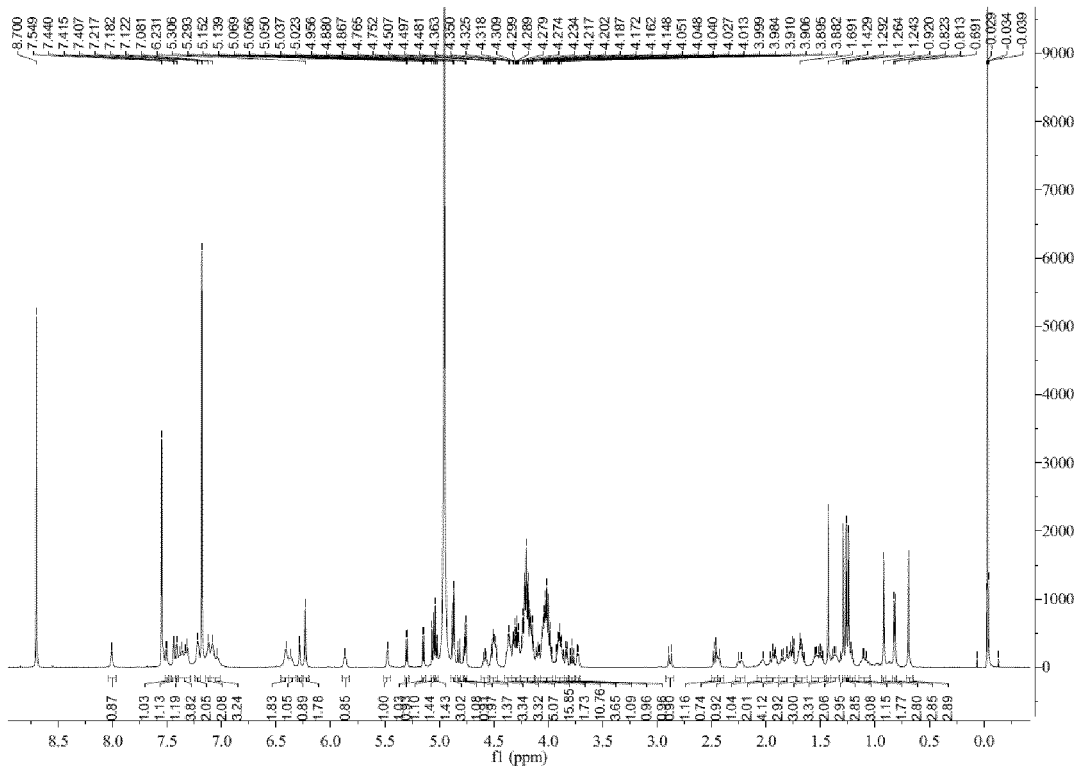
FIG. 33 shows a typical $^1$H NMR spectrograph of of [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).
Figure 34:
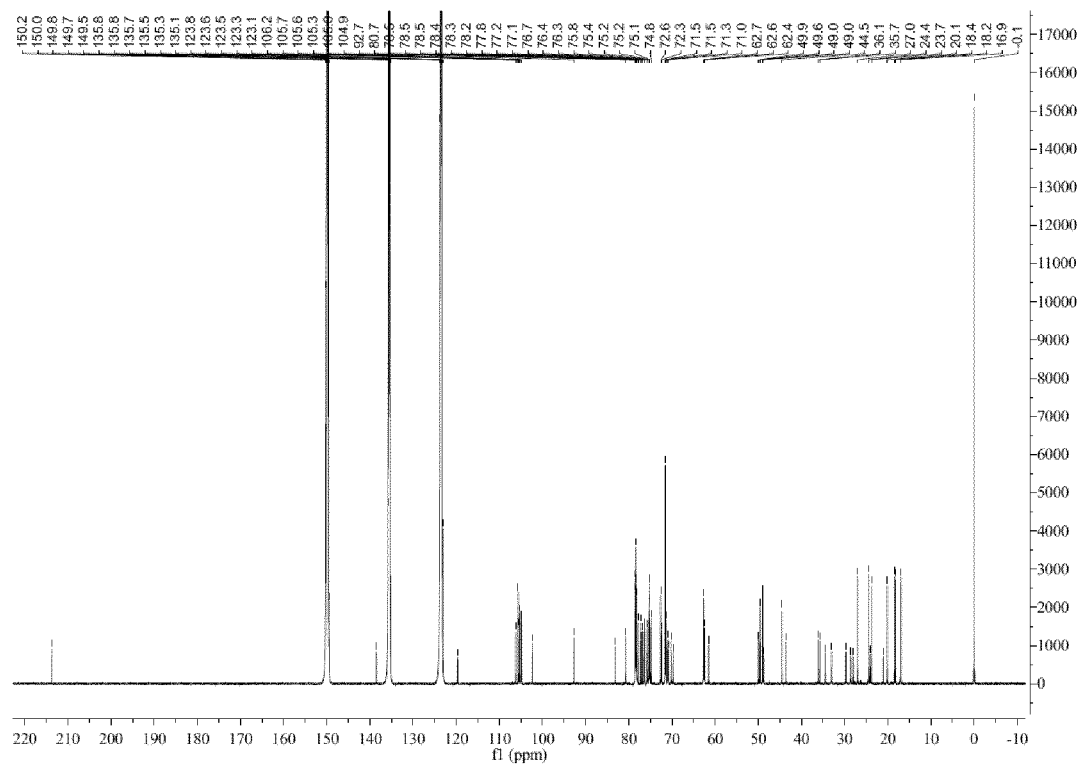
FIG. 34 shows a typical $^{13}$C NMR spectrograph of of [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).

Referring to FIGS. 32 to 34, in some embodiments, the at least one compound according to an aspect presented herein is [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a).

Figure 35:
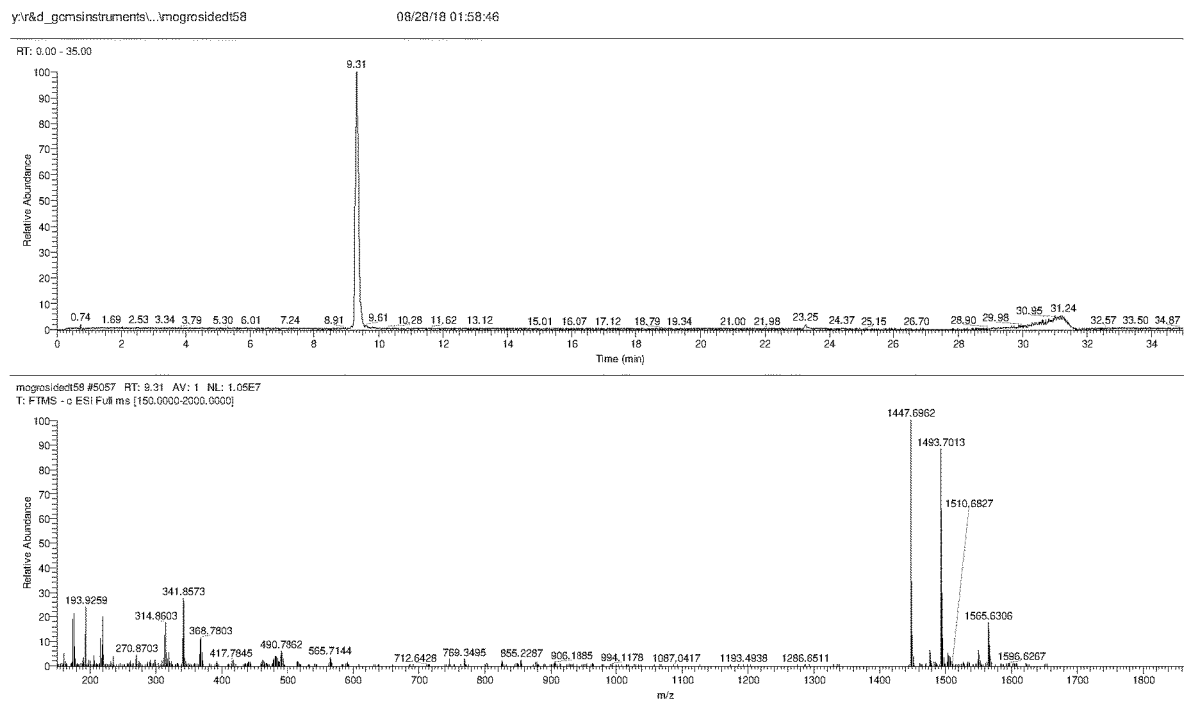
FIG. 35 shows a typical LC-HR-MS spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a).
Figure 36:
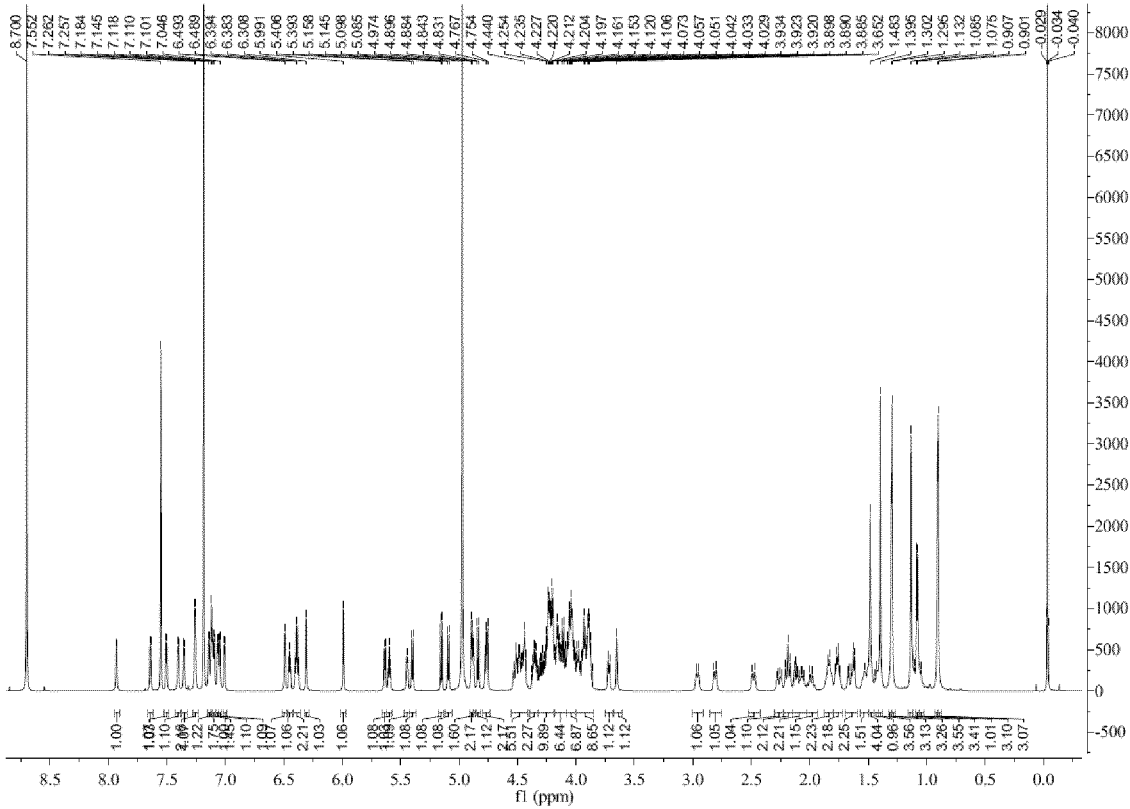
FIG. 36 shows a typical $^1$H NMR spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a).
Figure 37:
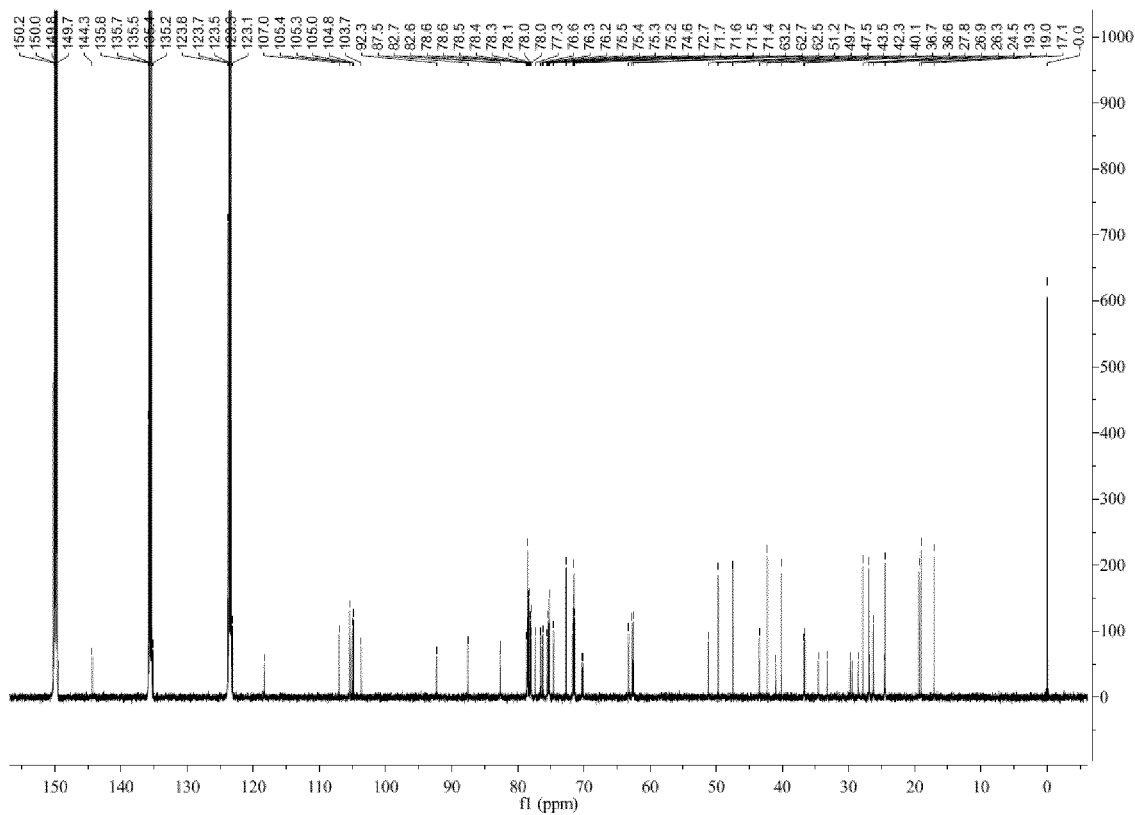
FIG. 37 shows a typical $^{13}$C NMR spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-gluco-pyranosyl-(1→4)-beta-D-glucopyranosyl-(1→2)]-beta-D-glucopyranoside (Compound 12a).

Referring to FIGS. 35 to 37, in some embodiments, the at least one compound according to an aspect presented herein is (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a).

Figure 38:
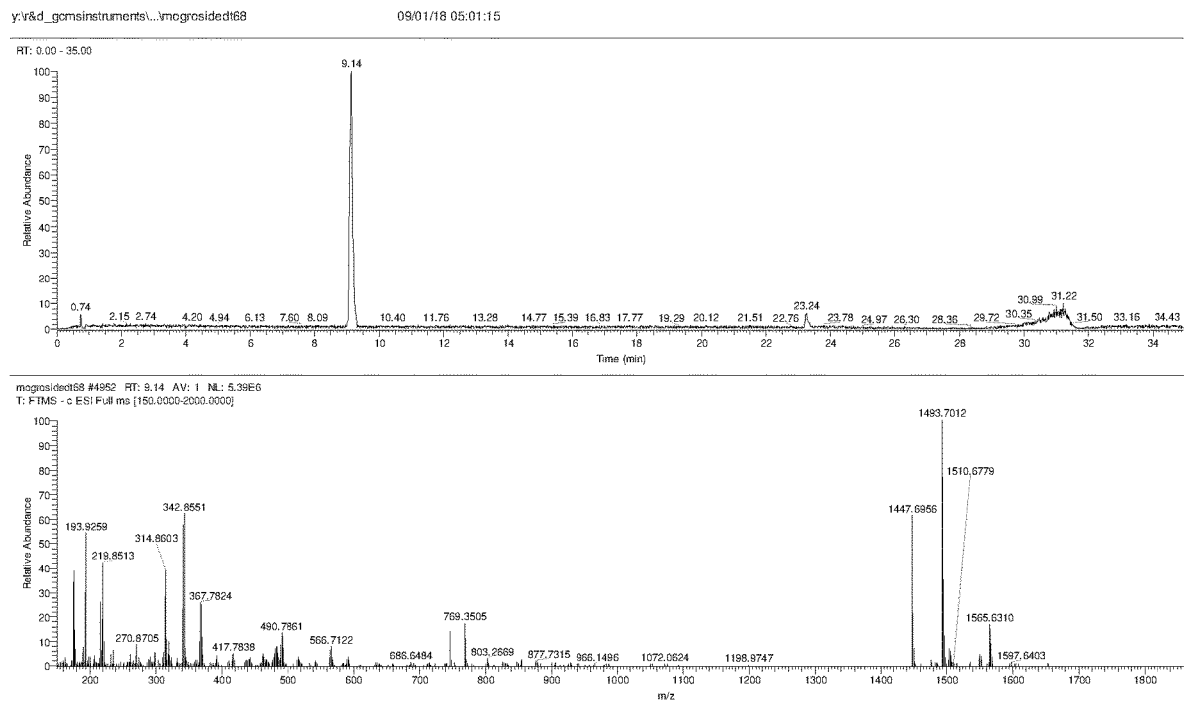
FIG. 38 shows a typical LC-HR-MS spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a).
Figure 39:
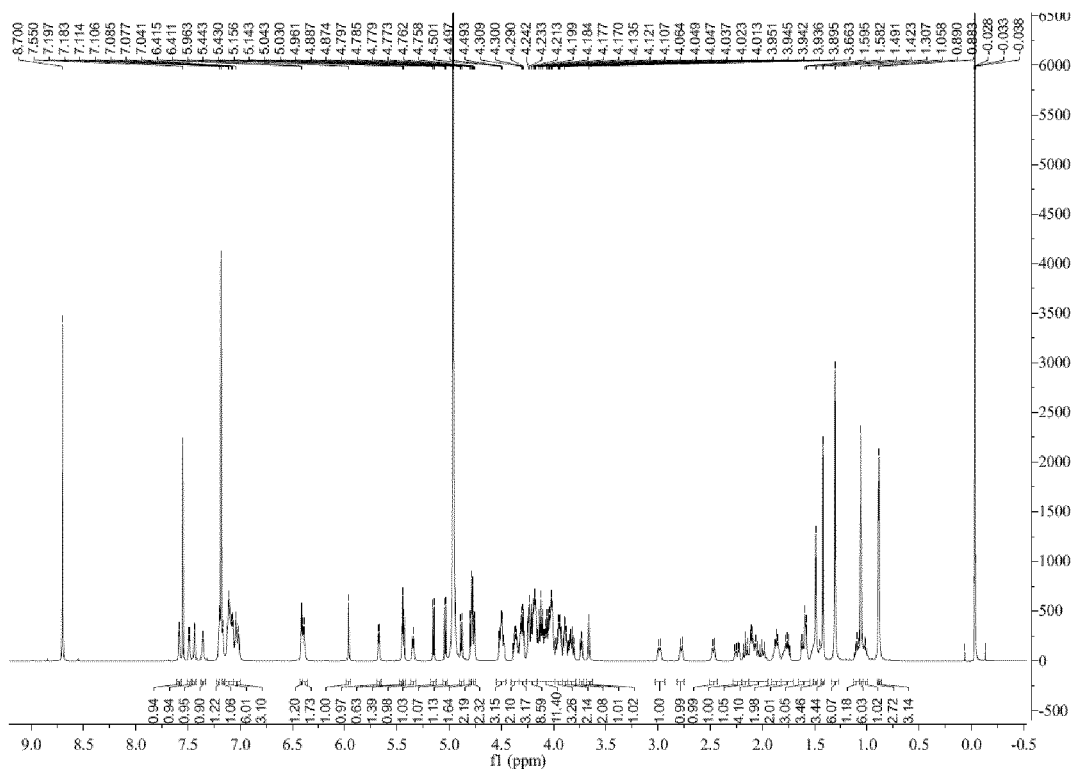
FIG. 39 shows a typical $^1$H NMR spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-gluco-pyranosyl-(1→6)-beta-D-glucopyranosyl-(1→6)]-beta-D-glucopyranoside (Compound 13a).
Figure 40:
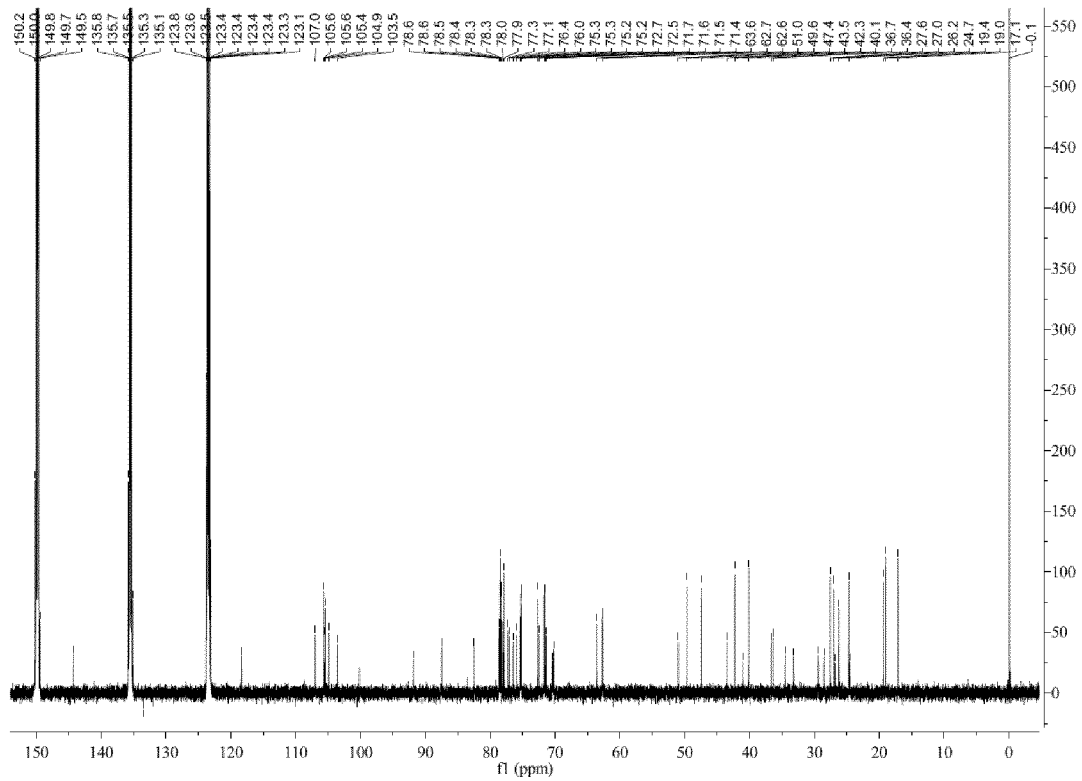
FIG. 40 shows a typical $^{13}$C NMR spectrograph of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-gluco-pyranosyl-(1→6)-beta-D-glucopyranosyl-(1→6)]-beta-D-glucopyranoside (Compound 13a).

Referring to FIGS. 38 to 40, in some embodiments, the at least one compound according to an aspect presented herein is (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a).

Figure 41:
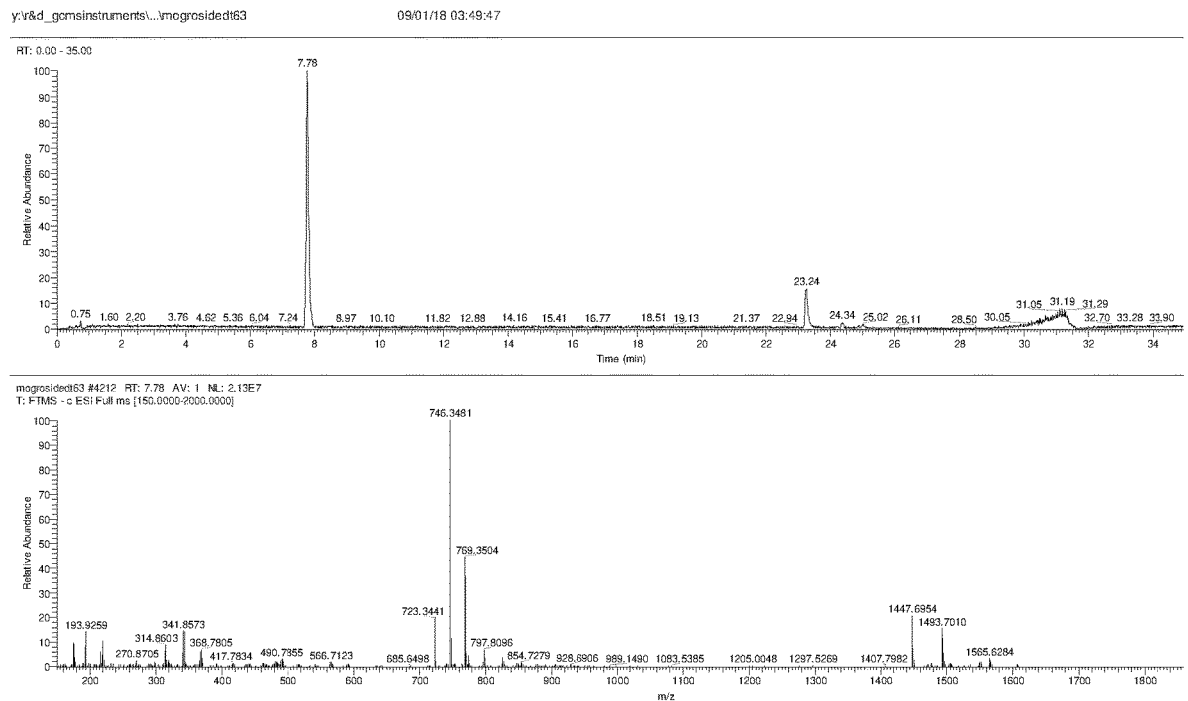
FIG. 41 shows a typical LC-HR-MS spectrograph of (1S,4R,9beta,11beta,24R)-1-{[beta-D-glucopyranosyl-(1→2)-[beta-D-glucopyranosyl-(1→6)]-beta-D-glucopyranosyl]-oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a).
Figure 42:
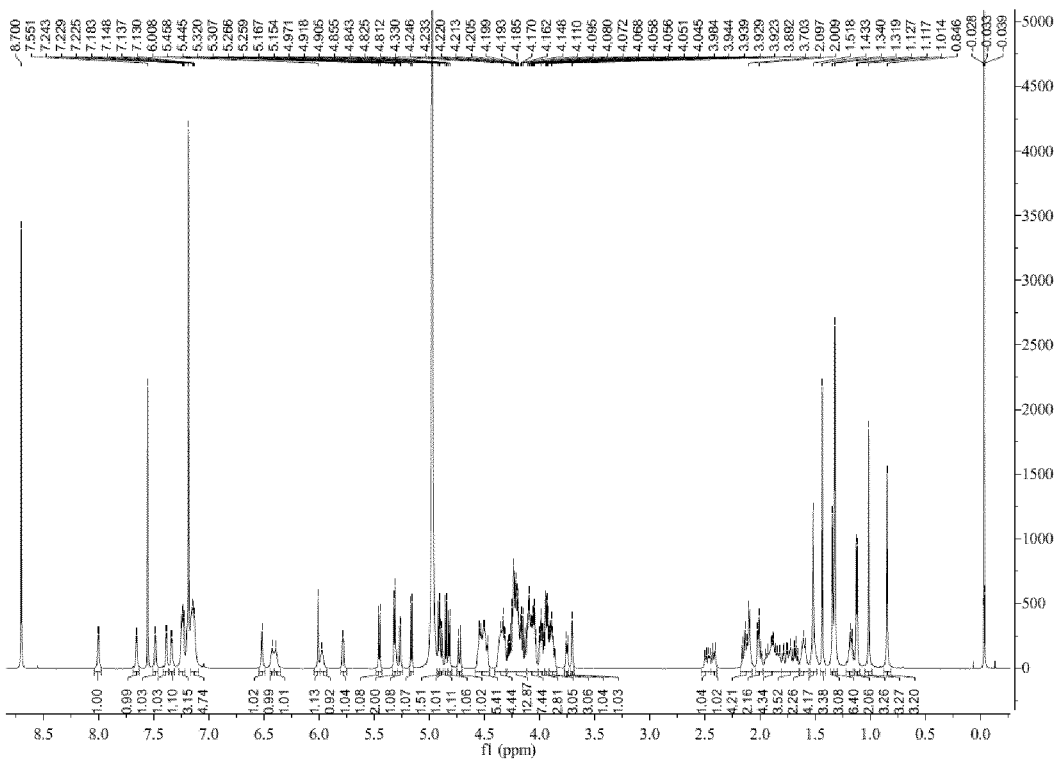
FIG. 42 shows a typical $^1$H NMR spectrograph of (1S,4R,9beta,11beta,24R)-1-{[beta-D-glucopyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-gluco-pyranosyl-(1→2)-[beta-D-glucopyranosyl-(1→6)]-beta-D-glucopyranoside (11-epi-mogroside VI, Compound 14a).
Figure 43:
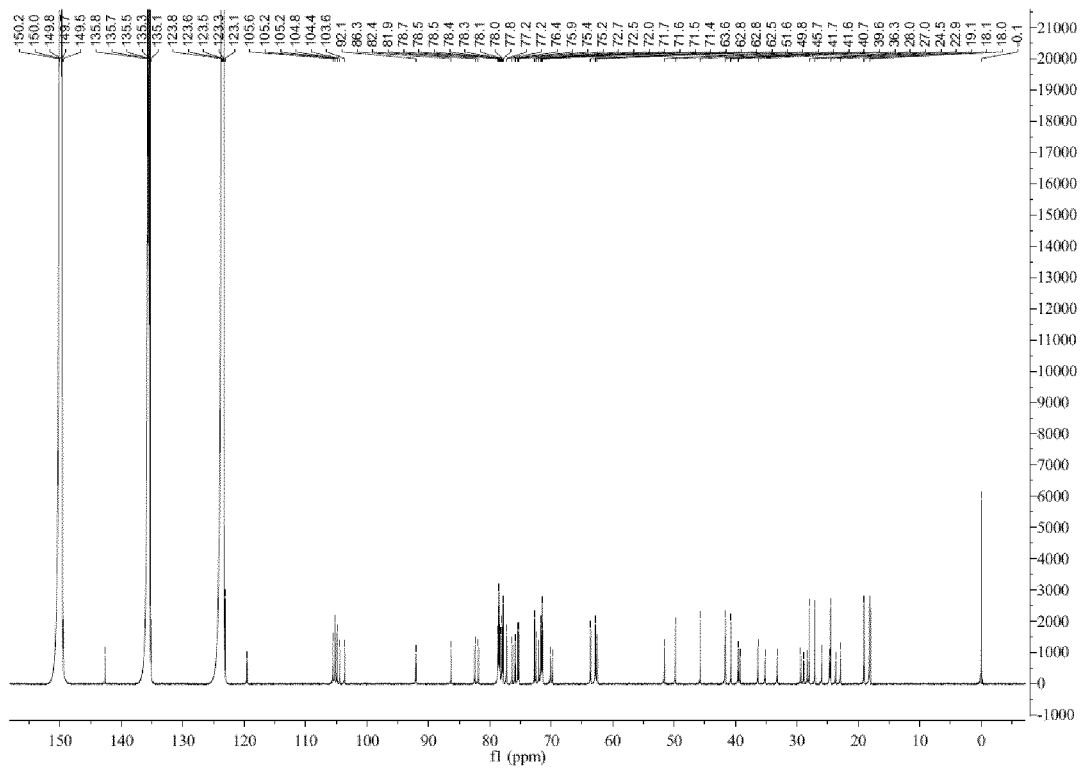
FIG. 43 shows a typical $^{13}$C NMR spectrograph of (1S,4R,9beta,11beta,24R)-1-{[beta-D-glucopyranosyl-(1→2)-[beta-D-glucopyranosyl-(1→6)]-beta-D-glucopyranosyl]-oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a).

Referring to FIGS. 41 to 43, in some embodiments, the at least one compound according to an aspect presented herein is (1S,4R,9beta,11beta,24R)-1-{[beta-D-gluco-pyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a).

Figure 44:
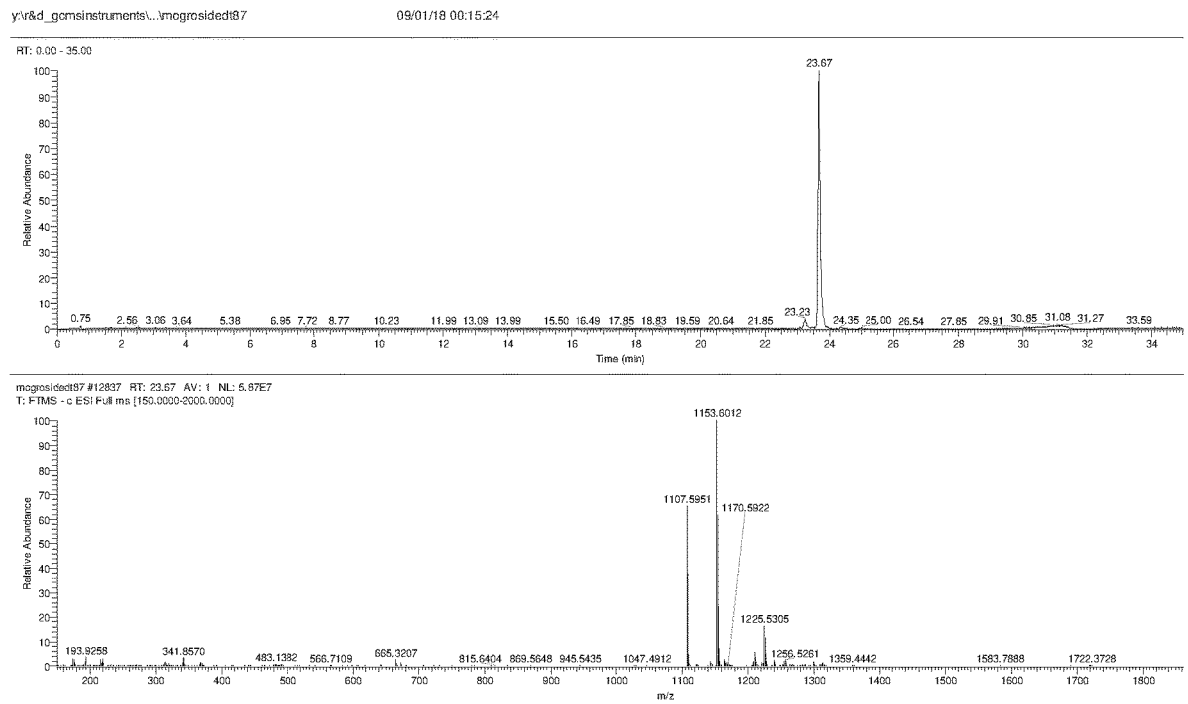
FIG. 44 shows a typical LC-HR-MS spectrograph of (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).
Figure 45:
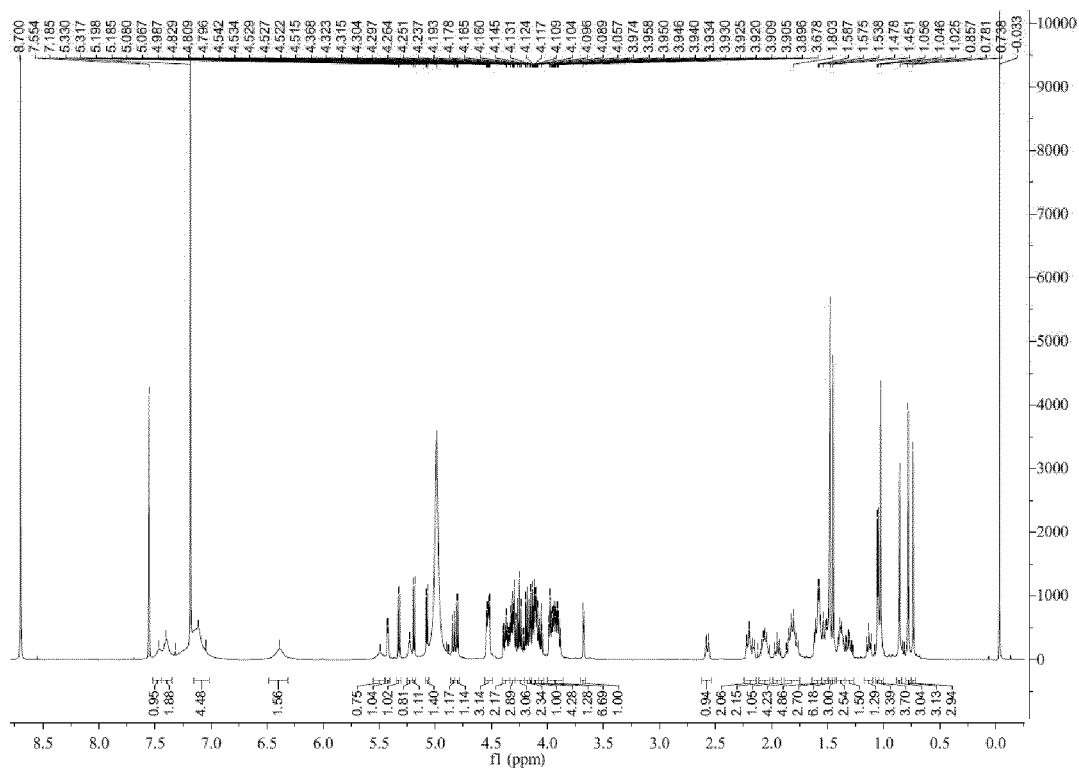
FIG. 45 shows a typical $^1$H NMR spectrograph of (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).
Figure 46:
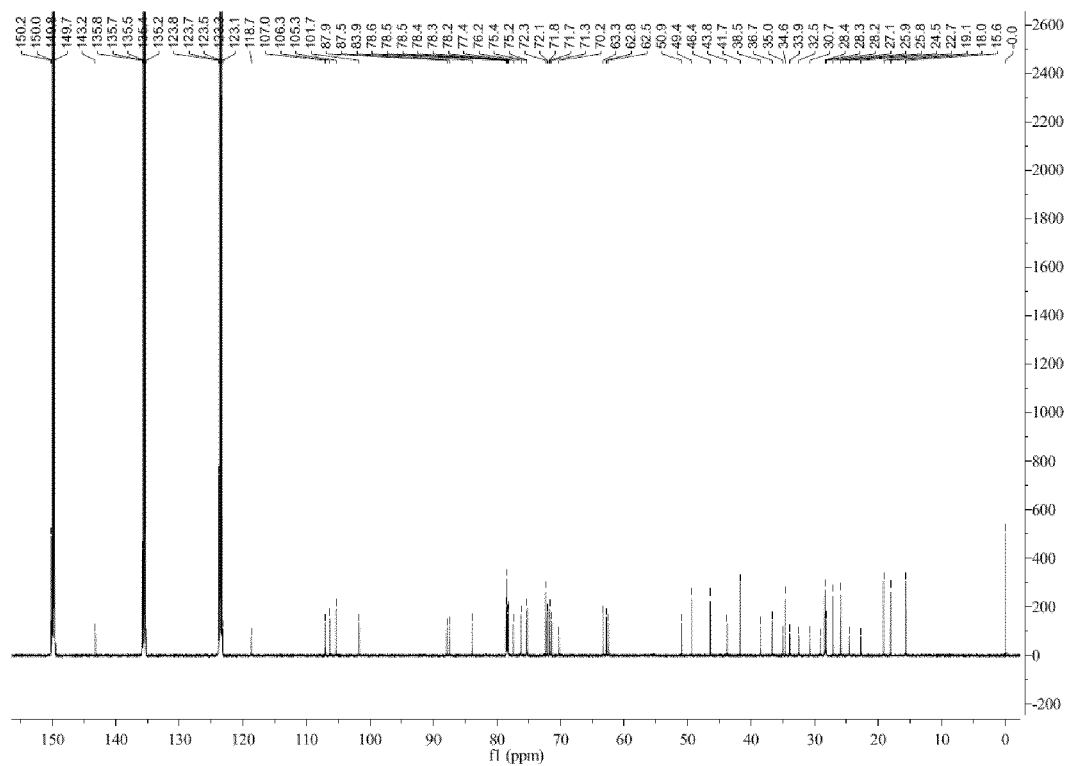
FIG. 46 shows a typical $^{13}$C NMR spectrograph of (1S,4S,9beta,24R)-1-{[6-O-(beta-D-glucopyranosyl)-beta- D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).

Referring to FIGS. 44 to 46, in some embodiments, the at least one compound according to an aspect presented herein is (1S,4S,9beta,24R)-1-{[6-O-(beta-D-gluco-pyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a).

Sweeteners and/or Sweetness Enhancers

The at least one compound according to some aspects presented herein may be used as sweetness enhancers, flavor enhancers, taste maskers and/or sweeteners in various flavored articles.

In certain aspects, the disclosure provides a method of enhancing a sweet taste of a flavored article, the method comprising: providing a flavored article, and introducing a mogroside compound of any of the preceding aspects, or embodiments thereof, to the flavored article, such as a flavored food or beverage product. In some such embodiments, the compound is introduced in an amount effective to enhance the sweet taste of the flavored article.

In certain related aspects, the disclosure provides the use of a mogroside compound of any of the preceding aspects, or embodiments thereof, to enhance a sweet taste of a flavored article, such as a flavored food or beverage product.

In some embodiments of the preceding methods and uses, the mogroside compound can be used at any suitable concentration. In some embodiments, the concentration of the mogroside compound in the flavored article ranges from 1 ppm to 1000 ppm, or from 5 ppm to 1000 ppm, or from 10 ppm to 1000 ppm, or from 10 ppm to 750 ppm, or from 10 ppm to 500 ppm, or from 10 ppm to 400 ppm, or from 10 ppm to 300 ppm. In some other embodiments, the concentration of the mogroside compound in the flavored article ranges from 1 ppm to 50 ppm, or from 1 ppm to 40 ppm, or from 1 ppm to 30 ppm, or from 5 ppm to 50 ppm, or from 5 ppm to 40 ppm, or from 5 ppm to 30 ppm. In some further embodiments, the concentration of the mogroside compound in the flavored article is 1 ppm, 5 ppm, 10 ppm, 20 ppm, 30 ppm, 40 ppm, 50 ppm, 60 ppm, 70 ppm, 80 ppm, 90 ppm, 100 ppm, 150 ppm, 200 ppm, 250 ppm, 300 ppm, 350 ppm, 400 ppm, 450 ppm, 500 ppm, 600 ppm, 700 ppm, 800 ppm, 900 ppm, 1000 ppm.

In certain aspects, the disclosure provides compositions, such as comestible compositions, comprising a mogroside compound of any of the preceding aspects, or embodiments thereof. In some embodiments thereof, the comestible composition comprises a carrier, such as a bulking agent (such as erythritol, allulose, a cellulosic material, or any combination thereof) or water. In some related aspects, the comestible compositions are incorporated into, or are, a flavored article, such as a flavored food or beverage product.

In some embodiments of the preceding composition aspects, the mogroside compound can be used at any suitable concentration in the composition. In some embodiments, the concentration of the mogroside compound in the comestible composition ranges from 1 ppm to 1000 ppm, or from 5 ppm to 1000 ppm, or from 10 ppm to 1000 ppm, or from 10 ppm to 750 ppm, or from 10 ppm to 500 ppm, or from 10 ppm to 400 ppm, or from 10 ppm to 300 ppm. In some other embodiments, the concentration of the mogroside compound in the comestible composition ranges from 1 ppm to 50 ppm, or from 1 ppm to 40 ppm, or from 1 ppm to 30 ppm, or from 5 ppm to 50 ppm, or from 5 ppm to 40 ppm, or from 5 ppm to 30 ppm. In some further embodiments, the concentration of the mogroside compound in the comestible composition is 1 ppm, 5 ppm, 10 ppm, 20 ppm, 30 ppm, 40 ppm, 50 ppm, 60 ppm, 70 ppm, 80 ppm, 90 ppm, 100 ppm, 150 ppm, 200 ppm, 250 ppm, 300 ppm, 350 ppm, 400 ppm, 450 ppm, 500 ppm, 600 ppm, 700 ppm, 800 ppm, 900 ppm, 1000 ppm.

In certain particular embodiments, the ingestible composition comprises sucrose and the mogroside compound or any of its comestibly acceptable salts. In some such embodiments, the introduction of the mogroside compound (or salt) permits one to use less sucrose (such as more than 10% less, more than 20% less, more than 30% less, more than 40% less, more than 50% less, more than 60% less, or more than 70% less) and still achieve a level of sweetness characteristic of a comparable product that employs more sucrose. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. The sucrose can be introduced in any suitable form, such as natural syrups (cane syrup) and the like.

In certain particular embodiments, the ingestible composition comprises fructose and the mogroside compound or any of its comestibly acceptable salts. In some such embodiments, the introduction of the mogroside compound (or salt) permits one to use less fructose (such as more than 10% less, more than 20% less, more than 30% less, more than 40% less, more than 50% less, more than 60% less, or more than 70% less) and still achieve a level of sweetness characteristic of a comparable product that employs more fructose. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some embodiments, the ingestible composition is a food product, such as any of those specifically listed below. In other embodiments, the ingestible composition is a beverage product, such as a soda, and the like. The fructose can be supplied in any suitable form, such as natural syrups, high-fructose corn syrup, and the like.

In certain particular embodiments, the ingestible composition comprises high-fructose corn syrup and the mogroside compound or any of its comestibly acceptable salts. In some such embodiments, the introduction of the mogroside compound (or salt) permits one to use less high-fructose corn syrup (such as more than 10% less, more than 20% less, more than 30% less, more than 40% less, more than 50% less, more than 60% less, or more than 70% less) and still achieve a level of sweetness characteristic of a comparable product that employs more high-fructose corn syrup. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some embodiments, the ingestible composition is a food product, such as any of those specifically listed below. In other embodiments, the ingestible composition is a beverage product, such as a soda, and the like.

In certain particular embodiments, the ingestible composition comprises glucose (for example, D-glucose, in either its alpha or beta forms, or a combination thereof) and the mogroside compound or any of its comestibly acceptable salts. In some such embodiments, the introduction of the mogroside compound (or salt) permits one to use less glucose (such as more than 10% less, more than 20% less, more than 30% less, more than 40% less, more than 50% less, more than 60% less, or more than 70% less) and still achieve a level of sweetness characteristic of a comparable product that employs more glucose. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. The glucose can be introduced in any suitable form, such as natural syrups and the like.

In certain particular embodiments, the ingestible composition comprises sucralose and the mogroside compound or any of its comestibly acceptable salts. In some such embodiments, the introduction of the mogroside compound (or salt) permits one to use less sucralose (such as more than 10% less, more than 20% less, more than 30% less, more than 40% less, more than 50% less, more than 60% less, or more than 70% less) and still achieve a level of sweetness characteristic of a comparable product that employs more sucralose. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises rebaudiosides (such as rebaudioside A, rebaudioside D, rebaudioside E, rebaudioside M, or any combination thereof) and the mogroside compound or any of its comestibly acceptable salts. In some such embodiments, the introduction of the mogroside compound (or salt) permits one to use less rebaudioside (such as more than 10% less, more than 20% less, more than 30% less, more than 40% less, more than 50% less, more than 60% less, or more than 70% less) and still achieve a level of sweetness characteristic of a comparable product that employs more rebaudioside. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises acesulfame K and the mogroside compound or any of its comestibly acceptable salts. In some such embodiments, the introduction of the mogroside compound (or salt) permits one to use less acesulfame K (such as more than 10% less, more than 20% less, more than 30% less, more than 40% less, more than 50% less, more than 60% less, or more than 70% less) and still achieve a level of sweetness characteristic of a comparable product that employs more acesulfame K. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises allulose and the mogroside compound or any of its comestibly acceptable salts. In some such embodiments, the introduction of the mogroside compound (or salt) permits one to use less allulose (such as more than 10% less, more than 20% less, more than 30% less, more than 40% less, more than 50% less, more than 60% less, or more than 70% less) and still achieve a level of sweetness characteristic of a comparable product that employs more allulose. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises erythritol and the mogroside compound or any of its comestibly acceptable salts. In some such embodiments, the introduction of the mogroside compound (or salt) permits one to use less erythritol (such as more than 10% less, more than 20% less, more than 30% less, more than 40% less, more than 50% less, more than 60% less, or more than 70% less) and still achieve a level of sweetness characteristic of a comparable product that employs more erythritol. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises aspartame and the mogroside compound or any of its comestibly acceptable salts. In some such embodiments, the introduction of the mogroside compound (or salt) permits one to use less aspartame (such as more than 10% less, more than 20% less, more than 30% less, more than 40% less, more than 50% less, more than 60% less, or more than 70% less) and still achieve a level of sweetness characteristic of a comparable product that employs more aspartame. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises cyclamate and the mogroside compound or any of its comestibly acceptable salts. In some such embodiments, the introduction of the mogroside compound (or salt) permits one to use less cyclamate (such as more than 10% less, more than 20% less, more than 30% less, more than 40% less, more than 50% less, more than 60% less, or more than 70% less) and still achieve a level of sweetness characteristic of a comparable product that employs more cyclamate. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises a mogroside (such as mogroside III, mogroside IV, mogroside V, siamenoside I, isomogroside V, mogroside $IV_E$, mogroside $III_E$, 11-oxomogroside V, the α-1,6-isomer of siamenoside I, and any combinations thereof) and the mogroside compound or any of its comestibly acceptable salts. In some such embodiments, the introduction of the mogroside compound (or salt) permits one to use less a mogroside (such as more than 10% less, more than 20% less, more than 30% less, more than 40% less, more than 50% less, more than 60% less, or more than 70% less) and still achieve a level of sweetness characteristic of a comparable product that employs more mogroside. In some embodiments, the concentration of the mogroside compound, or its comestibly acceptable salts, is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. Additional mogroside compounds that may be suitably used are described in U.S. Patent Application Publication No. 2017/0119032.

The ingestible compositions set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness or licorice taste, compounds that enhance saltiness, compounds that enhance a cooling effect, or any combinations of the foregoing.

Thus, in some embodiments, ingestible compositions disclosed herein comprise the mogroside compound, or any comestibly acceptable salts thereof, according to any of the embodiments or combination of embodiments set forth above, are combined with one or more other sweetness enhancing compounds. Such sweetness enhancing compounds include, but are not limited to, naturally derived compounds, such as hesperitin, naringenin, glucosylated steviol glycosides, or synthetic compounds, such as any compounds set forth in U.S. Pat. Nos. 8,541,421; 8,815,956; 9,834,544; 8,592,592; 8,877,922; 9,000,054; and 9,000,051, as well as U.S. Patent Application Publication No. 2017/0119032. The mogroside compound (or comestibly acceptable salts thereof) may be used in combination with such other sweetness enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In some embodiments of any of the preceding embodiments, the mogroside compound (or any comestibly acceptable salts thereof) is combined with glucosylated steviol glycosides in any of the above ratios. As used herein, the term "glucosylated steviol glycoside" refers to the product of enzymatically glucosylating natural steviol glycoside compounds. The glucosylation generally occurs through a glycosidic bond, such as an α-1,2 bond, an α-1,4 bond, an α-1.6 bond, a β-1,2 bond, a β-1,4 bond, a β-1,6 bond, and so forth.

In some further embodiments, ingestible compositions disclosed herein comprise the mogroside compound, or any comestibly acceptable salts thereof, according to any of the embodiments or combination of embodiments set forth above, are combined with one or more umami enhancing compounds. Such umami enhancing compounds include, but are not limited to, naturally derived compounds, such as ericamide, or synthetic compounds, such as any compounds set forth in U.S. Pat. Nos. 8,735,081; 8,124,121; and 8,968,708. The mogroside compound (or comestibly acceptable salts thereof) may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise the mogroside compound, or any comestibly acceptable salts thereof, according to any of the embodiments or combination of embodiments set forth above, are combined with one or more cooling enhancing compounds. Such cooling enhancing compounds include, but are not limited to, naturally derived compounds, such as menthol or analogs thereof, or synthetic compounds, such as any compounds set forth in U.S. Pat. Nos. 9,394,287 and 10,421,727. The mogroside compound (or comestibly acceptable salts thereof) may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise the mogroside compound, or any comestibly acceptable salts thereof, according to any of the embodiments or combination of embodiments set forth above, are combined with one or more bitterness blocking compounds. Such bitterness blocking compounds include, but are not limited to, naturally derived compounds, such as menthol or analogs thereof, or synthetic compounds, such as any compounds set forth in U.S. Pat. Nos. 8,076,491; 8,445,692; and 9,247,759. The mogroside compound (or comestibly acceptable salts thereof) may be used in combination with such bitterness blockers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise the mogroside compound, or any comestibly acceptable salts thereof, according to any of the embodiments or combination of embodiments set forth above, are combined with one or more sour taste modulating compounds. The mogroside compound (or comestibly acceptable salts thereof) may be used in combination with such sour taste modulating compounds in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise the mogroside compound, or any comestibly acceptable salts thereof, according to any of the embodiments or combination of embodiments set forth above, are combined with one or more mouthfeel modifying compounds. Such mouthfeel modifying compounds include, but are not limited to, tannins, cellulosic materials, bamboo powder, and the like. The mogroside compound (or comestibly acceptable salts thereof) may be used in combination with such mouthfeel enhancers in any suitable ratio (w/w) ranging from 1:1000 to 1000:1, or from 1:100 to 100:1, or fro, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise the mogroside compound, or any comestibly acceptable salts thereof, according to any of the embodiments or combination of embodiments set forth above, are combined with one or more flavor masking compounds. Such flavor masking compounds include, but are not limited to, cellulosic materials, materials extracted from fungus, materials extracted from plants, citric acid, carbonic acid (or carbonates), and the like. The mogroside compound (or comestibly acceptable salts thereof) may be used in combination with such mouthfeel enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some embodiments of the foregoing embodiments, the comestible composition further comprises a foodstuff base.

For the purpose of the present disclosure, "foodstuff base" means an edible product, e.g. a food or a beverage. Therefore, a flavored article provided herein comprises the functional formulation, as well as optionally additional benefit agents, corresponding to a desired edible product, e.g. a savory cube, and a flavor effective amount of the at least one compound according to an aspect presented herein.

The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

The food product may be selected from the group consisting of condiments, baked goods, powdery food, bakery filings and fluid dairy products.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

Fluid dairy products include, without limitation, non-frozen, partially frozen and frozen fluid dairy products such as, for example, milks, ice creams, sorbets and yogurts. Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra-high temperature, ohmic heating or commercial aseptic sterilization) and hot-filled packaging; and cold-filled products made through filtration or other preservation techniques.

The nature and type of the constituents of the foodstuffs or beverages do not warrant a more detailed description here, which in any case would not be exhaustive, the skilled person being able to select them on the basis of his general knowledge and according to the nature of the product.

The proportions in which the at least one compound according to an aspect presented herein can be incorporated into the various aforementioned articles or compositions vary within a wide range of values. These values are dependent on the nature of the article to be flavored and on the desired organoleptic effect as well as the nature of the co-ingredients in a given base when the compounds according to the invention are mixed with flavoring co-ingredients, solvents or additives commonly used in the art.

In the case of flavoring compositions, typical concentrations are in the order of 0.0001% to 1% by weight, or even more, of the at least one compound according to an aspect presented herein based on the weight of the consumer product into which they are incorporated. Concentrations lower than these, such as in the order of 0.001% to 0.5% by weight, can be used when the at least one compound according to an aspect presented herein are incorporated into flavored articles, percentage being relative to the weight of the article.

EXAMPLES

Example 1: Purification of (1S,4R,9beta,11alpha, 24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 µm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 µm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 µm, 10*250 mm, 14-21% ACN in water, 4.5 mL/min) to afford (1S,4R,9beta,11alpha,24R)-1-{[6-O-(beta-D-glucopyranosyl)-beta-D-glucopyranosyl]oxy}-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside IVa, Compound 1a) (50 mg, purity: 97%).

Referring to mass spectroscopy and NMR analysis shown in FIGS. 2 to 4, the following structure was deduced:

No taste was perceived when a sample of the purified compound was tasted at a concentration of 250 ppm.

Example 2: Purification of (1S,4R,9beta,11alpha, 24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 µm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 µm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 µm, 10*250 mm, 14-21% ACN in water, 4.5 mL/min) to afford (1S,4R,9beta,11alpha,24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-mogroside III, Compound 2a) (200 mg, purity: 94%).

Referring to mass spectroscopy and NMR analysis shown in FIGS. 5 to 7, the following structure was deduced:

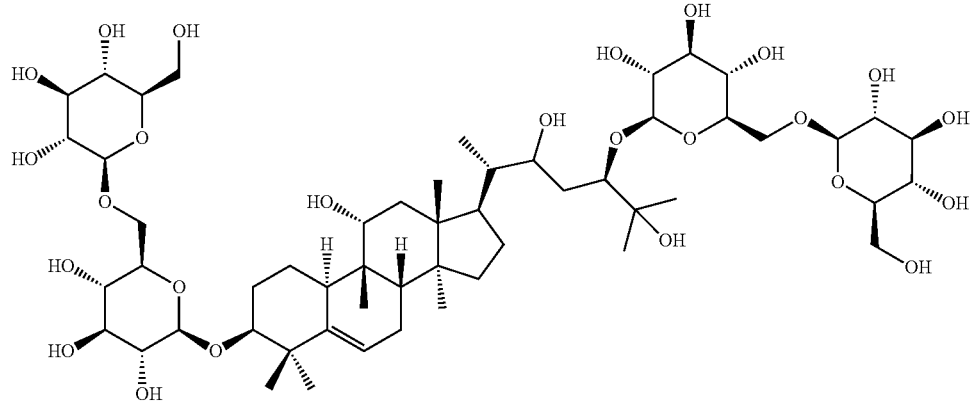

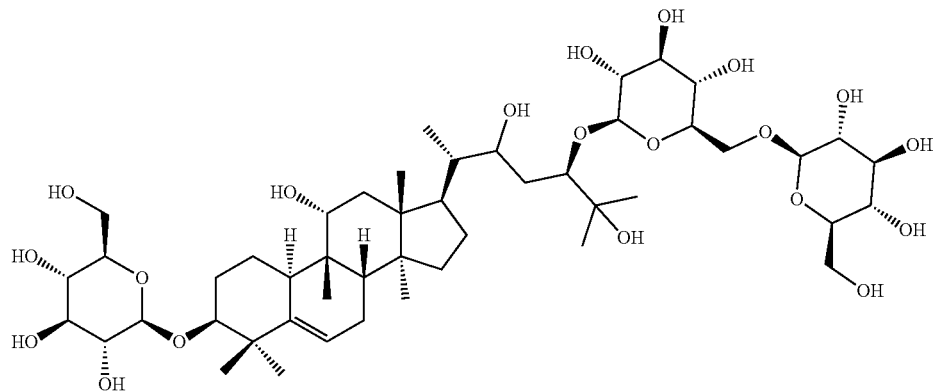

A weak sweet taste, approximately 20-50 times sweeter than sucrose was perceived when a sample of the purified compound was tasted at a concentration of 500 ppm in a water base.

Example 3: Purification of (1S,4R,9beta,11beta, 24R)-1-(beta-D-glucopyranosyloxy)-11,22,25-trihydroxy-9,10,14-trimethyl-4,9-cyclo-9,10-secocholest-5-en-24-yl 6-O-beta-D-glucopyranosyl-beta-D-glucopyranoside (22-hydroxy-11-epi-mogroside III, Compound 2b) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,11beta,24R)-1-(beta-D-glucopyranosyloxy)-11,22,25-trihydroxy-9,10,14-trimethyl-4, 9-cyclo-9,10-secocholest-5-en-24-yl 6-O-beta-D-glucopyranosyl-beta-D-glucopyranoside (22-hydroxy-11-epi-mogroside III, Compound 2b) (50 mg, purity: 95%).

Referring to mass spectroscopy and NMR analysis shown in FIGS. 8 to 10, the following structure was deduced:

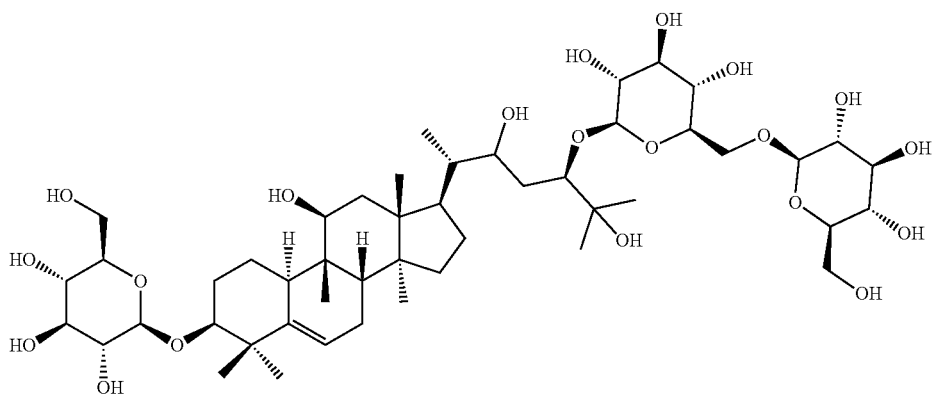

No taste was perceived when a sample of the purified compound was tasted at a concentration of 250 ppm.

Example 4: Purification of (1S,4R,9beta,11alpha, 24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 µm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 µm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 µm, 10*250 mm, 14-21% ACN in water, 4.5 mL/min) to afford (1S,4R,9beta,11alpha,24R)-24-{[6-O-(beta-D-glucopyranosyl)-beta-D-glucopyranosyl]oxy}-11,22,25-trihydroxy-9,10,14-trimethyl-4,9-cyclo-9,10-secocholest-5-en-1-yl 4-O-beta-D-glucopyranosyl-beta-D-glucopyranoside (22-hydroxy-isomogroside IVa, Compound 3a) (50 mg, purity: 97%).

Referring to mass spectroscopy and NMR analysis shown in FIGS. 11 to 13, the following structure was deduced:

No taste was perceived when a sample of the purified compound was tasted at a concentration of 250 ppm.

Example 5: Purification of (1S,4R,9beta,11alpha, 24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (7-hydroxy-mogroside V, Compound 4a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 µm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 µm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 µm, 10*250 mm, 14-21% ACN in water, 4.5 mL/min) to afford (1S,4R,9beta,11alpha,24R)-1-{[6-O-(beta-D-glucopyranosyl)-beta-D-glucopyranosyl]oxy}-7,11,25-trihydroxy-9,10,14-trimethyl-4,9-cyclo-9,10-secocholest-5-en-24-yl beta-D-glucopyranosyl-(1→2)-[beta-D-glucopyranosyl-(1-6)]-beta-D-glucopyranoside (7-hydroxy-mogroside V, Compound 4a) (200 mg, purity: 99%).

Referring to mass spectroscopy and NMR analysis shown in FIGS. 14 to 16, the following structure was deduced:

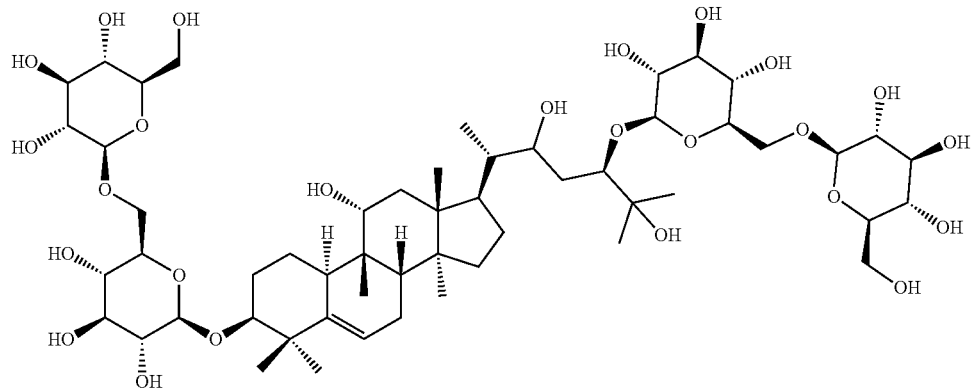

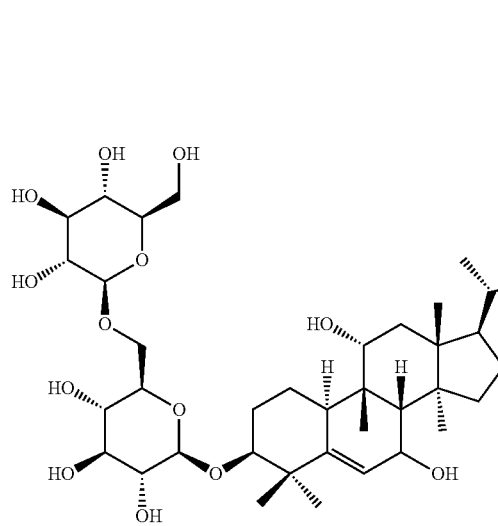

A weak sweet taste, approximately 30-60 times sweeter than sucrose was perceived when a sample of the purified compound was tasted at a concentration of 500 ppm in a water base.

Example 6: Purification of (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 µm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 µm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 µm, 10*250 mm, 14-21% ACN in water, 4.5 mL/min) to afford (1S,4R,9beta,24R)-1-{[6-O-(beta-D-glucopyranosyl)-beta-D-glucopyranosyl]oxy}-25-hydroxy-9-(hydroxymethyl)-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-hydroxyl-11-oxo-mogroside V, Compound 5a) (50 mg, purity: 94%).

Referring to mass spectroscopy and NMR analysis shown in FIGS. 17 to 19, the following structure was deduced:

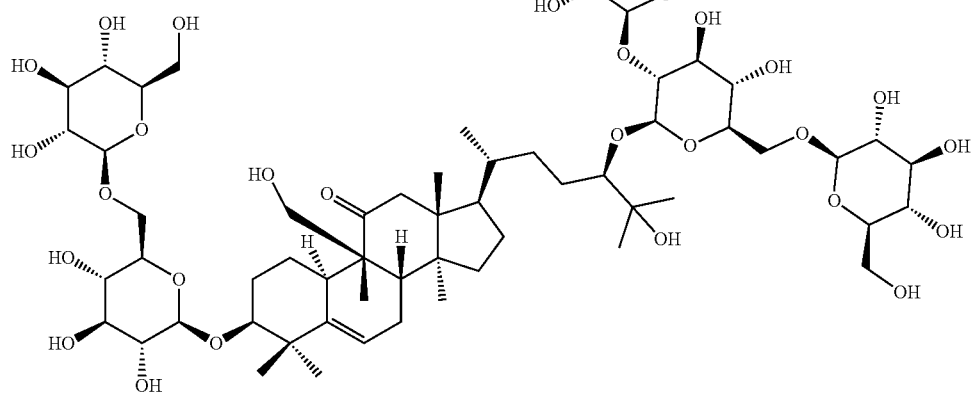

No taste was perceived when a sample of the purified compound was tasted at a concentration of 250 ppm.

Example 7: Purification of (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-secocholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,24R)-9-formyl-1-{[6-O-(beta-D-glucopyranosyl)-beta-D-glucopyranosyl]oxy}-25-hydroxy-10,14-dimethyl-11-oxo-4,9-cyclo-9,10-seco-cholest-5-en-24-yl beta-D-glucopyranosyl-(1→2)-[beta-D-glucopyranosyl-(1→6)]-beta-D-glucopyranoside (19-formyl-11-oxo-mogroside V, Compound 6a) (200 mg, purity: 95%).

Referring to mass spectroscopy and NMR analysis shown in FIGS. 20 to 22, the following structure was deduced:

A strong sweet taste, approximately 100-200 times sweeter than sucrose was perceived when a sample of the purified compound was tasted at a concentration of 500 ppm in a water base.

Example 8: Purification of (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (20-hydroxy-mogroside V, Compound 7a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,11alpha,24R)-1-{[6-O-(beta-D-glucopyranosyl)-beta-D-glucopyranosyl]oxy}-11,20,25-trihydroxy-9,10,14-trimethyl-4,9-cyclo-9,10-seco-cholest-5-en-24-yl beta-D-glucopyranosyl-(1→2)-[beta-D-glucopyranosyl-(1-6)]-beta-D-glucopyranoside (20-hydroxy-mogroside V, Compound 7a) (50 mg, purity: 98%).

Referring to mass spectroscopy and NMR analysis shown in FIGS. 23 to 25, the following structure was deduced:

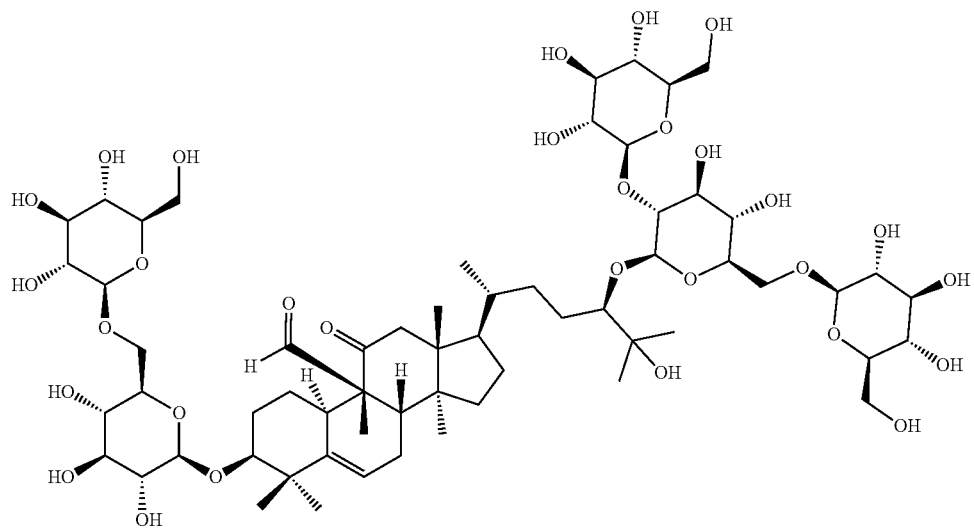

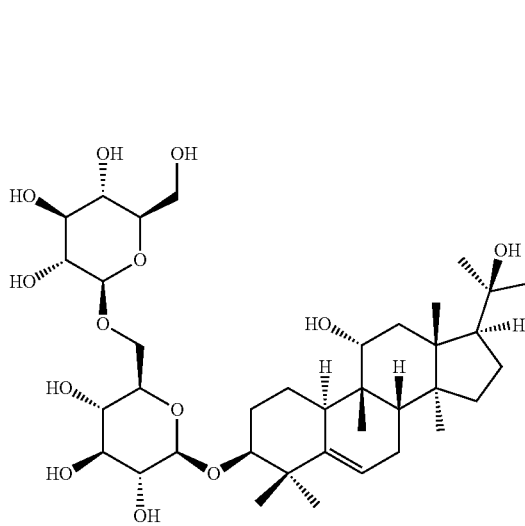
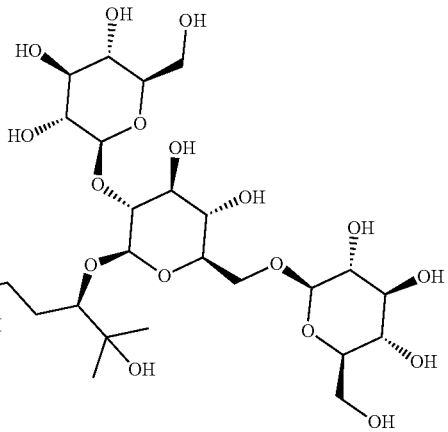

No taste was perceived when a sample of the purified compound was tasted at a concentration of 250 ppm.

Example 9: Purification of (1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford 1S,4R,9beta,24R)-1-(beta-D-glucopyranosyloxy)-20,25-dihydroxy-9,10,14-trimethyl-11-oxo-4,9-cyclo-9,10-secocholest-5-en-24-yl 6-O-beta-D-glucopyranosyl-beta-D-glucopyranoside (20-hydroxy-11-oxo-mogroside III, Compound 8a) (50 mg, purity: 96%).

Referring to mass spectroscopy and NMR analysis shown in FIGS. 26 to 28, the following structure was deduced:

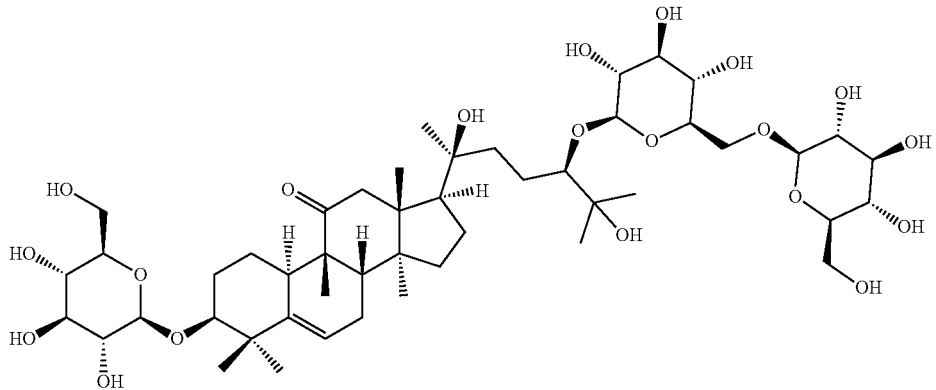

No taste was perceived when a sample of the purified compound was tasted at a concentration of 250 ppm.

Example 10: Purification of (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,24R)-24-{[6-O-(beta-D-glucopyranosyl)-beta-D-glucopyranosyl]oxy}-20,25-dihydroxy-9,10,14-trimethyl-11-oxo-4,9-cyclo-9,10-secocholest-5-en-1-yl beta-D-glucopyranosyl-(1→2)-[beta-D-glucopyranosyl-(1→6)]-beta-D-glucopyranoside (Compound 9a) (50 mg, purity: 95%).

Referring to mass spectroscopy and NMR analysis shown in FIGS. 29 to 31, the following structure was deduced:

Example 11: Purification of [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford [(1S,4R,9beta,10R,24R)-24-{[beta-D-glucopyranosyl-(1→6)-beta-D-glucopyranosyl-(1→6)-beta-D-glucopyranosyl]oxy}-1,25-dihydroxy-9,14-dimethyl-11-oxo-4,9-cyclo-9,10-secocholest-5-en-10-yl]methyl beta-D-glucopyranosyl-(1→6)-[beta-D-glucopyranosyl-(1→4)-beta-D-glucopyranosyl-(1→2)]-beta-D-glucopyranoside (Compound 10a) (50 mg, purity: 93%).

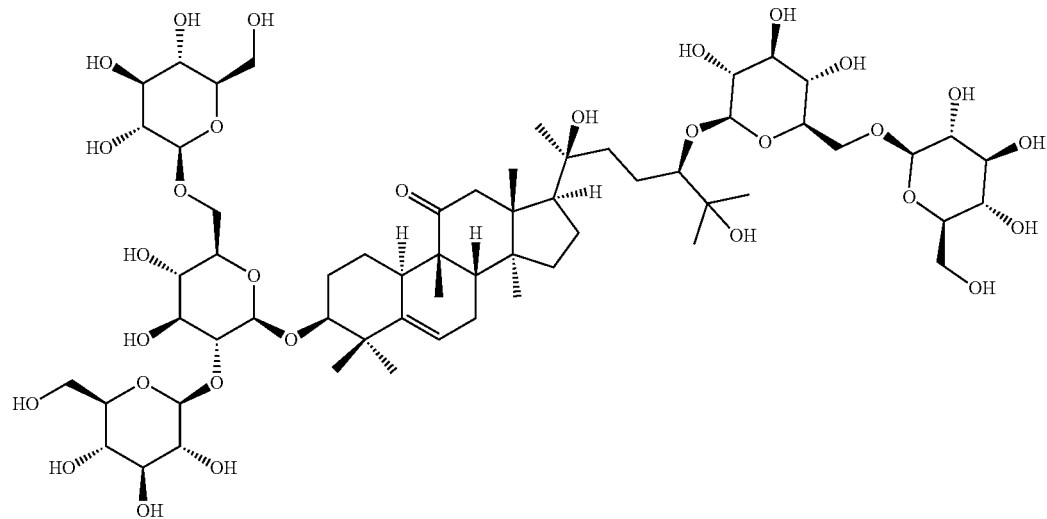

No taste was perceived when a sample of the purified compound was tasted at a concentration of 250 ppm.

Referring to mass spectroscopy and NMR analysis shown in FIGS. 32 to 34, the following structure was deduced:

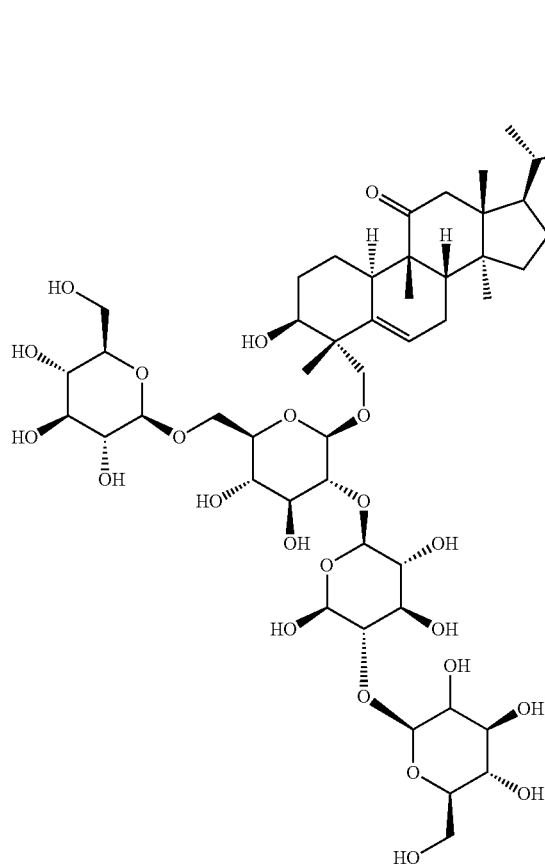
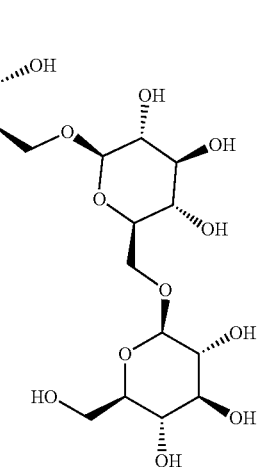

No taste was perceived when a sample of the purified compound was tasted at a concentration of 250 ppm.

Example 12: Purification of (1S,4R,9beta,11alpha, 24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a) from an Extract of Siraitia grosvenorrii 60 kg of Siraitia grosvenorrii extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford 1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→6)-[beta-D-glucopyranosyl-(1→4)-beta-D-glucopyranosyl-(1→2)]-beta-D-glucopyranoside (Compound 12a) (50 mg, purity: 96%).

Referring to mass spectroscopy and NMR analysis shown in FIGS. 35 to 37, the following structure was deduced:

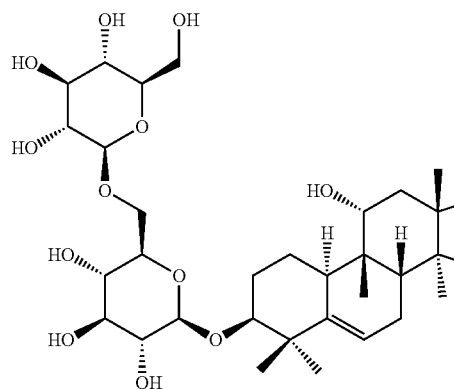
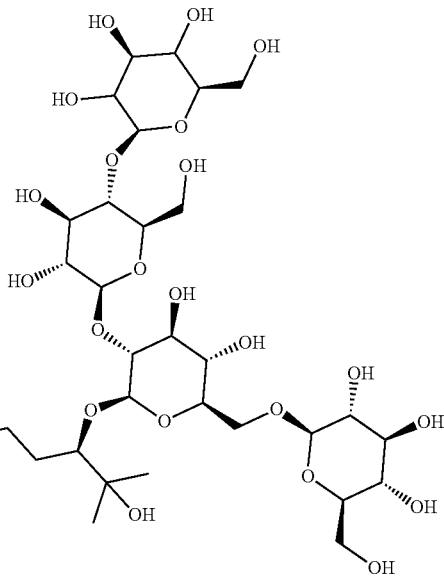

A moderate sweet taste, approximately 50-100 times sweeter than sucrose was perceived when a sample of the purified compound was tasted at a concentration of 250 ppm in a water base. The sweetness intensity perceived was weaker than the sweetness intensity perceived with mogroside V. However, the perception of licorice and lingering profile of isomogroside IVe was weaker than that of mogroside V (see table on following page).

| Dosage (250 ppm) | Sweet | Licorice | Lingering |
|---|---|---|---|
| Mogroside V | 6.0 | 3.8 | 4.9 |
| Compound 12a | 3.4 | 3.1 | 3.0 |

Example 13: Purification of (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,11alpha,24R)-1-{[6-O-(beta-D-glucopyranosyl)-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)-beta-D-glucopyranosyl-(1→6)]-beta-D-glucopyranoside (Compound 13a) (50 mg, purity: 99%).

Referring to mass spectroscopy and NMR analysis shown in FIGS. 38 to 40, the following structure was deduced:

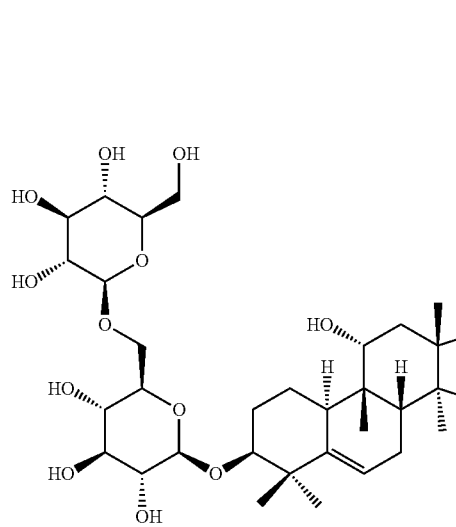
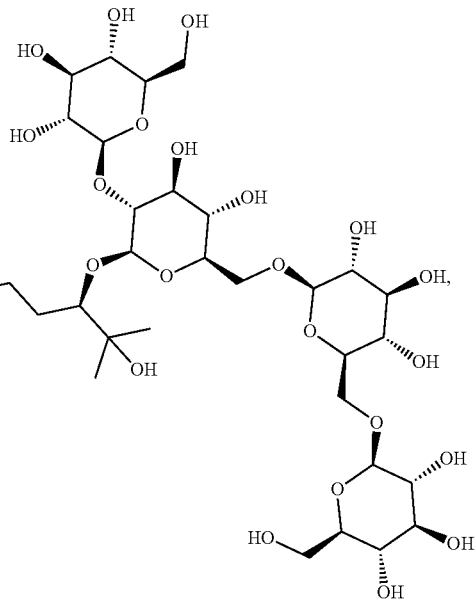

A moderate sweet taste, approximately 100-150 times sweeter than sucrose was perceived when a sample of the purified compound was tasted at a concentration of 250 ppm in a water base, with a similar sensory profile to mogroside V (see table below).

| Dosage (250 ppm) | Sweet | Licorice | Lingering |
|---|---|---|---|
| Mogroside V | 6.0 | 3.8 | 4.9 |
| Compound 13a | 4.6 | 4.4 | 4.2 |

Example 14: Purification of (1S,4R,9beta,11beta, 24R)-1-{[beta-D-glucopyranosyl-(1→2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 45 (412 g) was further purified via a C18 flash chromatography column (Daiso ODS, 40-70 μm, 100*490 mm, 26% ACN in water, 70 mL/min), a Sephadex LH-20 column (55*1500 mm, 18% ACN in water, 0.3 to 1.5 mL/min), and a preparative HPLC (YMC ODS, 5 μm, 10*250 mm, 14-21% ACN in water, 4.5 mL/min) to afford (1S,4R,9beta,11beta,24R)-1-{[beta-D-glucopyranosyl-(1-2)-[beta-D-glucopyranosyl-(1→6)]-beta-D-glucopyranosyl]oxy}-11,25-dihydroxy-9,10,14-trimethyl-4,9-cyclo-9,10-secocholest-5-en-24-yl beta-D-glucopyranosyl-(1→2)-[beta-D-glucopyranosyl-(1→6)]-beta-D-glucopyranoside (11-epi-mogroside VI, Compound 14a) (50 mg, purity: 96%).

Referring to mass spectroscopy and NMR analysis shown in FIGS. 41 to 43, the following structure was deduced:

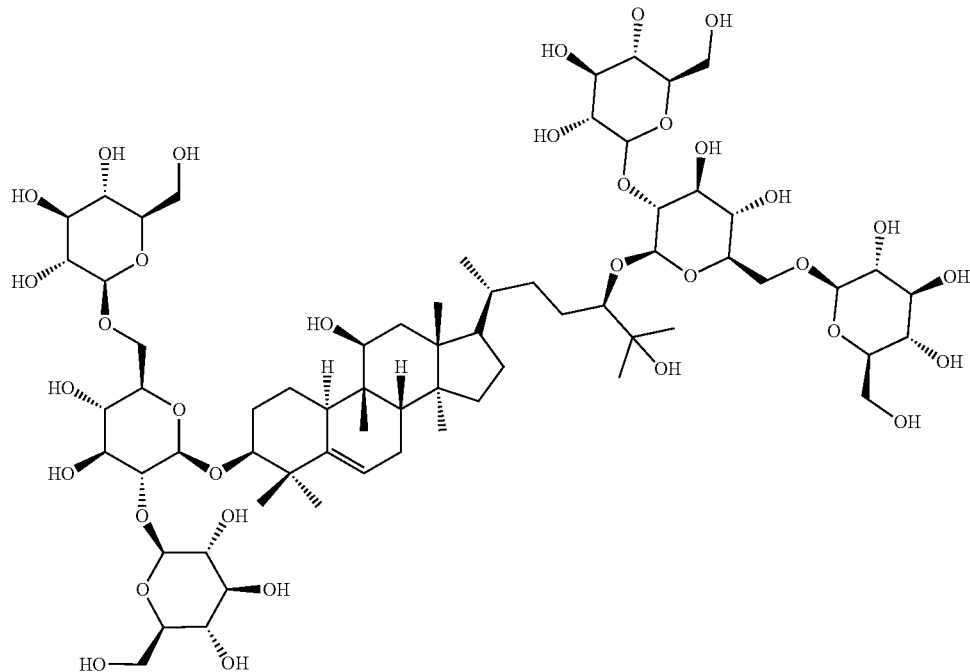

No taste was perceived when a sample of the purified compound was tasted at a concentration of 250 ppm.

Example 15: Purification of (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a) from an Extract of *Siraitia grosvenorrii*

60 kg of *Siraitia grosvenorrii* extract (light yellow liquid, 3.5% of mogroside V) obtained from Gui Lin Layn Natural Ingredients Corp. was dissolved in 150 L de-ionized water and loaded on XDA macroporous resin. The resin was then eluted with water, 5% of EtOH in water and 95% of EtOH in water, and the last fraction enriched in mogrosides was collected as Frac 1 (5.0 kg). Frac 1 was further fractionized on a C18 flash chromatography column (Daiso ODS, 40-70 μm, 100*490 mm). After sample loading, the column was eluted with water, 10%, 20%, 25%, 30%, 40%, 50% ACN in water and 100% of ACN at a flow rate of 70 mL/min, and 16 fractions were collected (Frac. 35-50). Frac. 37 (114 g) was further purified via a C18 flash chromatography column (Daiso ODS, 40-70 μm, 100*490 mm, 41% ACN in water, 70 mL/min), a Sephadex LH-20 column (55*1500 mm, 30% ACN in water, 0.3 to 1.5 mL/min), and a preparative HPLC (YMC ODS, 5 μm, 10*250 mm, 22-30% ACN in water, 4.5 mL/min) to afford (1S,4S,9beta,24R)-1-{[6-O-(beta-D-glucopyranosyl)-beta-D-glucopyranosyl]oxy}-25-hydroxy-9,10,14-trimethyl-4,9-cyclo-9,10-secocholest-5-en-24-yl 2-O-beta-D-glucopyranosyl-beta-D-glucopyranoside (11-deoxymogroside IV, Compound 15a) (200 mg, purity: 93%).

Referring to mass spectroscopy and NMR analysis shown in FIGS. 44 to 46, the following structure was deduced:

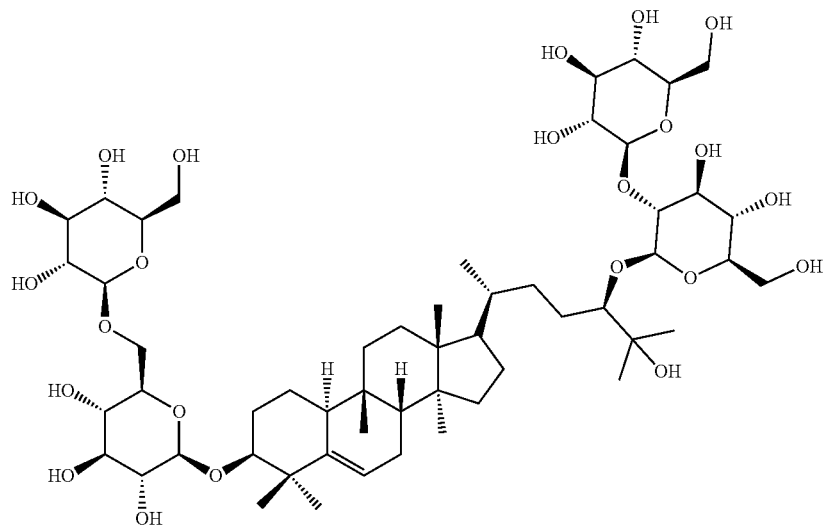

A strong sweet taste, approximately 150-300 times sweeter than sucrose was perceived when a sample of the purified compound was tasted at a concentration of 500 ppm in a water base, with a similar sensory profile to mogroside V (see table below).

| Dosage (500 ppm) | Sweet | Licorice | Lingering |
|---|---|---|---|
| Mogroside V | 7.2 | 4.2 | 5.2 |
| Compound 15a | 7.0 | 6.8 | 6.3 |

The invention claimed is:
1. A compound selected from the group consisting of compounds having the following formulas:

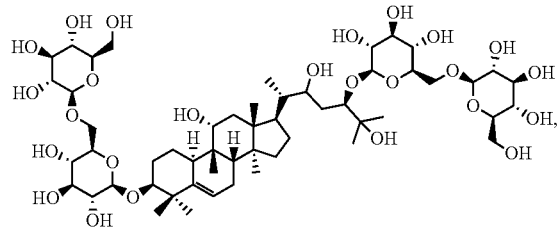

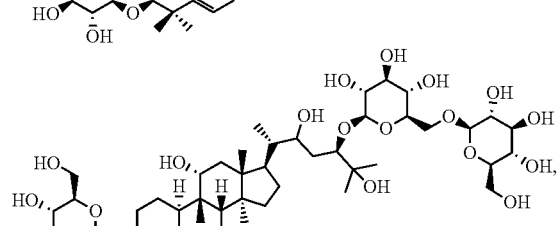

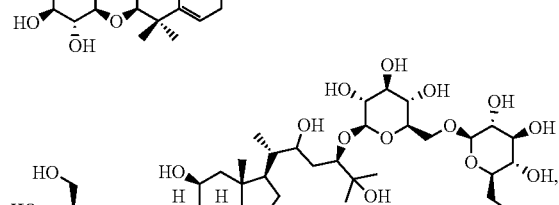

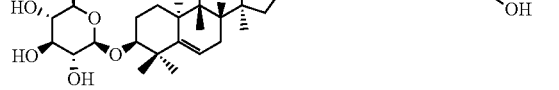

-continued

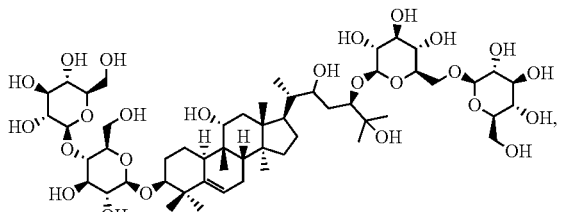

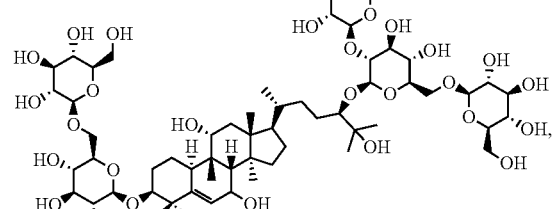

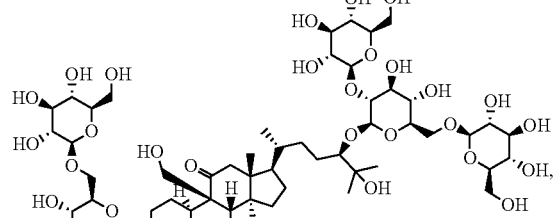

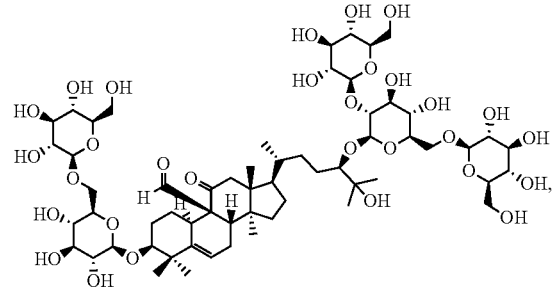

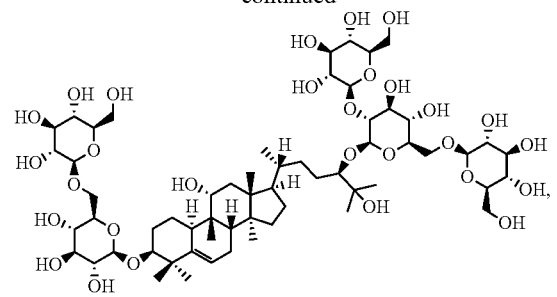
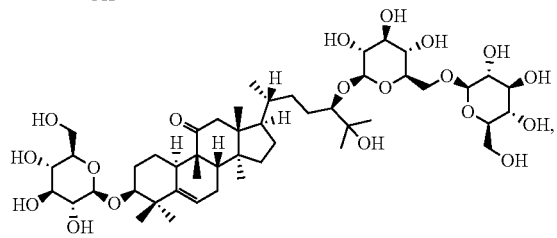
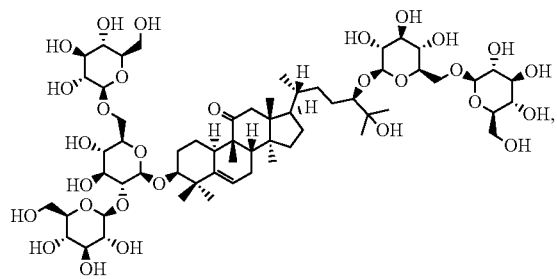
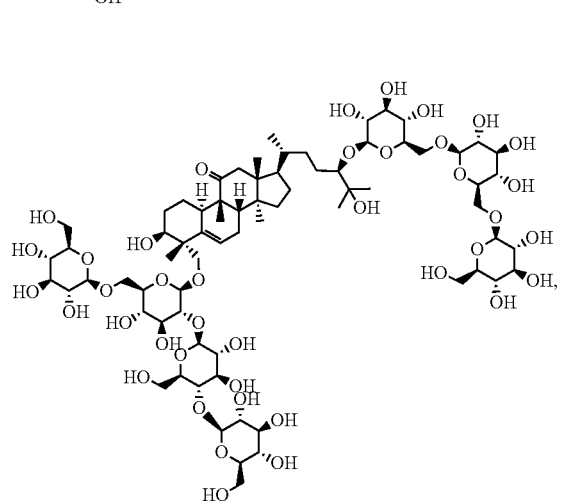
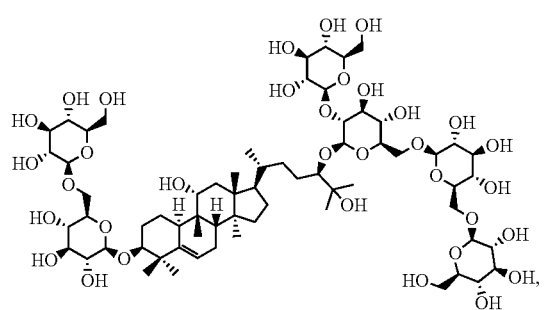
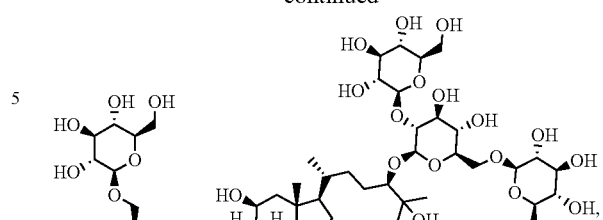
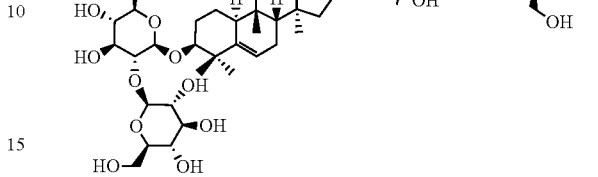
and any salt thereof.
2. The compound of claim 1, wherein the compound is a compound having the formula:
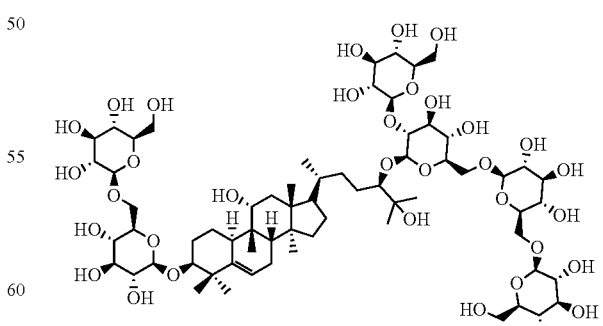
or any salt thereof.
3. The compound of claim 1, wherein the compound is a compound having the formula:

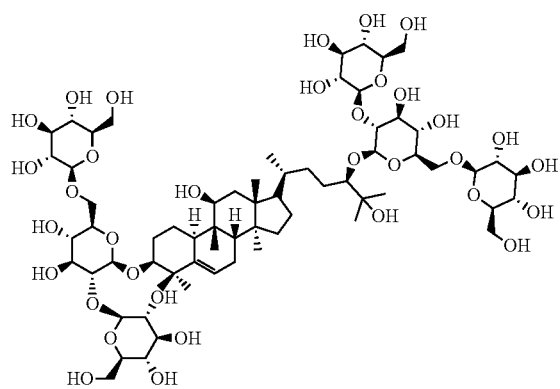

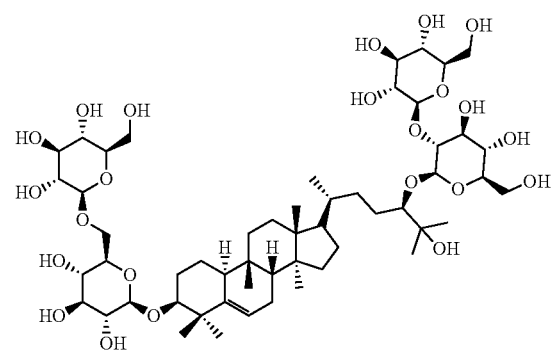

or any salt thereof.

or any salt thereof.

4. The compound of claim 1, wherein the compound is a compound having the formula:

5. A method of imparting a sweet taste or enhancing a sweet taste of a flavored article, the method comprising introducing a compound to the flavored article, wherein the compound is a compound selected from the group consisting having compounds of the following formulas:

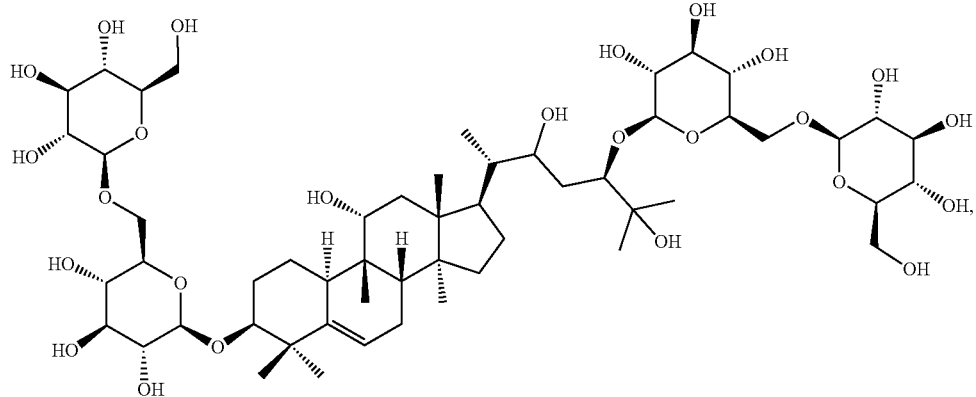

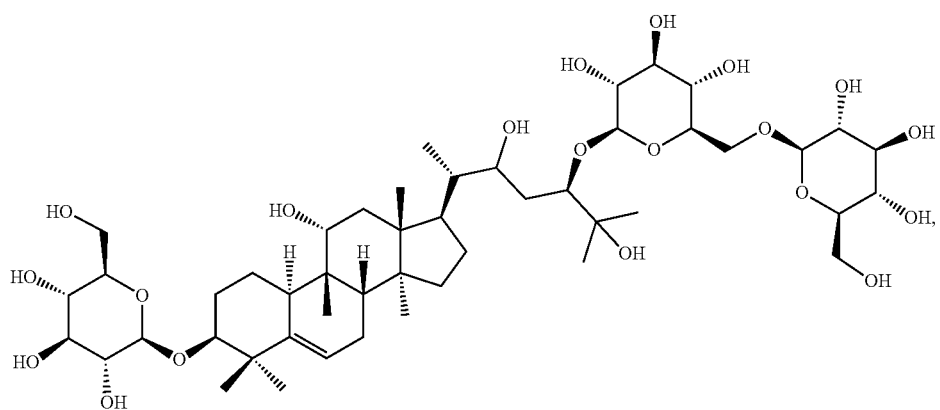

-continued
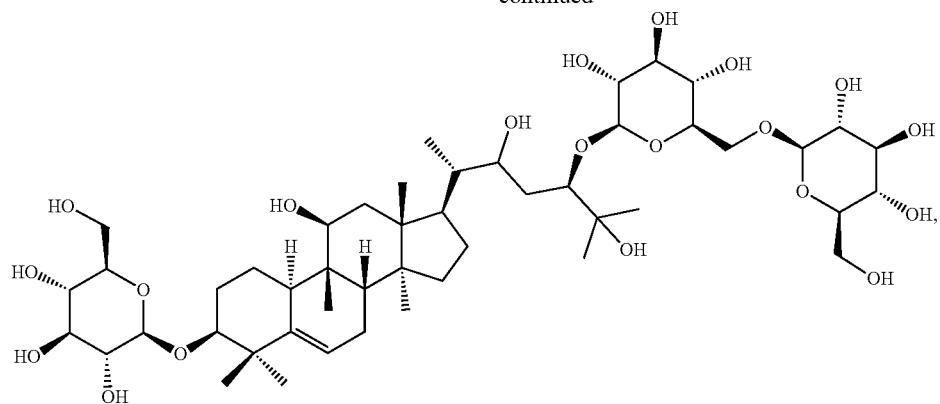
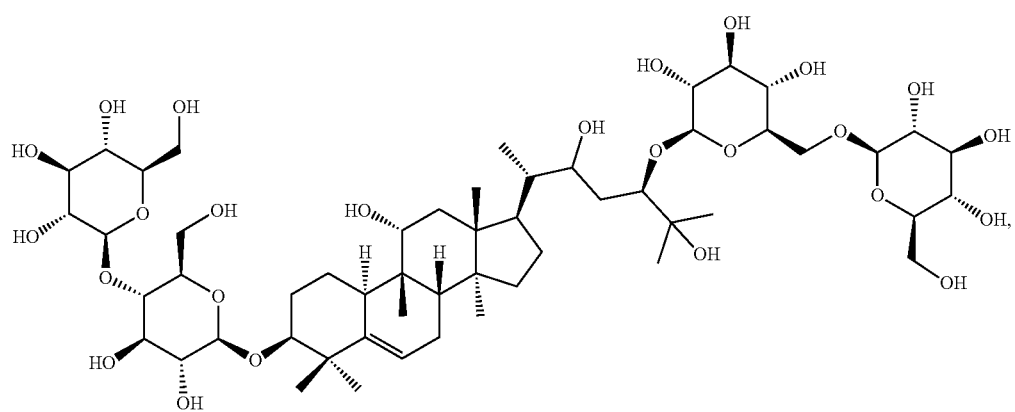
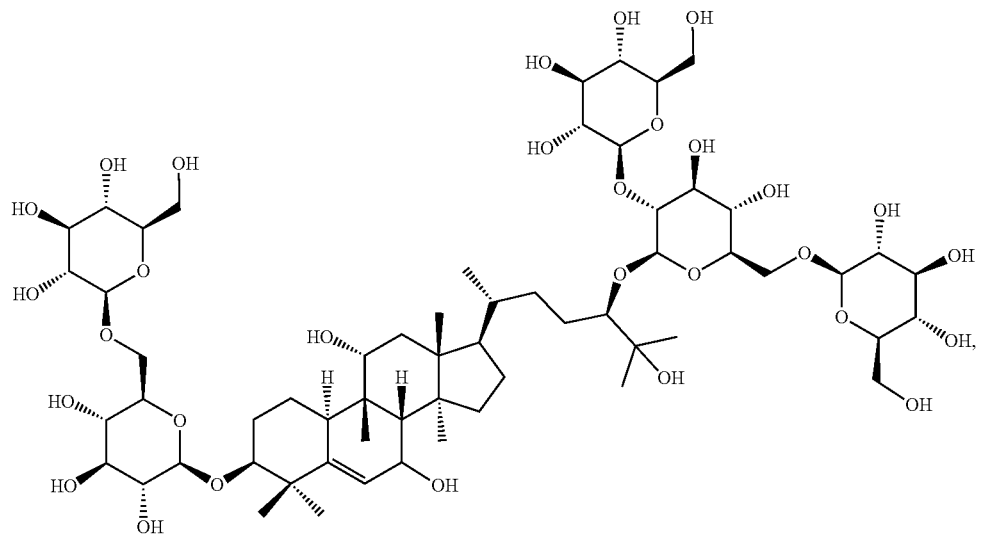

-continued
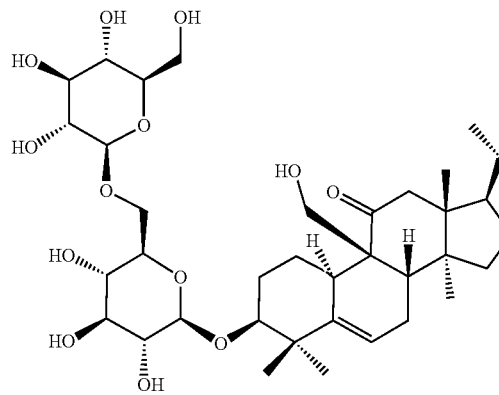
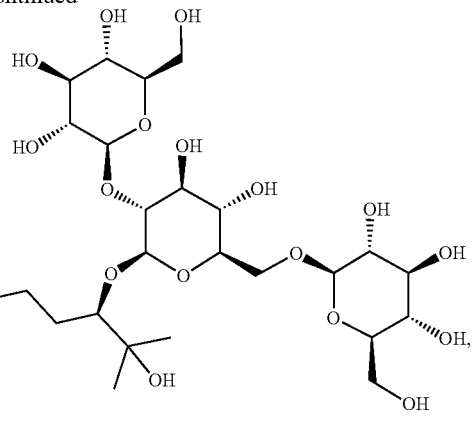
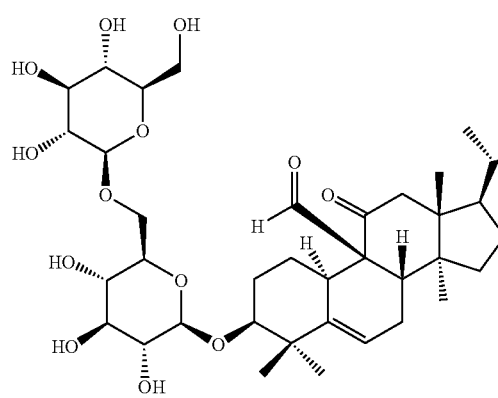
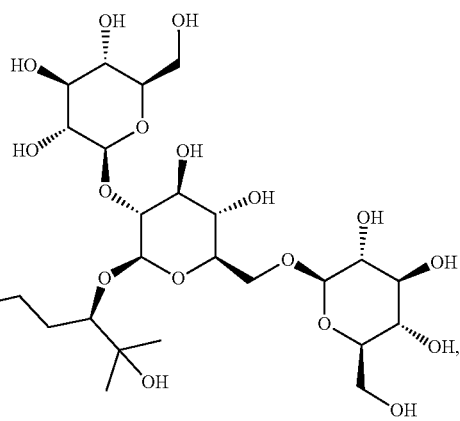
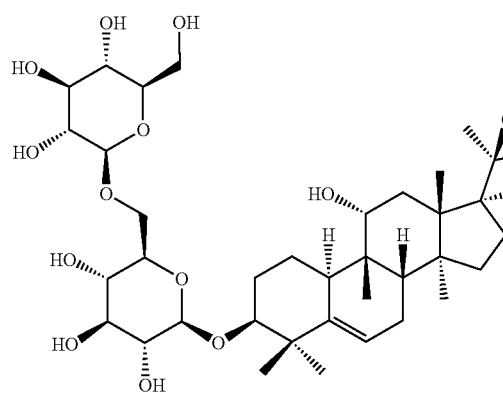
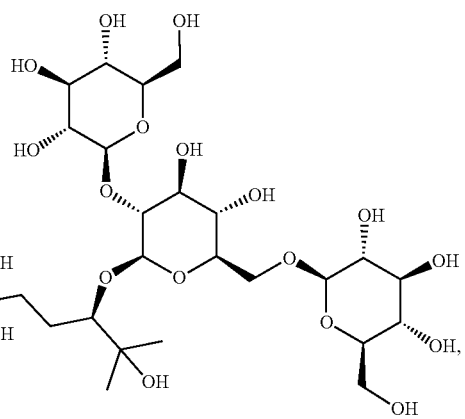

-continued
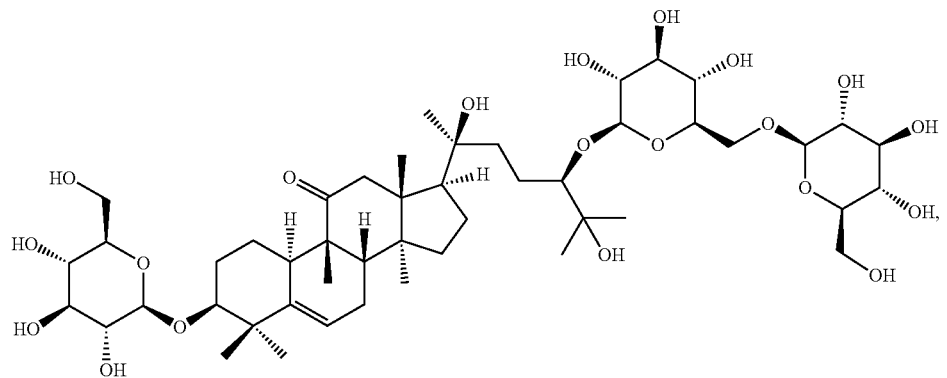
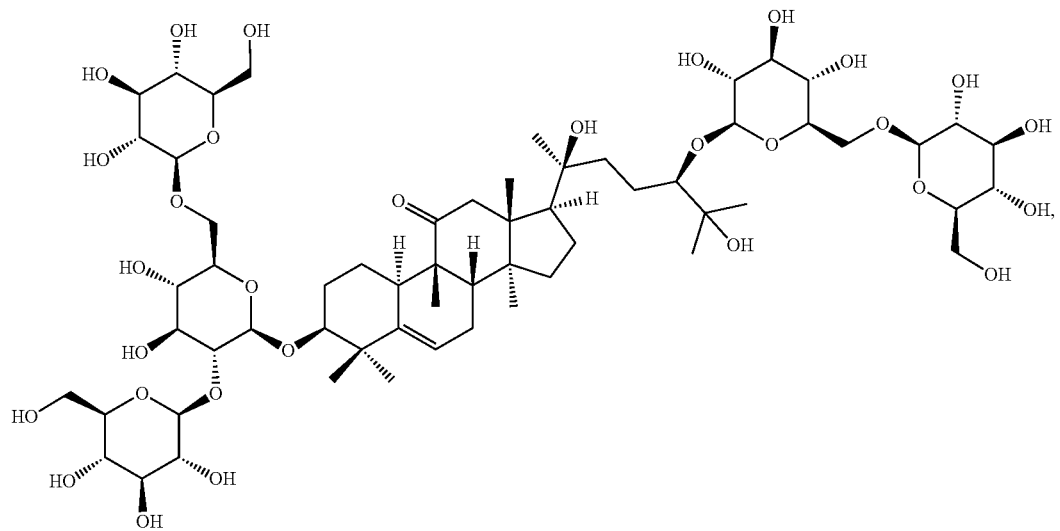
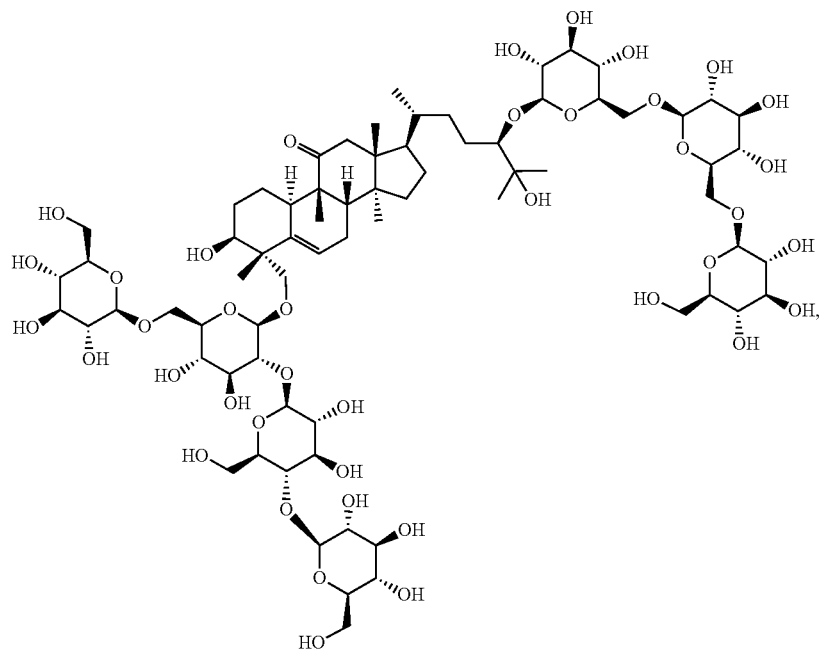

-continued
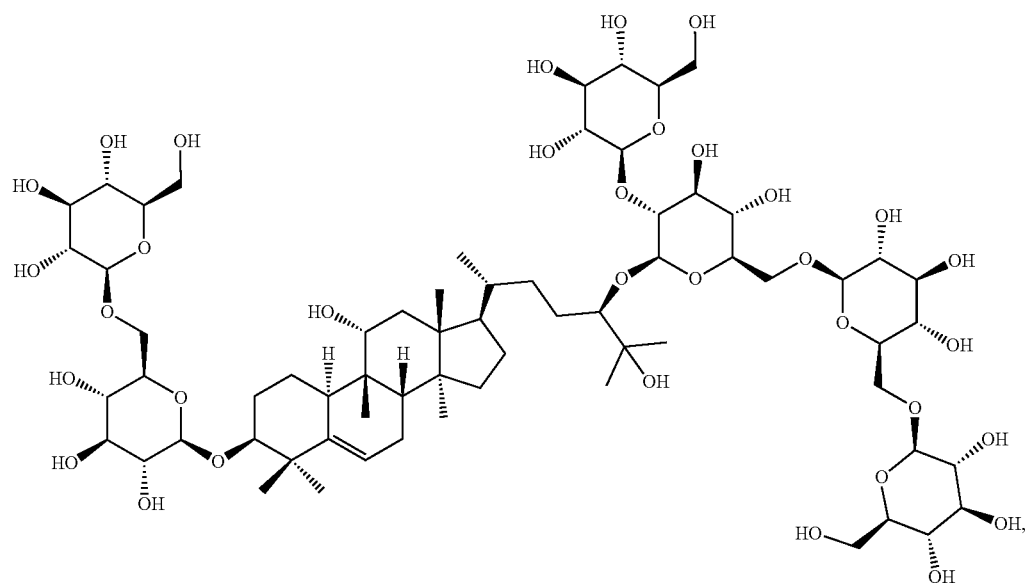
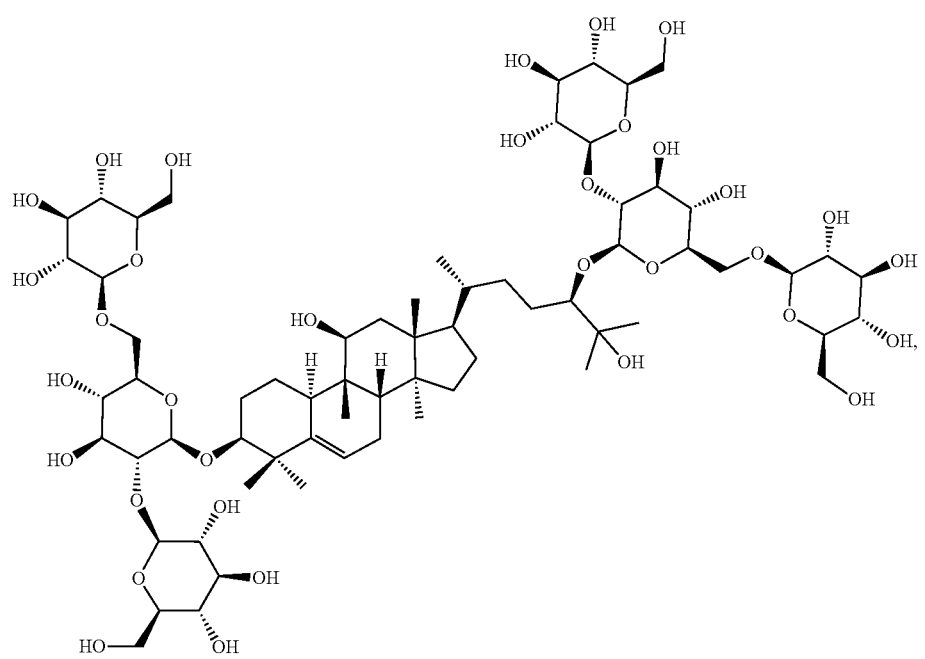

-continued

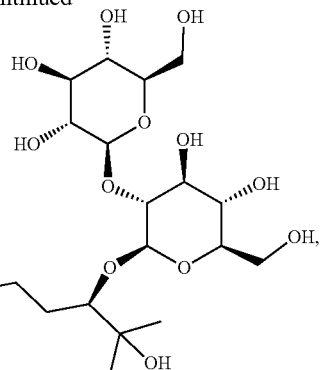
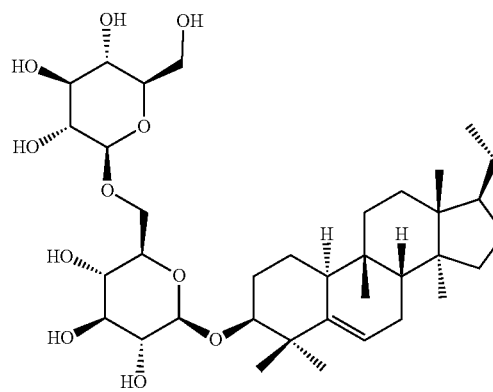

and any salt thereof.

6. The method of claim 5, wherein the flavored article comprises one or more sweeteners selected from the group consisting of sucrose, fructose, glucose, sucralose, one or more rebaudiosides, acesulfame potassium, allulose, erythritol, aspartame, cyclamate, one or more other mogrosides, and any combination thereof.

7. The method of claim 5, wherein the flavored article comprises one or more sweetness enhancing compounds, one or more umami enhancing compounds, one or more cooling enhancing compounds, one or more bitter blocking compounds, one or more sour taste modulating compounds, one or more mouthfeel modifying compounds, one or more flavor masking compounds, or any combination thereof.

8. The method of claim 5, wherein the flavored article is a food product or a beverage product.

9. A comestible composition, the composition comprising one or more compounds of claim 1.

10. The comestible composition of claim 9, further comprising one or more sweeteners selected from the group consisting of sucrose, fructose, glucose, sucralose, one or more rebaudiosides, acesulfame potassium, allulose, erythritol, aspartame, cyclamate, one or more other mogrosides, and any combination thereof.

11. The comestible composition of claim 9, further comprising one or more sweetness enhancing compounds, one or more umami enhancing compounds, one or more cooling enhancing compounds, one or more bitter blocking compounds, one or more sour taste modulating compounds, one or more mouthfeel modifying compounds, one or more flavor masking compounds, or any combination thereof.

12. The comestible composition of claim 9, further comprising a bulking agent, a foodstuff, or any combination thereof.

13. The comestible composition of claim 9, further comprising water.

14. The comestible composition of claim 13, further comprising carbon dioxide, citric acid, malic acid, or any combination thereof.

* * * * *